US010144736B2

(12) United States Patent
Herdewijn et al.

(10) Patent No.: US 10,144,736 B2
(45) Date of Patent: Dec. 4, 2018

(54) SUBSTITUTED PTERIDINES USEFUL FOR THE TREATMENT AND PREVENTION OF VIRAL INFECTIONS

(75) Inventors: Piet André Maurits Maria Herdewijn, Rotselaar/Wezemaal (BE); Steven Cesar Alfons De Jonghe, Brussels (BE); William John Watkins, Saratoga, CA (US); Lee Shun Chong, Newark, CA (US)

(73) Assignee: Gilead Sciences, Inc., Foster City, CA (US)

( * ) Notice: Subject to any disclaimer, the term of this patent is extended or adjusted under 35 U.S.C. 154(b) by 810 days.

(21) Appl. No.: 12/374,457

(22) PCT Filed: Jul. 20, 2007

(86) PCT No.: PCT/BE2007/000092
§ 371 (c)(1),
(2), (4) Date: Jan. 20, 2009

(87) PCT Pub. No.: WO2008/009079
PCT Pub. Date: Jan. 24, 2008

(65) Prior Publication Data
US 2010/0305117 A1 Dec. 2, 2010

Related U.S. Application Data

(60) Provisional application No. 60/807,925, filed on Jul. 20, 2006.

(51) Int. Cl.
| | |
|---|---|
| *C07D 487/00* | (2006.01) |
| *C07D 475/02* | (2006.01) |
| *C07D 475/00* | (2006.01) |
| *C07D 475/04* | (2006.01) |
| *C07D 475/06* | (2006.01) |
| *C07D 475/08* | (2006.01) |

(52) U.S. Cl.
CPC ......... *C07D 475/02* (2013.01); *C07D 475/00* (2013.01); *C07D 475/04* (2013.01); *C07D 475/06* (2013.01); *C07D 475/08* (2013.01)

(58) Field of Classification Search
CPC .. C07D 457/00; C07D 457/02; C07D 457/04; C07D 457/06; C07D 457/08
USPC ........................................ 544/236
See application file for complete search history.

(56) References Cited

U.S. PATENT DOCUMENTS

| | | | |
|---|---|---|---|
| 2,512,572 A | 6/1950 | Smith, Jr. et al. | |
| 2,581,889 A | 1/1952 | Timmis | |
| 2,665,275 A | 1/1954 | Campbell et al. | |
| 2,667,486 A | 1/1954 | Cain | |
| 2,740,784 A | 4/1956 | Sletzinger et al. | |
| 2,939,882 A | 6/1960 | Mecorney | |
| 2,940,972 A | 6/1960 | Roch | |
| 3,071,587 A | 1/1963 | Curran et al. | |
| 3,081,230 A | 3/1963 | Weinstock et al. | |
| 3,122,546 A | 2/1964 | Osdene | |
| 3,159,628 A | 12/1964 | Pachter et al. | |
| 3,162,635 A | 12/1964 | Schroeder | |
| 3,475,425 A | 10/1969 | Roch | |
| 3,859,287 A | 1/1975 | Parish et al. | |
| 5,047,405 A | 9/1991 | Gennari | |
| 5,300,509 A | 4/1994 | Block et al. | |
| 5,354,776 A * | 10/1994 | Chandraratna ...... | C07D 213/80 514/461 |
| 5,380,724 A | 1/1995 | Zubovics et al. | |
| 5,500,428 A | 3/1996 | Block et al. | |
| 5,641,783 A | 6/1997 | Klein et al. | |
| 5,665,772 A | 9/1997 | Cottens et al. | |
| 5,780,462 A | 7/1998 | Lee et al. | |
| 5,843,943 A | 12/1998 | Carson et al. | |
| 5,929,046 A | 7/1999 | McMurry et al. | |
| 5,992,713 A | 11/1999 | Manabat | |
| 6,043,228 A | 3/2000 | McMurray et al. | |
| 6,331,547 B1 | 12/2001 | Zhu et al. | |
| 6,440,991 B1 | 8/2002 | Zhu et al. | |
| 6,559,149 B1 | 5/2003 | Matsuoka et al. | |
| 6,844,343 B1 | 1/2005 | Pfleiderer et al. | |
| 6,946,465 B2 | 9/2005 | Waer et al. | |
| 7,276,506 B2 | 10/2007 | Waer et al. | |
| 7,501,513 B2 | 3/2009 | Waer et al. | |
| 2003/0236255 A1 | 12/2003 | Waer et al. | |
| 2004/0030156 A1 * | 2/2004 | Maul ................... | C07D 307/54 549/4 |
| 2004/0077859 A1 | 4/2004 | Waer et al. | |
| 2004/0102447 A1 | 5/2004 | Bonnert et al. | |

(Continued)

FOREIGN PATENT DOCUMENTS

| | | |
|---|---|---|
| CH | 231852 | 7/1944 |
| CN | 1583747 | 2/2005 |

(Continued)

OTHER PUBLICATIONS

Patani et. al. (Chem. Rev. (1996) 96:3147-3176).*
Burger's Medicinal Chemistry (5th Edition, vol. I, pp. 783-802).*
Wang et. al. (Organic Letters (2004) 6:2793-2796).*
Goodman and Gilman's "the Pharmacological Basis for Therapeutics" 10th Edition(2001), Chapter 50 by Hayden, pp. 1313-1315 (Year: 2001).*
International Preliminary Report on Patentability dated Apr. 7, 2009 for International application No. PCT/BE2007/000092, International filing date Jul. 20, 2007.

(Continued)

*Primary Examiner* — Marcos L Sznaidman
(74) *Attorney, Agent, or Firm* — Clark & Elbing LLP

(57) ABSTRACT

The invention provides 4,6-di- and 2,4,6-tri-substituted pteridine derivatives with a specific substitution pattern which exhibit a significant and selective activity against certain types of viral infections, in particular selectively inhibit replication of Flaviridae such as the hepatitis C virus, and are useful for the prevention and treatment of such viral infections.

13 Claims, No Drawings

(56) References Cited

U.S. PATENT DOCUMENTS

| | | | |
|---|---|---|---|
| 2005/0054653 | A1 | 3/2005 | Eisenbrand et al. |
| 2006/0116371 | A1 | 6/2006 | Martyres et al. |
| 2006/0116373 | A1 | 6/2006 | Dollinger et al. |
| 2006/0189620 | A1 | 8/2006 | Waer et al. |
| 2006/0287314 | A1 | 12/2006 | Waer et al. |
| 2007/0004721 | A1 | 1/2007 | Waer et al. |
| 2007/0032477 | A1 | 2/2007 | Waer et al. |
| 2007/0043000 | A1 | 2/2007 | Waer et al. |
| 2007/0287704 | A1 | 12/2007 | Dollinger et al. |
| 2008/0004285 | A1 | 1/2008 | De Jonghe et al. |
| 2008/0027062 | A1 | 1/2008 | Doblhofer et al. |
| 2008/0182870 | A1 | 7/2008 | Bondy et al. |
| 2008/0312227 | A1 | 12/2008 | De Jonghe et al. |
| 2009/0036430 | A1 | 2/2009 | De Jonghe et al. |
| 2009/0131414 | A1 | 5/2009 | De Jonghe et al. |
| 2009/0253696 | A1 | 10/2009 | Herdewijn et al. |
| 2009/0285782 | A1 | 11/2009 | Gao et al. |
| 2009/0318456 | A1* | 12/2009 | Herdewijn et al. ........... 514/249 |
| 2010/0143299 | A1 | 6/2010 | Gao et al. |

FOREIGN PATENT DOCUMENTS

| | | |
|---|---|---|
| DE | 19 21 308 | 1/1971 |
| DE | 267 495 | 5/1989 |
| DE | 40 09 941 | 10/1991 |
| DE | 10 2004 057595 | 6/2006 |
| DE | 10 2004 057645 | 6/2006 |
| EP | 0 108 890 | 5/1984 |
| EP | 0 134 922 | 3/1985 |
| EP | 0 185 259 | 6/1986 |
| EP | 0 290 819 | 11/1988 |
| EP | 0 362 645 | 4/1990 |
| EP | 0 544 445 | 6/1993 |
| EP | 0 574 906 | 12/1993 |
| EP | 0 956 855 | 11/1999 |
| EP | 1 144 412 | 9/2004 |
| EP | 1 479 682 | 11/2004 |
| GB | 677342 | 8/1952 |
| GB | 763044 | 12/1956 |
| GB | 785353 | 10/1957 |
| GB | 2 143 232 | 2/1985 |
| GB | 2 405 793 | 3/2005 |
| WO | WO 93/25712 | 12/1993 |
| WO | WO 94/06431 | 3/1994 |
| WO | WO 94/11001 | 5/1994 |
| WO | WO 94/14065 | 6/1994 |
| WO | WO 94/22449 | 10/1994 |
| WO | WO 95/13075 | 5/1995 |
| WO | WO 95/31469 | 11/1995 |
| WO | WO 95/31987 | 11/1995 |
| WO | WO 95/32203 | 11/1995 |
| WO | WO 96/10568 | 4/1996 |
| WO | WO 96/20710 | 7/1996 |
| WO | WO 97/23616 | 7/1997 |
| WO | WO 97/31920 | 9/1997 |
| WO | WO 97/39358 | 10/1997 |
| WO | WO 98/04558 | 2/1998 |
| WO | WO 98/08516 | 3/1998 |
| WO | WO 98/52948 | 11/1998 |
| WO | WO 2000/39129 | 7/2000 |
| WO | WO 00/45800 | 8/2000 |
| WO | WO 01/19825 | 3/2001 |
| WO | WO 01/21619 | 3/2001 |
| WO | WO 02/32507 | 4/2002 |
| WO | WO 03/062240 | 7/2003 |
| WO | WO 2004/104005 | 12/2004 |
| WO | WO 2005/021003 | * 3/2005 |
| WO | WO 2005/025574 | 3/2005 |
| WO | WO2005021003 | * 3/2005 |
| WO | WO 2005/039587 | 5/2005 |
| WO | WO 2005/063752 | 7/2005 |
| WO | WO 2005/073204 | * 8/2005 |
| WO | WO 2005/021003 | * 10/2005 |
| WO | WO 2006/120251 | 11/2006 |
| WO | WO 2007/135026 | 11/2007 |
| WO | WO 2007/135027 | 11/2007 |
| WO | WO 2008/003149 | 1/2008 |
| WO | WO 2008/009076 | 1/2008 |

OTHER PUBLICATIONS

Database WPI Week 2005, Feb. 23, 2005, Thompson Scientific, London, GB. (XP002498175).

Invitation to Pay Additional Fees and Partial Search Report (PCT/BE2007/000092) dated Oct. 16, 2008.

Abou-Hedeed et al., "Pteridines CVIII Reactions of 6, 7-Dichloro-1, 3-Dimethyllumazine with Sulfur-Nucleophiles," *Pteridines* 7:113-122, 1996.

Baba et al., "Synergistic Antiviral Effects of Antiherpes Compounds and Human Leukocyte Interferon on Varicella-Zoster Virus in Vitro," *Antimicrob. Agents Chemother.* 25:515-517, 1984.

Banker et al. (eds.), "Modern Pharmaceutics: Third Edition, Revised and Expanded," Marcel Dekker, Inc., pp. 451 and 596, 1996.

Beers et al. (eds.), The Merck Manual of Diagnosis and Therapy, Merck Research Laboratories: Whitehouse Station, N.J., *Leukemias*, Chapt. 138:953-954, 1999.

Beers et al. (eds.), The Merck Manual of Diagnosis and Therapy, Merck Research Laboratories: Whitehouse Station, N.J., *Neurologic Disorders*, Sec. 14:1474-1476, 1999.

Black et al., "Agents that Block TNF-α Synthesis or Activity," *Ann. Rep. Med. Chem.* 32:241-250, 1997.

Boon, "Pteridines. Part IV.* Derivatives of 2:4-Diaminopteridine and Related Compounds," *J. Chem. Soc.* 2146-2158, 1957.

Brown et al., "Pteridine Studies. Part XIV. Methylation of 2-Amino-4-hydroxypteridine and Related Compounds," *J. Chem. Soc.* 869:4413-4420, 1961.

Bundgaard (ed.), "Design of Prodrugs," *Elsevier*, p. 1, 1985.

Buu-Hoï et al., "Phthalonimides (1,3,4-Trioxo-1,2,3,4-Tetrahydroisoquinolines) of Potential Biological Interest," *J. Heretocyclic Chem.* 5:545-546, 1968.

Cairo, "Immunology Lecture #20: Transplantation," Columbia University [online] 2003, Retrieved Jul. 12, 2005 from http://healthsciences.columbia.edu/dept/ps/2007/immuno/2006/IM20.pdf (6 pages).

Chantry, "Tumour Necrosis Factor Antagonists," *Exp. Op. Emerging Drugs* 1:5-13, 1999.

Chou et al., "Quantitative Analysis of Dose-Effect Relationships: The Combined Effects of Multiple Drugs or Enzyme Inhibitors," *Adv. Enzyme Regul.* 22:27-55, 1984.

Cottam et al., "Substituted Xanthines, Pteridinediones and Related Compounds as Potential Anti-Inflammatory Agents. Synthesis and Biological Evaluation of Inhibitors of Tumor Necrosis Factor Alpha," *J. Med. Chem.* 39:2-9, 1996.

Database Beilstein, Accession Nos. 6337777 and 6373242, Beilstein Institute for Organic Chemistry, *KGSSAQ Khim. Geterotsikl. Soedin. RU* 9: 1202-1207, 1992. (XP-002296933, 6 pages).

Database Beilstein, Accession Nos. 285496, 252276, and 250719, Beilstein Institute for Organic Chemistry, *Angew. Chem.* 73:695, 704, 1961; *Ber. Bunsen-Ges. Phys. Chem.* 69:458, 462, 465, 1965; *Chem. Ber.* 90:2631, 2633, 2635, 1957; *Chem. Ber.* 95:755, 762, 1962; *Chem. Ber.* 106:3203, 3205, 1973; *Chem. Ber.* 114:699-706, 1981; *Heterocycles* 24:1565-1566, 1986; *Heterocycles* 41:781-788, 1995; *J. Chem. Soc. Perkin Trans.* 2:35-36, 1979; *Justus Liebigs Ann. Chem.* 547:180, 183, 1941; *Liebigs Ann. Chem.* 11:11798-1814, 1984; *Zh. Org. Khim. RU* 32:455-460, 1996. (XP-002296934, 22 pages).

Database Beilstein, Accession Nos. 533693 and 540145, Beilstein Institute for Organic Chemistry, *CHBEAM Chem. Ber.* 93: 2668, 2671, 1960. (XP-002296935, 4 pages).

Database Beilstein, Accession Nos. 9571456 and 9570157, Beilstein Institute for Organic Chemistry, *IASKEA Izv. Akad. Nauk. Ser. Khim. RU* 6:1328-1334, 2003. (XP-002296936, 11 pages).

Database Beilstein, Accession No. 7216143, Beilstein Institute for Organic Chemistry, *HTCYAM Heterocycles EN* 41:7811-788, 1995. (XP-002296937, 3 pages).

Database Beilstein Accession No. 7928670, Beilstein Institute for Organic Chemistry, *HTCYAM Heterocycles EN* 48:1255-1274, 1998. (XP-002296938, 2 pages).

(56) References Cited

OTHER PUBLICATIONS

Database Beilstein, Accession No. 1184281, Beilstein Institute for Organic Chemistry, ZA Pat. No. 6706096, 1968. (XP-002324247, 2 pages).
Ding et al, "Parallel Synthesis of Pteridine Derivatives as Potent Inhibitors for Hepatitis C Virus NS5B RNA-Dependent RNA Polymerase," *Bioorg. Med. Chem. Lett.* 15:675-678, 2005.
Elion et al., "Antagonists of Nucleic Acid Derivatives. VIII. Synergism in Combinations of Biochemically Related Antimetabolites," *J. Biol. Chem.* 208:477-488, 1954.
Elliott et al., "Synthesis of N-10-Methyl-4-Thiofolic Acid and Related Compounds," *J. Med. Chem.* 18:492-496, 1975.
Fröhlich et al., "Inhibition of Neuronal Nitric Oxide Synthase by 4-Amino Pteridine Derivatives: Structure-Activity Relationship of Antagonists of (6R)-5, 6, 7, 8-Tetrahydrobiopterin Cofactor," *J. Med. Chem.* 42:4108-4121, 1999.
Ganellin "Final Report on the Activities of the Medicinal Chemistry Section," 2002, Retrieved Jun. 2, 2004 from www.iupac.org/divisions/VII/VII.M/VIIM-ReportDec2001.pdf (4 pages).
Gerlach et al., "Influence of Pyrimidopyrimidine and Pteridine Derivatives on Phosphate and Adenosine Permeability in Human Erythrocytes," *Arzneimittelforschung* 15:558-563, 1965. (English Abstract).
Giori et al., "Reactivity of 3H-Pyrimido[5, 4-c] [1, 2, 5] Oxadiazin-3-One Towards Carbanions: Synthesis of Pteridine-2, 4-Diones," *J. Heterocyclic Chem.* 23:1661-1665, 1986.
Hayakawa et al., "Synthesis and Biological Evaluation of 4-Morpholino-2-Phenylquinazolines and Related Derivatives as Novel PI3 Kinase p110alpha Inhibitors," *Bioorg. Med. Chem.* 14:6847-6858, 2006.
Higuchi et al., "A Disproportionation of 6-Amino-5-Benzylideneamino-1,3-dimethyluracils in Formamide. Formation of 6,7-Diaryl-1,3-dimethyllumazines and Theophylline," *Heterocycles* 4:977-80, 1976.
Illei et al., "Novel, Non-Antigen-Specific Therapeutic Approaches to Autoimmune/Inflammatory Diseases," *Curr. Op. Immunol.* 12:712-718, 2000.
Israel et al., "Pyrimidine Derivatives. VII. Some Condensed Derivatives of 2, 4, 5-Triamino-6-Methylthiopyrimidine," *J. Pharm. Sci.* 54:1626-1632, 1965.
Iwagaki et al., "Decreased Serum Tryptophan in Patients With Cancer Cachexia Correlates With Increased Serum Neopterin," *Imunol. Investig.* 24:467-478, 1995.
Jackson et al., "6, 7-Disubstituted 2, 4-Diaminoteridines: Novel Inhibitors of Pneumocystis carinii and Toxoplasma gondii Dihydrofolate Reductase," *Antimicrob. Agents Chemother.* 40:1371-1375, 1996.
Kaldrikyan et al., "Pteridine Derivatives. I. Synthesis of Some Substituted 6,7-Diarylpteridines," *Armyanskii Khimicheskii Zhurnal* 29:337-341, 1976 (8 pages, including English translation on pp. 6-8).
Kandror et al., "Radical Arylation of N-Substituted Carboxylic Acid Thioamides and Cyclic Thioamides," *Russ. Chem. Bull.* 31:1873-1876, 1982 (Abstract only).
Kujime et al., "Regioselective Preparation of Pterin 6-Triflate and Its Application to 6-Substituted Pterin Synthesis," *Heterocycles* 57:1841-1850, 2002.
Landauer et al., "A Convenient Synthesis of Some 4-Substituted 5-Aminopyrimidines," *J. Chem. Soc.* 3721-3722, 1953.
Landry et al., "Pharmacologie. Des Cibles Vers L'Indication Thérapeutique," *Cours et Exercices* 177, 2003.
Lensink, "Synthesis and Structure of Sulfonamido Cyclopentadiene Titanium Complexes: X-Ray Structure of Ti($\eta^5$:σ-$C_5H_4CH_2CH_2NSO_2C_6H_4CH_3)Cl_2$," *J. Organometall. Chem.* 553:387-392, 1998.
Lin et al., "Use of the Methylxanthine Derivative A802715 in Transplantation Immunology, I. Strong in Vitro Inhibitory Effects on CD28-Costimulated T Cell Activities," *Transplantation* 63:1813-1818, 1997.
Lin et al., "Use of the Methylxanthine Derivative A802715 in Transplantation Immunology, II. In Vivo Experiments," *Transplantation* 63:1734-1738, 1997.

Magnus et al. "Neural Stem Cells in Inflammatory CNS Diseases: Mechanisms and Therapy," *J. Cell. Mol. Med.* 9:303-319, 2005.
Matter et al., "Structural Requirements for Inhibition of the Neuronal Nitric Oxide Synthase (NOS-I): 3D-QSAR Analysis of 4-Oxo- and 4-Amino-Pteridine-Based Inhibitors," *J. Med. Chem.* 45:2923-2941, 2002.
Merz et al., "Synthesis of 7-Benzylamino-6-chloro-2-piperazino-4-pyrrolidinopteridine and Novel Derivatives Free of Positional Isomers. Potent Inhibitors of cAMP-Specific Phosphodiesterase and of Malignant Tumor Cell Growth," *J. Med. Chem.* 41: 4733-4743, 1998.
Mohr et al., "Pteridines. Part XCVII. Synthesis and Properties of 6-thioxanthopterin and 7-thioisoxanthopterin," *Helv. Chim. Acta* 75: 2317-2326, 1992.
Moreb et al., "The Therapeutic Potential of Interleukin-1 and Tumor Necrosis Factor on Hematopoietic Stem Cells," *Leuk. Lymphoma* 8:267-275, 1992 (Abstract Only).
Murata et al., "A Facile Method for Regioselective 6,7-Disubstitution of Pteridine," *Heterocycles* 53: 1259-1262, 2000.
Nicolaus, "Symbiotic Approach to Drug Design," in Decision Making in Drug Research, Gross (ed.), Raven Press: New York, p. 173-186, 1983.
Neilsen et al., "Unequivocal Syntheses of 6-Methyl- and 6-Phenylisoxanthopterin" *J. Heterocyclic Chem.* 24:1621-1628, 1987.
Obach, "Drug-drug Interactions: An Important Negative Attribute in Drugs," *Drugs Today* 39:301-338, 2003.
Ochoa et al., "Application of Neural Networks to the Study of Structure-Activity Relationships of 6,7-Diarylpteridines as Nematocides" *Med. Chem. Res.* 7:530-545, 1997.
Pfleiderer et al., "Pteridine, XII: Synthese von 2-Amino-4-Alkoxy-Pteridinen," *Chem. Ber.* 94:12-18, 1961.
Ramu et al., "Circumvention of Adriamycin Resistance by Dipyridamole Analogues: A Structure-activity Relationship Study," *Int. J. Cancer* 43: 487-491, 1989.
Rodrigues et al., "Co/$SiO_2$ Catalysts for Selective Hydrogenation of Crotonaldehyde III. Promoting Effect of Zinc," *Appl. Catalysis A: Gen.* 257:201-211, 2004.
Sato et al., "Studies on Pyrazines. Part 37. Synthesis of 6-Propionylpteridine-2,4 (1 H,3H)-dione and its 1- and/or 3-Methyl Derivatives from Marine Natural Products," *J. Chem. Soc.* 1:89-95, 2000.
Spickett et al., "The Synthesis of Compounds With Potential Anti-Folic Acid Activity. Part I. 7-Amino- and 7-Hydroxy-Pteridines," *J. Chem. Soc.* 2887-2891, 1954.
Sugimoto et al., "Regioselective Arylation of 1,3-Dimethyllumazine and Its 5-Oxide by Diazonium Salts" *Pteridines* 8:188-194, 1997.
Taghavi-Moghadam et al., "A New, General, and Regioselective Method for the Synthesis of 2, 6-Disubstituted 4-Aminopteridines," *Tetrahedron Lett.* 38:6835-6836, 1997.
Ulrich, "Kirk-Othmer Encyclopedia of Chemical Technology," Wiley, Chapter 4: Crystallization, 2002 (7 pages).
Vema et al., "Design of EGFR Kinase Inhibitors: A Ligand-Based Approach and its Confirmation with Structure-Based Studies," *Bioorg. Med. Chem.* 11:4643-4653, 2003.
Vinot, "Étude de Ptéridiones-2,4 III Orientation de la Réaction de Condensation D'α-dicétones Avec le Diamino-4,5 Dimethyl-1,3 Uracile," *Bulletin de la Societe Chimique de France* 9-10:2752-2755, 1972.
Vippagunta et al., "Crystalline Solids," *Adv. Drug Del. Rev.* 48:3-26, 2001.
Weinstock et al., "Pteridines. XII. Structure-Activity Relationships of Some Pteridine Diuretics," *J. Med. Chem.* 11:573-579, 1968.
West, "Solid State Chemistry and its Applications," Wiley, pp. 358 & 365, 1988.
Wolff (ed.), "Burger's Medicinal Chemistry and Drug Discovery: Fifth Edition, vol. I: Principles and Practice," Wiley, pp. 975-977, 1995.
Yao et al., "Pteridines. Protection of Pteridines," *Helv. Chim. Acta* 86:1-12, 2003.
Cecil Textbook of Medicine, 20th edition, vol. 2, pp. 2050-2057, 1996.
Cecil Textbook of Medicine, 20th edition, vol. 2, pp. 1992-1996, 1996.

(56) References Cited

OTHER PUBLICATIONS

Anonymous, "FDA mulls drug to slow late-stage Alzheimer's" Retrieved Sep. 24, 2003 from CNN.com (2 pages).
Ankylosing Spondylitis [online]. Retrieved Jul. 27, 2007 from http://www.nlm.nih.gov/medlineplus/print/ankylosingspondylitis.html (3 pages).
Wikipedia entries for Antihistamine, Autoimmunity, List of Autoimmune Diseases, Lupus Erythematosus, and Sjogren's Syndrome, retrieved Dec. 28, 2006 from http://en.wikipedia.org (23 pages).

\* cited by examiner

SUBSTITUTED PTERIDINES USEFUL FOR THE TREATMENT AND PREVENTION OF VIRAL INFECTIONS

CROSS-REFERENCE TO RELATED APPLICATIONS

This application is the U.S. National Stage of International Application No. PCT/BE2007/000092, filed Jul. 20, 2007, which, in turn, claims the benefit of U.S. Provisional Application Ser. No. 60/807,925, filed Jul. 20, 2006.

FIELD OF THE INVENTION

The present invention relates to a group of novel 4,6-di- and 2,4,6-trisubstituted pteridines and to their use as biologically active ingredients for manufacturing medicaments for the prevention or treatment of viral infections, in particular infections by a virus of the Flaviridae family, more specifically for inhibiting replication of hepatitis C virus. The present invention thus also relates to therapeutic and prophylactic methods comprising administration of said specifically 4,6-di- and 2,4,6-trisubstituted pteridine derivatives, or pro-drugs thereof, to mammals, in particular human beings.

BACKGROUND OF THE INVENTION

There is a continuous need in the art for specific and highly therapeutically active compounds for preventing or treating infections due to Flaviridae and pathologic conditions associated therewith, especially hepatitis C. In particular, there is a need in the art to provide drugs which are active against hepatitis C in a minor dose in order to replace existing drugs having significant side effects and to decrease treatment costs.

Hepatitis is an inflammation of the liver that is most often caused by infection with one of three viruses known as hepatitis A, B or C. Hepatitis A virus (HAV) infection is the most common cause of acute hepatitis, and usually resolves spontaneously after several weeks of acute symptoms. Hepatitis B virus (HBV) and hepatitis C virus (HCV) are the most common viral causes of chronic hepatitis, usually defined as liver inflammation persisting for more than six months. HCV is the second most common cause of viral hepatitis in general and most common cause of chronic hepatitis. The World Health Organization estimates that worldwide 170 million people (3% of the world's population) are chronically infected with HCV. These chronic carriers are at risk of developing cirrhosis and/or liver cancer. In studies with a 10 to 20 year follow-up, cirrhosis developed in 20-30% of the patients, 1-5% of whom may develop liver cancer during the next then years. The 15% to 45% of persons with acute hepatitis C who do recover are not subject to long-term complications and do not need treatment. Since HCV and pestiviruses belong to the same virus family and share many similarities (such as, but not limited to, organization of the genome, analogous gene products and replication cycle), pestiviruses may be adopted as a model virus and surrogate for HCV. For example the Bovine Viral Diarrhea Virus (BVDV) is closely related to hepatitis C virus (HCV) and may be used as a surrogate virus in drug development for HCV infection.

HCV is a representative and highly significant member of the Flaviviridae family, a family of positive-strand RNA viruses. This family includes the following genera: Genus *Flavivirus* (type species Yellow fever virus, others include West Nile virus and Dengue Fever), Genus *Hepacivirus* (type species Hepatitis C virus), and Genus *Pestivirus* (type species Bovine viral diarrhea virus (BVDV), others include classical swine fever or hog cholera). Contrary to other families of positive strand RNA viruses such as human immunodeficiency virus (HIV), HCV seems incapable of integrating into the host's genome. The primary immune response to HCV is mounted by cytotoxic T lymphocytes. Unfortunately, this process fails to eradicate infection in most people; in fact, it may contribute to liver inflammation and, ultimately, tissue necrosis. The ability of HCV to escape immune surveillance is the subject of much speculation. One likely means of viral persistence relies on the presence of closely related but heterogeneous populations of viral genomes. Further studies of these quasi-species enable classification of several genotypes and subtypes, which have clinical implications.

The diagnosis of hepatitis C is rarely made during the acute phase of the disease because the majority of people infected experience no symptoms during this phase of the disease. Those who do experience acute phase symptoms are rarely ill enough to seek medical attention. The diagnosis of chronic phase hepatitis C is also challenging due to the absence or lack of specificity of symptoms until advanced liver disease develops, which may not occur until decades into the disease.

Hepatitis C testing begins with serological blood tests used to detect antibodies to HCV. Anti-HCV antibodies can be detected in about 80% of patients within 15 weeks after exposure, in more than 90% of patients within 5 months after exposure, and in more than 97% of patients by 6 months after exposure. Overall, HCV antibody tests have a strong positive predictive value for exposure to the hepatitis C virus, but may miss patients who have not yet developed antibodies (seroconversion), or have an insufficient level of antibodies to detect. Anti-HCV antibodies indicate exposure to the virus, but cannot determine if ongoing infection is present. All persons with positive anti-HCV antibody tests must undergo additional testing for the presence of the hepatitis C virus itself to determine whether current infection is present. The presence of HCV may be tested by using molecular nucleic acid testing methods such as, but not limited to, polymerase chain reaction (PCR), transcription mediated amplification (TMA), or branched DNA amplification. All HCV nucleic acid molecular tests have the capacity to detect not only whether the virus is present, but also to measure the amount of virus present in the blood (the HCV viral load). The HCV viral load is an important factor in determining the probability of response to interferon-base therapy, but does not indicate disease severity nor the likelihood of disease progression.

The goal of treatment is to prevent complications of HCV infection. This is principally achieved by eradication of infection. Accordingly, treatment responses are frequently characterized by the results of HCV RNA testing. Infection is considered eradicated when there is a sustained virologic response (SVR), defined as the absence of HCV RNA in serum by a sensitive test at the end of treatment and 6 months later. Persons who achieve an SVR almost always have a dramatic earlier reduction in the HCV RNA level, referred to as an early virologic response (EVR). Continued absence of detectable virus at termination of treatment is referred to as end of treatment response (ETR). A patient is considered relapsed when HCV RNA becomes undetectable on treatment but is detected again after discontinuation of treatment. Persons in whom HCV RNA levels remain stable on treatment are considered as non-responders, while those whose HCV RNA levels decline but remain detectable are referred to as partial responders.

Current standard of care for HCV treatment is a combination of (pegylated) interferon alpha and the antiviral drug ribavirin for a period of 24 or 48 weeks, depending upon the viral genotype. Should treatment with pegylated ribavirin-interferon not return a viral load reduction after 12 weeks, the chance of treatment success is less than 1%. Current indication for treatment includes patients with proven hepatitis C virus infection and persistent abnormal liver function tests. SVR of 75% or better occur in people with genotypes HCV 2 and 3 within 24 weeks of treatment, about 50% in those with genotype 1 within 48 weeks of treatment and 65% for those with genotype 4 within 48 weeks of treatment. About 80% of hepatitis C patients in the United States exhibit genotype 1, whereas genotype 4 is more common in the Middle East and Africa.

Best results have been achieved with the combination of weekly subcutaneous injections of long-acting peginterferon alpha and oral ribavirin daily. Interferons are substances naturally released by cells in the body after viral invasion. Interferon alfa-2b and peginterferon alfa-2b are synthetic versions of these substances. The protein product is manufactured by recombinant DNA-technology. Second generation interferons are further derivatized by binding to inert polyethylene glycol, thereby altering the pharmacokinetic properties. Ribavirin is a nucleoside analogue, which disrupts viral replication of hepatitis C virus (HCV).

The most common side effects of HCV treatment with (pegylated) interferon include: a decrease in white blood cells and platelets, anemia, nausea, diarrhea, fever, chills, muscle and joint pain, difficulty in concentrating, thyroid dysfunction, hair loss, sleeplessness, irritability, mild to serious depression, and rarely, suicidal thoughts. Other serious adverse events include bone marrow toxicity, cardiovascular disorders, hypersensitivity, endocrine disorders, pulmonary disorders, colitis, pancreatitis, and ophthalmologic disorders (eye and vision problems). (Pegylated) interferon may also cause or make worse fatal or life-threatening neuropsychiatric, autoimmune, ischemic, and infectious disorders. Patients with persistently severe or worsening signs or symptoms of these conditions are advised to stop therapy.

The most common side effect of HCV treatment with ribavirin is anemia, which can be treated with erythropoietin. Other side effects include mood swings, irritability, anxiety, insomnia, abdominal pain, nervousness, breathlessness, rash, hair loss, dry skin, nausea, diarrhea, loss of appetite, dizziness and weight loss. Ribavirin can also cause birth defects. Ribavirin should not be taken in combination with certain HIV drugs such as, but not limited to, didanosine, since lactic acidosis with fatal hepatic steatosis (fatty liver) may occur. Special attention should be taken for treatment with HIV co-infection.

Although the liver is the primary target of infection, studies to better define the steps of HCV infection are greatly hampered by the lack of a suitable animal model for such studies. The recent development of sub-genomic HCV RNA replicons capable of autonomous replication in the human hepatoma cell line, Huh-7, has been a significant advance in the study of HCV biology. The sub-genomic HCV RNA replicon system provides a cell-based assay to evaluate inhibitors of HCV enzymes like the protease, helicase, and RNA-dependant RNA polymerase or to evaluate nucleic acid targeting strategies like antisense RNA and ribozymes.

Targets for HCV Drug development include HCV-encoded enzymes, namely, NS2-3 and NS3-4A proteases, NS3 helicase, and NS5B RNA dependant RNA polymerase. Alternatively, HCV replication can be inhibited by blocking the conserved RNA elements employing a nucleic acid based approach including antisense oligonucleotides, ribozymes, RNA aptamers, RNA decoys, and RNA interference. A major drawback for such nucleic acid based approach is the size and charge of the nucleic acids, and their usually low physiological stability that do not allow for oral administration. Another target option for therapy is by blocking viral entry into the cell by obstruction of binding to HCV receptors such as, but not limited to, CD 209L and L-SIGN.

There is a strong need in the art to improve, or to provide alternatives to, the existing prophylactic or therapeutic solutions to infections by a virus of the Flaviridae family, more specifically HCV infection. In particular there is still a need in the art for providing alternative synthetic molecules having significant HCV replication inhibiting activity. There is also a need in the art for providing effective inhibiting molecules which are free from the significant drawbacks of the current drugs like pegylated interferon and ribavirin. Meeting these various needs in the art constitutes the main goal of the present invention.

SUMMARY OF THE INVENTION

The present invention is based on the unexpected finding that a number of novel specifically substituted pteridines, in particular 4,6-disubstituted pteridines and 2,4,6-trisubstituted pteridines, are capable of exhibiting a significant and selective activity against certain types of viral infections, provided that the substituting pattern of such pteridines is suitably selected. In particular, these selected 4,6-disubstituted pteridines and 2,4,6-trisubstituted pteridines are capable of selectively inhibiting the replication of the hepatitis C virus. As a consequence, the present invention provides pharmaceutical compositions comprising one or more 4,6-disubstituted pteridines and 2,4,6-trisubstituted pteridines in combination with one or more pharmaceutically acceptable excipients. The present invention also provides prophylactic and therapeutic methods of treatment of higher mammals, in particular human beings, through the administration of an effective amount of such selected 4,6-disubstituted pteridines and 2,4,6-trisubstituted pteridines.

Definitions

Unless otherwise stated herein, the term "tri-substituted" in relation to the pteridine structure means that three of the carbon atoms being in positions 2, 4 and 6 of the pteridine moiety (according to standard atom numbering for the pteridine moiety) are substituted with an atom or group of atoms other than hydrogen. Unless otherwise stated herein, the term "di-substituted" in relation to the pteridine structure means that two of the carbon atoms being in positions 4 and 6 of the pteridine moiety (according to standard atom numbering for the pteridine moiety) are substituted with an atom or group of atoms other than hydrogen.

As used herein with respect to a substituting radical, and unless otherwise stated, the term "$C_{1-7}$ alkyl" means straight and branched chain saturated acyclic hydrocarbon monovalent radicals having from 1 to 7 carbon atoms such as, for example, methyl, ethyl, propyl, n-butyl, 1-methyl-ethyl (isopropyl), 2-methylpropyl (isobutyl), 1,1-dimethylethyl (tert-butyl), 2-methyl-butyl, n-pentyl, dimethylpropyl, n-hexyl, 2-methylpentyl, 3-methylpentyl, n-heptyl and the like. By analogy, the term "$C_{1-4}$ alkyl" refers to such radicals having from 1 to 4 carbon atoms, i.e. up to and including butyl, and "$C_{1-12}$ alkyl" refers to such radicals having from 1 to 12 carbon atoms.

As used herein with respect to a substituting radical, and unless otherwise stated, the term "acyl" broadly refers to a substituent derived from an acid such as an organic monocarboxylic acid, a carbonic acid, a carbamic acid (resulting into a carbamoyl substituent) or the thioacid or imidic acid (resulting into a carbamidoyl substituent) corresponding to said acids, and the term "sulfonyl" refers to a substituent derived from an organic sulfonic acid, wherein said acids comprise an aliphatic, aromatic or heterocyclic group in the molecule. A more specific kind of "acyl" group within the scope of the above definition refers to a carbonyl (oxo) group adjacent to a $C_{1-7}$ alkyl, a $C_{3-10}$ cycloalkyl, an aryl, an arylalkyl or a heterocyclic group, all of them being such as herein defined. Suitable examples of acyl groups are to be found below.

Acyl and sulfonyl groups originating from aliphatic or cycloaliphatic monocarboxylic acids are designated herein as aliphatic or cycloaliphatic acyl and sulfonyl groups and include, but are not limited to, the following:
  alkanoyl (for example formyl, acetyl, propionyl, butyryl, isobutyryl, valeryl, isovaleryl, pivaloyl and the like);
  cycloalkanoyl (for example cyclobutanecarbonyl, cyclopentane-carbonyl, cyclo-hexanecarbonyl, 1-adamantanecarbonyl and the like);
  cycloalkyl-alkanoyl (for example cyclohexylacetyl, cyclopentylacetyl and the like);
  alkenoyl (for example acryloyl, methacryloyl, crotonoyl and the like);
  alkylthioalkanoyl (for example methylthioacetyl, ethylthioacetyl and the like);
  alkanesulfonyl (for example mesyl, ethanesulfonyl, propanesulfonyl and the like);
  alkoxycarbonyl (for example methoxycarbonyl, ethoxycarbonyl, propoxycarbonyl, isopropoxycarbonyl, butoxycarbonyl, isobutoxycarbonyl and the like);
  alkylcarbamoyl (for example methylcarbamoyl and the like);
  (N-alkyl)-thiocarbamoyl (for example (N-methyl)-thiocarbamoyl and the like);
  alkylcarbamidoyl (for example methylcarbamidoyl and the like); and
  alkoxyalkyl (for example methoxyalkyl, ethoxyalkyl, propoxyalkyl and the like);

Acyl and sulfonyl groups may also originate from aromatic monocarboxylic acids and include, but are not limited to, the following:
  aroyl (for example benzoyl, toluoyl, xyloyl, 1-naphthoyl, 2-naphthoyl and the like);
  arylalkanoyl (for example phenylacetyl and the like);
  arylalkenoyl (for example cinnamoyl and the like);
  aryloxyalkanoyl (for example phenoxyacetyl and the like);
  arylthioalkanoyl (for example phenylthioacetyl and the like);
  arylaminoalkanoyl (for example N-phenylglycyl, and the like);
  arylsulfonyl (for example benzenesulfonyl, toluenesulfonyl, naphthalenesulfonyl and the like);
  aryloxycarbonyl (for example phenoxycarbonyl, naphthyloxycarbonyl and the like);
  arylalkoxycarbonyl (for example benzyloxycarbonyl and the like);
  arylcarbamoyl (for example phenylcarbamoyl, naphthylcarbamoyl and the like);
  arylglyoxyloyl (for example phenylglyoxyloyl and the like).
  arylthiocarbamoyl (for example phenylthiocarbamoyl and the like); and
  arylcarbamidoyl (for example phenylcarbamidoyl and the like).

Acyl groups may also originate from an heterocyclic monocarboxylic acids and include, but are not limited to, the following:
  heterocyclic-carbonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiophenoyl, furoyl, pyrrolecarbonyl, nicotinoyl and the like); and
  heterocyclic-alkanoyl in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiopheneneacetyl, furylacetyl, imidazolylpropionyl, tetrazolylacetyl, 2-(2-amino-4-thiazolyl)-2-methoxyiminoacetyl and the like).

As used herein with respect to a substituting radical, and unless otherwise stated, the term "$C_{1-7}$ alkylene" means the divalent hydrocarbon radical corres-ponding to the above defined $C_{1-7}$ alkyl, such as methylene, bis(methylene), tris (methylene), tetramethylene, hexamethylene and the like.

As used herein with respect to a substituting radical, and unless otherwise stated, the term "$C_{3-10}$ cycloalkyl" means a mono- or polycyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituting radical, and unless otherwise stated, the term "$C_{3-10}$ cycloalkyl-alkyl" refers to an aliphatic saturated hydrocarbon monovalent radical (preferably a $C_{1-7}$ alkyl such as defined above) to which a $C_{3-10}$ cycloalkyl (such as defined above) is already linked such as, but not limited to, cyclohexylmethyl, cyclopentylmethyl and the like.

As used herein with respect to a substituting radical, and unless otherwise stated, the term "$C_{3-10}$ cycloalkylene" means the divalent hydrocarbon radical corresponding to the above defined $C_{3-10}$ cycloalkyl.

As used herein with respect to a substituting radical, and unless otherwise stated, the term "aryl" designates any mono- or polycyclic aromatic monovalent hydrocarbon radical having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl radicals (the latter being as defined above) such as, for instance, indanyl, tetrahydronaphthyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 4-nitrophenyl, 3,5-dichlorophenyl and the like.

As used herein, e.g. with respect to a substituting radical such as the combination of substituents in certain positions of the pteridine ring together with the carbon atoms in the same positions of said ring, and unless otherwise stated, the term "homocyclic" means a mono- or polycyclic, saturated or mono-unsaturated or polyunsaturated hydrocarbon radical having from 4 up to 15 carbon atoms but including no heteroatom in the said ring; for instance said combination of substituents may form a $C_{2-6}$ alkylene radical, such as tetramethylene, which cyclizes with the carbon atoms in certain positions of the pteridine ring.

As used herein with respect to a substituting radical (including the combination of substituents in certain positions of the pteridine ring together with the carbon atoms in the same positions of said ring), and unless otherwise stated, the terms "heterocyclic" and "heterocyclyl" mean a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphtho-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxathiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiocinyl, benzodioxocinyl, benzotrioxepinyl, benzoxathiazepinyl, benzoxadiazepinyl, benzothiadiazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypoxanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzocarbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenziso quinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphthindazolyl, naphthindolyl, naphthothiazolyl, naphthothioxolyl, naphthoxindolyl, naphthotriazolyl, naphthopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphthothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl (e.g. phthalazinyl), phthalidyl, phthalimidinyl, phthalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may furthermore be independently substituted with a substituent selected from the group consisting of halogen, nitro, $C_{1-7}$ alkyl (optionally containing one or more functions or radicals selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkylhydrazino, phenylhydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkylhydrazino, phenylhydrazino, sulfhydryl, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof; depending upon the number of unsaturations in the 3 to 10 atoms ring, heterocyclic radicals may be sub-divided into heteroaromatic (or "heteroaryl") radicals and non-aromatic heterocyclic radicals; when a heteroatom of said non-aromatic heterocyclic radical is nitrogen, the latter may be substituted with a substituent selected from the group consisting of $C_{1-7}$ alkyl, $C_{3-10}$ cycloalkyl, aryl, arylalkyl and alkylaryl.

As used herein with respect to a substituting radical, and unless otherwise stated, the terms "$C_{1-7}$ alkoxy", "$C_{3-10}$ cycloalkoxy", "aryloxy", "arylalkoxy", "oxyheterocyclic", "heterocyclic-substituted alkoxy", "thio $C_{1-7}$ alkyl", "thio $C_{3-10}$ cycloalkyl", "arylthio", "arylalkylthio" and "thioheterocyclic" refer to substituents wherein a carbon atom of a $C_{1-7}$ alkyl, respectively a $C_{3-10}$ cycloalkyl, aryl, arylalkyl, heterocyclic radical or heterocyclic-substituted alkyl (each of them such as defined herein), is attached to an oxygen atom or a divalent sulfur atom through a single bond such as, but not limited to, methoxy, ethoxy, propoxy, butoxy, pentoxy, isopropoxy, sec-butoxy, tert-butoxy, isopentoxy, cyclopropyloxy, cyclobutyloxy, cyclopentyloxy, thiomethyl, thioethyl, thiopropyl, thiobutyl, thiopentyl, thiocyclopropyl, thiocyclobutyl, thiocyclopentyl, thiophenyl, phenyloxy, benzyloxy, mercaptobenzyl and cresoxy, and various isomers of piperidinoxy, 1-methylpiperidinoxy, pyrrolidinoxy, pyridinoxy, tetrahydrofuranyloxy, morpholino-ethoxy, piperazinoethoxy, piperidinoethoxy, pyridinoethoxy, pyrrolidinoethoxy, piperidinomethoxy, methylpyridinoxy, methylquinolinoxy, pyridinopropoxy and the like.

As used herein with respect to a substituting atom, and unless otherwise stated, the term halogen means any atom selected from the group consisting of fluorine, chlorine, bromine and iodine.

As used herein with respect to a substituting radical, and unless otherwise stated, the term "halo $C_{1-7}$ alkyl" means a $C_{1-7}$ alkyl radical (such as above defined) in which one or more hydrogen atoms are independently replaced by one or more halogens (preferably fluorine, chlorine or bromine), such as but not limited to difluoromethyl, trifluoromethyl, trifluoroethyl, octafluoropentyl, dodecafluoro-heptyl, dichloromethyl and the like.

As used herein with respect to a substituting radical, and unless otherwise stated, the terms "$C_{2-7}$ alkenyl" designate a straight and branched acyclic hydrocarbon monovalent radical having one or more ethylenic unsaturations and having from 2 to 7 carbon atoms such as, for example, vinyl, 1-propenyl, 2-propenyl(allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl and the like, including all possible isomers thereof.

As used herein with respect to a substituting radical, and unless otherwise stated, the term "$C_{3-10}$ cycloalkenyl" means a monocyclic mono- or polyunsaturated hydrocarbon monovalent radical having from 3 to 8 carbon atoms, such as for instance cyclopropenyl, cyclobutenyl, cyclopentenyl, cyclopentadienyl, cyclohexenyl, cyclohexadienyl, cycloheptenyl, cycloheptadienyl, cycloheptatrienyl, cyclooctenyl, cyclooctadienyl and the like, or a $C_{7-10}$ polycyclic mono- or polyunsaturated hydrocarbon mono-valent radical having from 7 to 10 carbon atoms such as dicyclopentadienyl, fenchenyl (including all isomers thereof, such as α-pinolenyl), bicyclo[2.2.1]hept-2-enyl, bicyclo[2.2.1]hepta-2,5-dienyl, cyclofenchenyl and the like.

As used herein with respect to a substituting radical, and unless otherwise stated, the term "$C_{2-7}$ alkynyl" defines straight and branched chain hydrocarbon radicals containing one or more triple bonds and optionally at least one double bond and having from 2 to 7 carbon atoms such as, for example, acetylenyl, 1-propynyl, 2-propynyl, 1-butynyl, 2-butynyl, 2-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like.

As used herein with respect to a substituting radical, and unless otherwise stated, the terms "arylalkyl", "arylalkenyl" and "heterocyclic-substituted alkyl" refer to an aliphatic saturated or ethylenically unsaturated hydrocarbon monovalent radical (preferably a $C_{1-7}$ alkyl or $C_{2-7}$ alkenyl radical such as defined above) onto which an aryl or heterocyclic radical (such as defined above) is already bonded via a carbon atom, and wherein the said aliphatic radical and/or the said aryl or heterocyclic radical may be optionally substituted with one or more substituents independently selected from the group consisting of halogen, amino, hydroxyl, sulfhydryl, $C_{1-7}$ alkyl, $C_{1-7}$ alkoxy, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-tert-butylbenzyl, phenylpropyl, 1-naphthylmethyl, phenylethyl, 1-amino-2-phenylethyl, 1-amino-2-[4-hydroxy-phenyl]ethyl, 1-amino-2-[indol-2-yl]ethyl, styryl, pyridylmethyl (including all isomers thereof), pyridylethyl, 2-(2-pyridyl)isopropyl, oxazolylbutyl, 2-thienylmethyl, pyrrolylethyl, morpholinylethyl, imidazol-1-yl-ethyl, benzodioxolylmethyl and 2-furylmethyl.

As used herein with respect to a substituting radical, and unless otherwise stated, the terms "alkylaryl" and "alkyl-substituted heterocyclic" refer to an aryl or, respectively, heterocyclic radical (such as defined above) onto which are bonded one or more aliphatic saturated or unsaturated hydrocarbon monovalent radicals, preferably one or more $C_{1-7}$ alkyl, $C_{2-7}$ alkenyl or $C_{3-10}$ cycloalkyl radicals as defined above such as, but not limited to, o-toluyl, m-toluyl, p-toluyl, 2,3-xylyl, 2,4-xylyl, 3,4-xylyl, o-cumenyl, m-cumenyl, p-cumenyl, o-cymenyl, m-cymenyl, p-cymenyl, mesityl, tert-butylphenyl, lutidinyl (i.e. dimethylpyridyl), 2-methylaziridinyl, methylbenzimidazolyl, methylbenzofuranyl, methylbenzothiazolyl, methylbenzotriazolyl, methylbenzoxazolyl and methylbenzselenazolyl.

As used herein with respect to a substituting radical, and unless otherwise stated, the term "alkoxyaryl" refers to an aryl radical (such as defined above) onto which is (are) bonded one or more $C_{1-7}$ alkoxy radicals as defined above, preferably one or more methoxy radicals, such as, but not limited to, 2-methoxyphenyl, 3-methoxyphenyl, 4-methoxyphenyl, 3,4-dimethoxyphenyl, 2,4,6-trimethoxyphenyl, methoxynaphthyl and the like.

As used herein with respect to a substituting radical, and unless otherwise stated, the terms "alkylamino", "cycloalkylamino", "alkenylamino", "cyclo-alkenylamino", "arylamino", "arylalkylamino", "heterocyclic-substituted alkylamino", "heterocyclic-substituted arylamino", "heterocyclic amino", "hydroxy-alkylamino", "mercapto-alkylamino" and "alkynylamino" mean that respectively one (thus monosubstituted amino) or even two (thus disubstituted amino) $C_{1-7}$ alkyl, $C_{3-10}$ cycloalkyl, $C_{2-7}$ alkenyl, $C_{3-10}$ cycloalkenyl, aryl, arylalkyl, heterocyclic-substituted alkyl, heterocyclic-substituted aryl, heterocyclic (provided in this case the nitrogen atom is attached to a carbon atom of the heterocyclic ring), mono- or polyhydroxy $C_{1-7}$ alkyl, mono- or polymercapto $C_{1-7}$ alkyl, or $C_{2-7}$ alkynyl radical(s) (each of them as defined herein, respectively, and including the presence of optional substituents independently selected from the group consisting of halogen, amino, hydroxyl, sulfhydryl, $C_{1-7}$ alkyl, $C_{1-7}$ alkoxy, trifluoromethyl and nitro) is/are attached to a nitrogen atom through a single bond such as, but not limited to, anilino, 2-bromoanilino, 4-bromoanilino, 2-chloroanilino, 3-chloroanilino, 4-chloroanilino, 3-chloro-4-methoxyanilino, 5-chloro-2-methoxy-anilino, 2,3-dimethylanilino, 2,4-dimethylanilino, 2,5-dimethylanilino, 2,6-dimethylanilino, 3,4-dimethylanilino, 2-fluoroanilino, 3-fluoroanilino, 4-fluoro-anilino, 3-fluoro-2-methoxyanilino, 3-fluoro-4-methoxyanilino, 2-fluoro-4-methyl-anilino, 2-fluoro-5-methylanilino, 3-fluoro-2-methylanilino, 3-fluoro-4-methylanilino, 4-fluoro-2-methylanilino, 5-fluoro-2-methylanilino, 2-iodoanilino, 3-iodoanilino, 4-iodoanilino, 2-methoxy-5-methylanilino, 4-methoxy-2-methylanilino, 5-methoxy-2-methylanilino, 2-ethoxyanilino, 3-ethoxy-anilino, 4-ethoxyanilino, benzylamino, 2-methoxybenzylamino, 3-methoxybenzylamino, 4-methoxybenzylamino, 2-fluoro-benzylamino, 3-fluorobenzyl-amino, 4-fluorobenzylamino, 2-chlorobenzylamino, 3-chlorobenzylamino, 4-chlorobenzylamino, 2-aminobenzylamino, diphenylmethyl-amino, α-naphthylamino, methylamino, dimethylamino, ethylamino, diethylamino, diethanolamino, isopropylamino, propenylamino, n-butylamino, tert-butylamino, dibutylamino, 1,2-diaminopropyl, 1,3-diaminopropyl, 1,4-diaminobutyl, 1,5-diaminopentyl, 1,6-diaminohexyl, morpholinomethyl-amino, 4-morpholinoanilino, hydroxymethylamino, β-hydroxyethylamino, dicyclohexyl-amino and ethynylamino; this definition also includes mixed disubstituted amino radicals wherein the nitrogen atom is attached to two such radicals belonging to two different sub-sets of radicals, e.g. an alkyl radical and an alkenyl radical, or to two different radicals within the same sub-set of radicals, e.g. methylethylamino; among di-substituted amino radicals, symmetrically-substituted amino radicals are more easily accessible and thus usually preferred from a standpoint of ease of preparation.

As used herein with respect to a substituting radical, and unless otherwise stated, the terms "(thio)carboxylic acid ester", "(thio)carboxylic acid thioester" and "(thio)-carboxylic acid amide" refer to radicals wherein the carboxyl or thiocarboxyl group is bonded to the hydrocarbonyl residue of an alcohol, a thiol, a polyol, a phenol, a thiophenol, a primary or secondary amine, a polyamine, an amino-alcohol or ammonia, the said hydrocarbonyl residue being selected from the group consisting of alkyl, alkenyl, alkynyl, cycloalkyl, cycloalkenyl, aryl, arylalkyl, alkylaryl, alkylamino, cycloalkylamino, alkenylamino, cycloalkenylamino, arylamino, arylalkylamino, heterocyclic-substituted alkylamino, heterocyclic amino, heterocyclic-substituted arylamino, hydroxyalkylamino, mercaptoalkylamino or alkynylamino (such as above defined, respectively).

As used herein with respect to a substituting radical, and unless otherwise stated, the term "sulfonamido" refers to a radical represented by the formula —$NR_x$—$SO_2R_y$, wherein $R_x$ hydrogen or a cyclic or non-cyclic hydrocarbyl group and $R_y$ is a cyclic or non-cyclic hydrocarbyl group.

As used herein with respect to a substituting radical, and unless otherwise stated, the term "amino-acid" refers to a radical derived from a molecule having the chemical formula $H_2N$—CHR—COOH, wherein R is the side group of atoms characterising the amino-acid type; said molecule may be one of the 20 naturally-occurring amino-acids or any similar non naturally-occurring amino-acid.

As used herein and unless otherwise stated, the term "stereoisomer" refers to all possible different isomeric as well as conformational forms which the compounds of the invention may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a pteridine derivative of this invention with a suitable inorganic solvent (e.g. hydrates) or organic solvent such as, but not limited to, alcohols, ketones, esters, ethers, nitriles and the like.

DETAILED DESCRIPTION OF THE INVENTION

In a first aspect, the present invention relates to a group of novel 4,6-disubstituted and 2,4,6-trisubstituted pteridine derivatives. Without limitation, this group includes molecules selected from the group consisting of:
6-(2,6-dichlorophenyl)-4-ethoxypteridin-2-amine,
3-(2-amino-4-ethoxypteridin-6-yl)benzonitrile
4-ethoxy-6-(3-fluoro-4-methoxyphenyl)pteridin-2-amine
4-ethoxy-6-(4-(trifluoromethoxy)phenyl)pteridin-2-amine
6-(3,5-bis(trifluoromethyl)phenyl)-4-ethoxypteridin-2-amine
4-ethoxy-6-(4-(trifluoromethyl)phenyl)pteridin-2-amine
6-(4-chloro-3-fluorophenyl)-4-ethoxypteridin-2-amine
6-(3,5-dichlorophenyl)-4-ethoxypteridin-2-amine
6-(3,4-difluorophenyl)-4-ethoxypteridin-2-amine
4-ethoxy-6-(2-fluorophenyl)pteridin-2-amine
6-(2,6-difluorophenyl)-4-ethoxypteridin-2-amine
6-(3,5-difluorophenyl)-4-ethoxypteridin-2-amine
6-(2,3-difluorophenyl)-4-ethoxypteridin-2-amine
4-ethoxy-6-(3-fluorophenyl)pteridin-2-amine
dimethyl (4-(2-amino-4-ethoxypteridin-6-yl)phenyl)methylphosphonate
6-(2,4-difluorophenyl)-4-ethoxypteridin-2-amine
6-(3-chlorophenyl)-4-ethoxypteridin-2-amine
6-(2,4-bis(trifluoromethyl)phenyl)-4-ethoxypteridin-2-amine
4-ethoxy-6-(pyridin-3-yl)pteridin-2-amine
4-ethoxy-6-(1H-pyrazol-5-yl)pteridin-2-amine
4-ethoxy-6-(pyrimidin-5-yl)pteridin-2-amine
4-ethoxy-6-(2-fluoropyridin-3-yl)pteridin-2-amine
4-ethoxy-6-(thiophen-3-yl)pteridin-2-amine
4-ethoxy-6-(furan-3-yl)pteridin-2-amine
N-(4-(2-amino-4-ethoxypteridin-6-yl)phenyl)acetamide
6-(2,5-difluorophenyl)-4-ethoxypteridin-2-amine
6-(4-chlorophenyl)-4-ethoxypteridin-2-amine
4-ethoxy-6-(2-(trifluoromethyl)phenyl)pteridin-2-amine
4-ethoxy-6-(1H-indol-5-yl)pteridin-2-amine
4-ethoxy-6-(4-(methylsulfonyl)phenyl)pteridin-2-amine
4-ethoxy-6-(pyridin-4-yl)pteridin-2-amine
4-ethoxy-6-(1H-pyrazol-4-yl)pteridin-2-amine
4-ethoxy-6-(furan-2-yl)pteridin-2-amine
6-(2-chlorophenyl)-4-ethoxypteridin-2-amine
6-(2,3-dichlorophenyl)-4-ethoxypteridin-2-amine
6-(3-chloro-4-fluorophenyl)-4-ethoxypteridin-2-amine
6-(2-chloro-4-fluorophenyl)-4-ethoxypteridin-2-amine
4-ethoxy-6-(3-(trifluoromethyl)phenyl)pteridin-2-amine
4-ethoxy-6-(3-(trifluoromethoxy)phenyl)pteridin-2-amine
4-(2-amino-4-ethoxypteridin-6-yl)-N-methylbenzamide 4-(2-amino-4-ethoxypteridin-6-yl)-N-cyclopropylbenzamide
6-(4-(dimethylamino)phenyl)-4-ethoxypteridin-2-amine
4-ethoxy-6-(4-fluoro-2-methylphenyl)pteridin-2-amine
5-(2-amino-4-ethoxypteridin-6-yl)thiophene-2-carbonitrile
4-ethoxy-6-(2-(trifluoromethoxy)phenyl)pteridin-2-amine
4-ethoxy-6-(2,3,4-trifluorophenyl)pteridin-2-amine
6-(2-chloro-4-(trifluoromethyl)phenyl)-4-ethoxypteridin-2-amine
4-ethoxy-6-(2,4,6-trifluorophenyl)pteridin-2-amine
6-(5-chlorothiophen-2-yl)-4-ethoxypteridin-2-amine
2-(2-amino-4-ethoxypteridin-6-yl)phenol
6-(2,5-dichlorophenyl)-4-ethoxypteridin-2-amine
6-(3,5-dimethylphenyl)-4-ethoxypteridin-2-amine
4-ethoxy-6-(3-ethoxyphenyl)pteridin-2-amine
4-ethoxy-6-p-tolylpteridin-2-amine
6-(benzo[b]thiophen-2-yl)-4-ethoxypteridin-2-amine
4-ethoxy-6-(2-ethoxyphenyl)pteridin-2-amine
4-(2-amino-4-ethoxypteridin-6-yl)phenol
6-(2,4-dichlorophenyl)-4-ethoxypteridin-2-amine
4-ethoxy-6-(2,4,5-trifluorophenyl)pteridin-2-amine
4-ethoxy-6-(2-methylphenyl)pteridin-2-amine
1-(4-(2-amino-4-ethoxypteridin-6-yl)phenyl)pyrrolidin-2-one
5-(2-amino-4-ethoxypteridin-6-yl)indolin-2-one
4-ethoxy-6-(6-methoxypyridin-3-yl)pteridin-2-amine
4-ethoxy-6-(isoxazol-4-yl)pteridin-2-amine
4-ethoxy-6-(5-fluoro-2-methoxyphenyl)pteridin-2-amine
methyl 4-(2-amino-4-ethoxypteridin-6-yl)phenylcarbamate
6-(benzofuran-2-yl)-4-ethoxypteridin-2-amine
4-ethoxy-6-morpholinopteridin-2-amine
6-(4-aminophenyl)-4-ethoxypteridin-2-amine
4-ethoxy-6-(3-methylpyridin-4-yl)pteridin-2-amine
4-ethoxy-6-(2-methoxypyridin-4-yl)pteridin-2-amine
4-ethoxy-6-(2-methylpyridin-4-yl)pteridin-2-amine
4-ethoxy-6-(pyridin-2-yl)pteridin-2-amine
6-(2-fluorophenyl)-4-morpholinopteridin-2-amine
6-(2-chlorophenyl)-4-morpholinopteridin-2-amine
4-morpholino-6-(2-(trifluoromethyl)phenyl)pteridin-2-amine
6-(2-methoxyphenyl)-4-morpholinopteridin-2-amine
6-(3-fluorophenyl)-4-morpholinopteridin-2-amine
6-(3-chlorophenyl)-4-morpholinopteridin-2-amine
4-morpholino-6-(3-(trifluoromethyl)phenyl)pteridin-2-amine
4-morpholino-6-(3-(trifluoromethoxy)phenyl)pteridin-2-amine
3-(2-amino-4-morpholinopteridin-6-yl)benzonitrile
4-morpholino-6-(4-(trifluoromethoxy)phenyl)pteridin-2-amine
4-(2-amino-4-morpholinopteridin-6-yl)benzonitrile
4-morpholino-6-(4-(morpholinomethyl)phenyl)pteridin-2-amine
6-(2,3-difluorophenyl)-4-morpholinopteridin-2-amine
6-(2,3-dichlorophenyl)-4-morpholinopteridin-2-amine
6-(2-chloro-4-fluorophenyl)-4-morpholinopteridin-2-amine
6-(2,4-bis(trifluoromethyl)phenyl)-4-morpholinopteridin-2-amine
6-(2,4-difluorophenyl)-4-morpholinopteridin-2-amine
6-(2,6-dichlorophenyl)-4-morpholinopteridin-2-amine
6-(3,5-bis(trifluoromethyl)phenyl)-4-morpholinopteridin-2-amine
6-(4-chloro-3-fluorophenyl)-4-morpholinopteridin-2-amine
6-(3,5-difluorophenyl)-4-morpholinopteridin-2-amine
6-(3,5-dichlorophenyl)-4-morpholinopteridin-2-amine
dimethyl (4-(2-amino-4-morpholinopteridin-6-yl)phenyl)methylphosphonate
6-(2,6-difluorophenyl)-4-morpholinopteridin-2-amine
6-(3,4-dichlorophenyl)-4-morpholinopteridin-2-amine
6-(3-chloro-4-fluorophenyl)-4-morpholinopteridin-2-amine
4-morpholino-6-(4-(trifluoromethyl)phenyl)pteridin-2-amine
6-(4-(methylsulfonyl)phenyl)-4-morpholinopteridin-2-amine
6-(1H-indol-5-yl)-4-morpholinopteridin-2-amine
4-morpholino-6-(pyrimidin-5-yl)pteridin-2-amine
4-morpholino-6-(pyridin-3-yl)pteridin-2-amine
6-(2-fluoropyridin-3-yl)-4-morpholinopteridin-2-amine
4-morpholino-6-(thiophen-3-yl)pteridin-2-amine
6-(furan-3-yl)-4-morpholinopteridin-2-amine
4-morpholino-6-(1H-pyrazol-5-yl)pteridin-2-amine
6-(2,3-difluorophenyl)-4-morpholinopteridin-2-amine
4-(2-amino-4-morpholinopteridin-6-yl)-N-methylbenzamide
4-(2-amino-4-morpholinopteridin-6-yl)-N-cyclopropylbenzamide
6-(2,5-difluorophenyl)-4-morpholinopteridin-2-amine
4-morpholino-6-(pyridin-4-yl)pteridin-2-amine
4-morpholino-6-(1H-pyrazol-4-yl)pteridin-2-amine
6-(4-(dimethylamino)phenyl)-4-morpholinopteridin-2-amine
6-(4-fluoro-2-methylphenyl)-4-morpholinopteridin-2-amine
6-(2-chloro-4-(trifluoromethyl)phenyl)-4-morpholinopteridin-2-amine
5-(2-amino-4-morpholinopteridin-6-yl)thiophene-2-carbonitrile
6-(benzo[b]thiophen-2-yl)-4-morpholinopteridin-2-amine
2-(2-amino-4-morpholinopteridin-6-yl)phenol
6-(2-ethoxyphenyl)-4-morpholinopteridin-2-amine
6-(3-ethoxyphenyl)-4-morpholinopteridin-2-amine
6-(5-chlorothiophen-2-yl)-morpholinopteridin-2-amine
1-(4-(2-amino-4-morpholinopteridin-6-yl)phenyl)pyrrolidin-2-one
methyl 4-(2-amino-4-morpholinopteridin-6-yl)phenylcarbamate
6-(6-methoxypyridin-3-yl)-4-morpholinopteridin-2-amine
6-(isoxazol-4-yl)-4-morpholinopteridin-2-amine
6-(2-methylphenyl)-4-morpholinopteridin-2-amine
6-(benzofuran-2-yl)-4-morpholinopteridin-2-amine
6-(5-fluoro-2-methoxyphenyl)-4-morpholinopteridin-2-amine
4-morpholino-6-(3,4,5-trifluorophenyl)pteridin-2-amine
5-(2-amino-4-morpholinopteridin-6-yl)indolin-2-one
N-(4-(2-amino-4-morpholinopteridin-6-yl)phenyl)isobutyramide
N-(4-(2-amino-4-morpholinopteridin-6-yl)phenyl)pivalamide
(S)-tert-butyl 1-(4-(2-amino-4-morpholinopteridin-6-yl)phenylamino)-3-hydroxy-1-oxopropan-2-yl-carbamate
(S)-tert-butyl 1-(4-(2-amino-4-morpholinopteridin-6-yl)phenylamino)-1-oxopropan-2-yl-carbamate
N-[6-(4-amino-phenyl)-4-morpholin-4-yl-pteridin-2-yl]acetamide
cyclopropane carboxylic acid[4-(2-amino-4-morpholin-4-yl-pteridin-6-yl)-phenyl]-amide
6-(2,3-difluoro-phenyl)-pteridine-2,4-diamine
(S)-2-amino-N-(4-(2-amino-4-morpholinopteridin-6-yl)phenyl)-3-hydroxypropanamide
(S)-2-amino-N-(4-(2-amino-4-morpholinopteridin-6-yl)phenyl)propanamide
6-(4-fluoro-phenyl)-4-methoxy-pteridin-2-ylamine
6-(4-fluoro-phenyl)-4-isopropoxy-pteridin-2-ylamine
6-(4-fluoro-phenyl)-4-(2-methoxy-ethoxy)-pteridin-2-ylamine 4-butoxy-6-(4-fluoro-phenyl)-pteridin-2-ylamine
6-(4-fluoro-phenyl)-4-(2,2,2-trifluoro-ethoxy)-pteridin-2-ylamine
4-[2-amino-6-(4-fluoro-phenyl)-pteridin-4-yloxy]-2-methyl-butan-2-ol
6-(4-fluoro-phenyl)-4-(2-morpholin-4-yl-ethoxy)-pteridin-2-ylamine
6-(4-fluoro-phenyl)-4-(3-morpholin-4-yl-propoxy)-pteridin-2-ylamine
4-cyclopropylmethoxy-6-(4-fluoro-phenyl)-pteridin-2-ylamine
4-cyclobutylmethoxy-6-(4-fluoro-phenyl)-pteridin-2-ylamine
6-(4-fluoro-phenyl)-4-propoxy-pteridin-2-ylamine
4-sec-butoxy-6-(4-fluoro-phenyl)-pteridin-2-ylamine
6-(4-fluoro-phenyl)-4-(tetrahydro-furan-3-yloxy)-pteridin-2-ylamine
6-(4-fluoro-phenyl)-4-isobutoxy-pteridin-2-ylamine
4-benzyloxy-6-(4-fluoro-phenyl)-pteridin-2-ylamine
4-ethylsulfanyl-6-(4-fluoro-phenyl)-pteridin-2-ylamine
4-amino-6-(4-fluoro-phenyl)-pteridine-2,4-diamine
6-(4-fluoro-phenyl)-4-piperidin-1-yl-pteridin-2-ylamine
N-4-cyclopropyl-6-(4-fluoro-phenyl)-pteridine-2,4-diamine
4-(2,6-dimethyl-morpholin-4-yl)-6-(4-fluoro-phenyl)-pteridin-2-ylamine
N-4-cyclohexyl-6-(4-fluoro-phenyl)-pteridine-2,4-diamine
N-4-benzyl-6-(4-fluoro-phenyl)-pteridine-2,4-diamine
N-4-(3-methyl-benzyl)-6-(4-fluoro-phenyl)-pteridine-2,4-diamine
N-4-(3-fluoro-benzyl)-6-(4-fluoro-phenyl)-pteridine-2,4-diamine
6-(4-fluoro-phenyl)-4-(4-methyl-piperazin-1-yl)-pteridin-2-ylamine
6-(4-fluoro-phenyl)-4-piperazin-1-yl-pteridin-2-ylamine
N-4-cyclopropylmethyl-6-(4-fluoro-phenyl)-pteridine-2,4-diamine
6-(4-fluoro-phenyl)-4-pyrrolidin-1-yl-pteridin-2-ylamine
4-ethoxy-6-(4-fluoro-phenyl)-pteridine
4-isopropoxy-6-(4-fluoro-phenyl)-pteridine
4-(2-methoxy-ethoxy)-6-(4-fluoro-phenyl)-pteridine
[6-(4-Fluoro-phenyl)-pteridin-4-yl]-(4-methyl-cyclohexyl)-amine,
[6-(4-Fluoro-phenyl)-pteridin-4-yl]-(4-methyl-cyclohexyl)-amine,
6-(4-fluoro-phenyl)-4-morpholin-4-yl-pteridine, and
4-ethylsulfanyl-6-(4-fluoro-phenyl)-pteridine,
and/or a pharmaceutically acceptable addition salt thereof and/or a stereoisomer thereof and/or a mono- or a di-N-oxide thereof and/or a solvate thereof and/or a pro-drug form thereof.

Each of the substituents present on positions 2, 4 and/or 6 of the pteridine scaffold of these molecules belongs to a broader class of substituents being defined in the section "Definitions" herein-above. It should be understood that some alternative molecules differing from the molecules of the above list by replacing such a substituent with another similar substituent of the same class, e.g. replacing 4-fluorophenyl with 4-chlorophenyl on position 6, may result in a very similar utility in medical treatment, therefore said alternative molecules are also within the framework of the present invention.

In a second aspect, the present invention relates to a group of pteridine derivative represented by the structural formula:

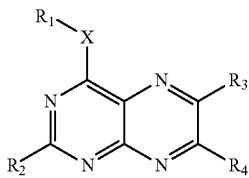

wherein X represents an oxygen atom or a group with the formula $S(O)_m$ wherein m is an integer from 0 to 2, or a group with the formula NZ and wherein:

$R_1$ is a group selected from the group consisting of $C_{1-7}$ alkyl, $C_{2-7}$ alkenyl, $C_{2-7}$ alkynyl, $C_{3-10}$ cycloalkyl, $C_{3-10}$ cycloalkenyl, aryl, alkylaryl, arylalkyl, heterocyclic, heterocyclic-substituted alkyl and alkyl-substituted heterocyclic, each of said groups being optionally substituted with one or more substituents independently selected from the group consisting of halogen, $C_{1-4}$ alkyl, $C_{1-4}$ alkoxy, $C_{2-7}$ alkenyl, $C_{2-7}$ alkynyl, halo $C_{1-4}$ alkyl, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxyl, sulfhydryl, nitro, hydroxylamino, mercaptoamino, cyano, carboxylic acid or esters or thioesters or amides or thioamides or halides or anhydrides thereof, thiocarboxylic acid or esters or thioesters or amides or thioamides or halides or anhydrides thereof, carbamoyl, thiocarbamoyl, ureido, thioureido, amino, alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino and phenyl-hydrazino; or $R_1$ is a carboxyalkyl, carboxyaryl, thiocarboxyaryl or thiocarboxyalkyl group;

Z is a group independently defined as $R_1$ or Z is hydrogen or the group NZ together with $R_1$ is either hydroxylamino or an optionally substituted heterocyclic group containing at least one nitrogen atom;

$R_2$ is selected from the group consisting of amino; alkanoylamino; thioalkanoylamino; carbamoyl; thiocarbamoyl, ureido; thio-ureido, sulfonamido; hydroxylamino; alkoxyamino; thioalkylamino; mercaptoamino, hydrazino; alkylhydrazino; phenylhydrazino; optionally substituted heterocyclic radicals; $C_{3-7}$ alkylamino; arylamino; arylalkylamino; cycloalkylamino; alkenylamino; cycloalkenylamino; heterocyclic amino; hydroxyalkylamino; mercaptoalkylamino; $C_{1-7}$ alkoxy; $C_{3-10}$ cycloalkoxy; thio $C_{1-7}$ alkyl; arylsulfoxide; arylsulfone; heterocyclic sulfoxide; heterocyclic sulfone; thio $C_{3-10}$ cycloalkyl; aryloxy; arylthio; arylalkyloxy; arylalkylthio; oxyheterocyclic and thioheterocyclic radicals;

$R_4$ is hydrogen; and $R_3$ is aryl substituted with one or more substituents independently selected from the group consisting of aryl wherein said aryl is optionally substituted with arylcarbonyl; (O,O-dialkylphosphonyl)-alkyl; alkanoyl; halo-$C_{1-7}$ alkoxy; hydroxy-$C_{1-7}$alkoxy; hydroxy-$C_{1-7}$ alkyl; alkylamino $C_{1-7}$ alkyl; ω-carboxyalkanoylamino, mono-($C_{3-7}$ cycloalkyl)aminocarbonyl, cycloalkyl)aminocarbonyl, mono-($C_{1-7}$ alkyl)aminocarbonyl, mono-(ω-dimethylamino-$C_{1-7}$ alkyl)aminocarbonyl, di-($C_{1-7}$ alkyl)aminocarbonyl, mono-(hydroxy-$C_{1-7}$alkyl)aminocarbonyl, formylamino, sulfamoyl ($SO_2NH_2$), arylamino-$C_{1-7}$ alkyl, $C_{1-7}$ alkylsulfonyl, heterocyclyl-carbonyl, heterocyclyl-$C_{1-7}$ alkyl and heterocyclyl, wherein said heterocyclyl is optionally substituted with $C_{3-7}$ alkenyloxycarbonyl, $C_{1-7}$ alkyl or $C_{1-7}$ alkyloxycarbonyl; or $R_3$ is a fused benzo-$C_{5-8}$ cycloalkyl optionally substituted with oxo; or $R_3$ is heterocyclyl substituted with one or more substituents independently selected from the group consisting of acylamino, $C_{1-7}$ alkylsulfonyl, arylsulfonyl, heterocyclyl-$C_{1-7}$ alkyl, heterocyclyl-$C_{1-7}$ alkylamino, aryl and heterocyclyl, wherein said heterocyclyl is optionally substituted with $C_{1-7}$ alkyl, arylsulfonyl or (di-$C_{1-7}$ alkylamino)-$C_{1-7}$ alkoxy, or said heterocyclyl is non-aromatic and includes a nitrogen atom substituted with heterocyclyl-$C_{1-7}$ alkyl or a carboxylic acid or a $C_{1-7}$ alkyl ester thereof, and/or a pharmaceutically acceptable addition salt thereof and/or a stereo-isomer thereof and/or a mono- or a di-N-oxide thereof and/or a solvate thereof and/or a pro-drug form thereof.

A general description of methods for the synthesis of the compounds of the present invention has been provided in WO2005/021003, in particular in FIGS. 1 to 5 thereof and the corresponding description. Most of these methods make use of a boronic acid, or a pinacol ester thereof, for introducing a substituent at position 6 of the pteridine core structure. Processes for preparing such organic boronic acid derivatives have been described for example in EP-B-1,019,414. For the purpose of the present invention, suitable aryl-boronic acids include, but are not limited to, the following commercially available materials wherein the aryl group is 3-acetamidophenyl, 4-acetamidophenyl, 4-acetylphenyl, 3-acetylphenyl, 2-acetylphenyl, 5-acetyl-2-chlorophenyl, 4-acetyl-3-fluorophenyl, 5-acetyl-2-fluorophenyl, 4-(4'-allyloxycarbonylpiperazino)phenyl, 3-aminocarbonylphenyl, 4-aminocarbonylphenyl, 2-amino-5-chlorophenyl, 4-amino-3-methoxyphenyl, 3-aminophenyl, 2-amino-4-methylphenyl, 2-amino-5-methylphenyl, 4-amino-2-methylphenyl, 5-amino-2-methylphenyl, 4-amino-3-nitrophenyl, 3-aminophenyl, 2-aminophenyl, 4-aminophenyl, 4-benzyloxyphenyl, 3-benzyloxyphenyl, 2-benzyloxyphenyl, 4-benzyloxy-2-fluorophenyl, 4-benzyloxy-3-fluorophenyl, 3-benzyloxy-4-methoxyphenyl, 4-biphenyl, 3,5-bis(trifluoromethyl)benzene, 4-bromophenyl, 3-bromophenyl, 4-bromo-2,5-dimethylphenyl, 2-bromo-5-fluorophenyl, 2-bromo-6-fluorophenyl, 4-n-butylphenyl, 4-isobutylphenyl, 4-carboxyphenyl, 3-carboxyphenyl, 2-carboxyphenyl, 2-carboxy-5-fluorophenyl, 4-carboxy-3-fluorophenyl, 4-carboxy-2-chlorophenyl, 5-carboxy-2-chlorophenyl, 4-carboxy-3-chlorophenyl, 3-carboxyphenyl, 3-(3-carboxypropionyl-amino)phenyl, 4-(3-carboxypropionylamino)phenyl, 2-chloro-5-formylphenyl, 3-chloro-4-fluorophenyl, 2-chloro-4-fluorophenyl, 4-chloro-2-fluorophenyl, 3-chloro-4-hydroxy-5-methoxyphenyl, 2-chloro-5-hydroxymethylphenyl, 3-chloro-5-methoxyphenyl, 2-chloro-4-methylphenyl, 2-chloro-5-methylphenyl, 2-chloro-5-trifluoromethoxyphenyl, 3-chloro-5-trifluoromethylphenyl, 4-chloro-2-trifluoromethylphenyl, 4-chlorophenyl, 3-chlorophenyl, 2-chlorophenyl, 4-cyanomethoxyphenyl, 3-cyanomethoxyphenyl, 2-cyanomethoxyphenyl, 4-cyanophenyl, 3-cyanophenyl, 2-cyanophenyl, 3,5-dibromophenyl, 3-(N-cyclopropylamino-carbonyl)phenyl, 2,6-dichlorophenyl, 3,4-dichlorophenyl, 2,4-dichlorophenyl, 2,3-dichlorophenyl, 3,5-dichlorophenyl, 3-(N,N-diethylaminocarbonyl)phenyl, 3,5-difluorophenyl, 3,5-difluoro-2-methoxyphenyl, 3,4-difluorophenyl, 2,6-difluorophenyl, 2,5-difluorophenyl, 2,4-difluorophenyl, 2,3-difluorophenyl, 4-(N,N-dimethylamino)phenyl, 3-(N,N-dimethylamino)-phenyl, 2-(N,N-dimethylamino)phenyl, 3-[(N,N-dimethylaminocarbonyl)phenyl, dimethylamino)ethylaminocarbonyl]phenyl, 4-[(N',N'-dimethylamino)ethyl-aminocarbonyl]-phenyl, 3,5-dimethylphenyl, 3,4-dimethylphenyl, 2,6-dimethylphenyl, 2,6-dimethoxyphenyl, 2,5-dimethoxyphenyl, 2,4-dimethoxyphenyl, 3-[1,3]dioxolan-2-ylmethoxyphenyl, 4-ethoxyphenyl, 2-ethoxyphenyl, 3-(ethoxycarbonyl)methoxyphenyl, 4-(ethoxycarbonyl)-methoxyphenyl, 4-ethoxycarbonylphenyl, 3-ethoxycarbonylphenyl, 2-ethoxycarbonylphenyl, 4-(3-ethoxycarbonylpiperidino)carboxamidophenyl, 4-ethylphenyl, 4-fluorophenyl, 3-fluorophenyl, 2-fluorophenyl, 3-fluoro-4-formylphenyl, 4-fluoro-3-formylphenyl, 4-fluoro-2-methylphenyl, 2-fluoro-5-methylphenyl, 2-fluoro-5-methoxyphenyl, 3-fluoro-4-methoxyphenyl, 5-fluoro-2-methoxycarbonylphenyl, 2-fluoro-4-trifluoromethylphenyl, 2-formylaminophenyl, 3-formylaminophenyl, 4-formylaminophenyl, 2-formyl-5-methoxyphenyl, 3-formyl-4-methoxyphenyl, 5-formyl-2-methoxyphenyl, 2-formyl-5-methylphenyl, 4-formylphenyl, 3-formylphenyl, 2-formylphenyl, 4-hydroxy-3,5-dimethylphenyl, 3-(2-hydroxyethyl)-aminocarbonylphenyl, 4-(2-hydroxyethyl)aminocarbonyl-phenyl, 3-hydroxy-4-methoxycarbonylphenyl, 4-hydroxy-3-methoxyphenyl, 4-(hydroxymethyl)phenyl, 3-(hydroxymethyl)phenyl, 4-hydroxy-3-nitrophenyl, 4-hydroxyphenyl, 3-hydroxyphenyl, 2-hydroxyphenyl, 4-isopropoxyphenyl, 4-(4-isopropylpiperazinyl)phenyl, 4-isopropylphenyl, 4-methanesulfonamido-phenyl, 3-methanesulfonamidophenyl, 2-methanesulfonamido-phenyl, 4-methanesulfonylphenyl, 2-methoxy-5-formylphenyl, 5-methoxy-2-formylphenyl, 4-methoxy-2-formylphenyl, 4-methoxycarbonylphenyl, 3-methoxycarbonylphenyl, 2-methoxycarbonylphenyl, 3-methoxy-4-methoxycarbonylphenyl, 2-methoxy-5-methoxycarbonylphenyl, 4-methoxy-3-nitrophenyl, 4-methoxyphenyl, 3-methoxyphenyl, 2-methoxyphenyl, 2-methoxy-5-methylphenyl, 4-N-methylcarboxamidophenyl, 4-methyl-phenyl, 3-methylphenyl, 2-methylphenyl, 4-(N-methylamino)phenyl, 3-(4-methyl-piperazine-1-carbonyl)phenyl, 4-(4-methylpiperazine-1-carbonyl)phenyl, 4-(methylthio)-phenyl, 3-(methylthio)phenyl, 2-(methylthio)phenyl, 4-morpholinophenyl, 4-(morpholino-carbonyl)phenyl, 2-morpholinomethyl)phenyl, 4-nitrophenyl, 3-nitrophenyl, 2-nitrophenyl, 4-phenoxyphenyl, 4-(N-phenylaminomethyl)phenyl, 4-(phenylcarbonyl)phenyl, 4-(piperazine-1-carbonyl)phenyl, 4-piperazinylphenyl, 3-succinamidophenyl, 4-succinamidophenyl, sulfamoylphenyl, 2-(toluene-4-sulfonamido)phenyl, 3-(toluene-4-sulfonamido)phenyl, 4-(toluene-4-sulfonamido)phenyl, 4-(tert-butoxycarbonylamino)-3-methoxyphenyl, 2-(tert-butoxycarbonyl)phenyl, 3-(tert-butoxycarbonyl)phenyl, 4-(tert-butoxycarbonyl)phenyl, 4-tert-butylphenyl, 4-(tetrahydro-2H-pyran-2-yloxy)phenyl, 4-(2-thienyl)phenyl, 4-trifluoromethoxyphenyl, 4-(trimethylammonium)methylphenyl, 2,4,6-trimethylphenyl, 3,4,5-trifluorophenyl, 2,3,4-trifluorophenyl, 3-trifluoromethylphenyl, 4-trifluoromethoxyphenyl, 3-trifluoromethoxyphenyl, 2-trifluoromethylphenyl, 3-trifluoromethylphenyl, 4-trifluoromethylphenyl, 3,4,5-trimethoxyphenyl, 4-vinylphenyl, 6-benzyloxy-naphth-2-yl, naphth-1-yl, naphth-2-yl, 4-(2-hydroxyethoxy)phenyl, 4'-benzoyl[1,1'-biphenyl]-4-yl, oxoindan-5-yl, (O,O-dimethylphosphonyl)methyl or 1-biphenylyl.

For the purpose of making the compounds of the present invention, suitable heterocyclic-boronic acids or pinacol esters thereof include, but are not limited to, the following commercially available materials wherein the heterocyclic group is 3,4-methylenedioxyphenyl (benzodioxolyl), 2-acetamidopyridin-5-yl, 2-aminopyridin-5-yl, 2-aminopyrimidin-5-yl, 1,4-benzodioxan-6-yl, 2-benzothienyl, 1-benzothien-3-yl, 1-benzothien-2-yl, 2-benzyloxypyridin-5-yl, 1-benzyl-1H-pyrazol-4-yl, 2-bromo-3-chloropyridin-4-yl, 5-bromo-2,3-dihydrobenzo[b]furan-7-yl, 2-bromo-3-methylpyridin-5-yl, 3-bromopyridin-5-yl, 2-bromopyridin-5-yl, 5-bromothien-2-yl, 2-chloro-6-isopropylpyridin-3-yl, 2-chloro-3-methylpyridin-5-yl, 2-[4-(4-chlorophenylsulfonyl)piperazin-1-yl]pyridin-5-yl, 2-chloropyrid-4-yl, 2-chloropyrid-5-yl, 5-chlorothien-2-yl, dibenzo[b,d]furan-4-yl, 2-chloro-3-fluoropyridin-4-yl, dibenzo[b,d]thien-4-yl, 3,4-dihydro-2H-1,5-benzodioxepin-7-yl, 3,6-dihydro-2H-pyridine-1-tert-butoxycarbonyl, 2,5-dibromo-3-pyridinyl, 2,6-dichloro-pyridin-3-yl, 2,3-dihydro-1-benzofuran-5-yl, 2,6-dimethoxypyridin-5-yl, 2,6-dimethoxypyridin-3-yl, 2,4-dimethoxypyrimidin-5-yl, 3,5-dimethylisoxazol-4-yl, 2-(3-N,N-dimethylaminopropoxy)pyridin-5-yl, 3,5-dimethylpyrazol-4-yl 1-[1,3]dioxolan-2-ylmethyl-1H-pyrazol-4-yl, 2,4-dioxo-1,2,3,4-tetrahydro-5-pyrimidinyl, 2,4-di(tert-butoxy)pyrimidin-5-yl, 2-ethoxypyridin-3-yl, 2-fluoro-3-methylpyridin-5-yl, 2-fluoropyridin-3-yl, 2-fluoropyridin-5-yl, 5-formyl-2-furyl, 5-formylthien-2-yl, furan-3-yl, furan-2-yl, 2-hydroxypyridin-5-yl, 5-indolyl, 1-isobutyl-1H-pyrazol-4-yl, isoquinolin-4-yl, 2-methoxypyridin-3-yl, 2-methoxypyrimidin-5-yl, 5-methyl-1-benzothiophen-2-yl, 1-(3-methylbutyl)-1H-pyrazol-4-yl, 5-methylfuran-2-yl, 1-methylindol-5-yl, 5-methyl-3-phenyl-4-isoxazolyl, 5-(methylthio)thien-2-yl, 2-(4-methylpiperazinyl)pyridin-4-yl, 2-(4-methylpiperazinyl)pyridin-5-yl, 1-methyl-1H-pyrazol-4-yl, 3-methylpyridin-2-yl, 5-methylpyridin-2-yl, 5-methylpyridin-3-yl, 4-methylthien-2-yl, 5-methylthien-2-yl, 2-methoxypyridin-5-yl, 2-(2-morpholinoethylamino)-pyridin-5-yl, 2-(2-morpholinoethyl)-1H-pyrazol-4-yl, 2-(morpholin-1-yl)-pyridin-5-yl, 1-(phenylsulfonyl)-1H-indol-3-yl, 5-phenyl-2-thienyl, 2-(piperazin-1-yl)-pyridin-5-yl, 2-(piperazin-1-yl)-pyridin-4-yl, 1-propyl-1H-pyrazol-4-yl, pyrazol-4-yl, pyridin-4-yl, pyridin-3-yl, pyrimidin-5-yl, 4-phenoxathiinyl, quinolin-8-yl, quinolin-3-yl, 2-(4-tert-butoxycarbonylpiperazinyl)-pyrid-4-yl, 1-tert-butoxycarbonyl-1H-pyrazol-4-yl, 1-tert-butoxycarbonyl-2-pyrrolyl, 1-(tert-butoxycarbonyl)-5-bromo-1H-indol-2-yl, 1-(tert-butoxycarbonyl)-1H-indol-5-yl, 1-(tert-butoxycarbonyl)-5-methoxy-1H-indol-2-yl, 1-thianthrenylthien-3-yl, thien-3-yl, thien-2-yl or 1,3,5-trimethyl-1H-pyrazol-4-yl.

Stereoisomers of the 4,6-disubstituted and 2,4,6-trisubstituted pteridine derivatives of the present invention may be formed by using reactants in their single enantiomeric form wherever possible in the manufacturing process, or by resolving a mixture of stereoisomers by conventional methods. One such method is liquid chromatography using one or more suitable chiral stationary phases including, for example, polysaccharides, in particular cellulose or amylose derivatives. Commercially available, but non limiting, suitable polysaccharide-based chiral stationary phases are ChiralCel™ CA, OA, OB, OC, OD, OF, OG, OJ and OK, and Chiralpak™ AD, AS, OP(+) and OT(+). Appropriate eluents or mobile phases for use in combination with said polysaccharide-based chiral stationary phases are hydrocarbons such as hexane and the like, optionally admixed with an alcohol such as ethanol, isopropanol and the like. The above mixture of enantiomers may alternatively be separated by making use of microbial resolution or by resolving the diastereoisomeric salts formed with chiral acids such as mandelic acid, camphorsulfonic acid, tartaric acid, lactic acid and the like or with chiral bases such as brucine and the like. The resolving agent may be cleaved from the separated diastereoisomers, e.g. by treatment with acids or bases, in order to generate the pure enantiomers of the compounds of the invention. Conventional resolution methods were compiled e.g. by Jaques et al. in "Enantiomers, Racemates and Resolution" (Wiley Interscience, 1981).

As noted above, one particular embodiment of this invention includes the various precursors or "pro-drug" forms of the 4,6-disubstituted and 2,4,6-trisubstituted pteridine derivatives of the present invention. It may be desirable to formulate the compounds of the present invention in the form of a chemical species which itself is not significantly biologically-active but which, when delivered to the body of a human being or higher mammal, will undergo a chemical reaction catalyzed by the normal function of the body, inter alia, enzymes present in the stomach or in blood serum, said chemical reaction having the effect of releasing a compound as defined herein. The term "pro-drug" thus relates to these species which are converted in vivo into the active pharmaceutical ingredient.

The pro-drugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used.

For the purpose of the present invention the term "therapeutically suitable pro-drug" is defined herein as a compound modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome.

In another aspect, the present invention provides the use of 4,6-disubstituted and 2,4,6-trisubstituted pteridine derivatives as defined herein-above for the manufacture of a medicament for treating or preventing a viral infection, and the corresponding method of treatment of a viral infection by administering an effective amount of such a 4,6-disubstituted or 2,4,6-trisubstituted pteridine derivative to a patient in need thereof. In one embodiment, said viral infection may be an infection caused by a virus being a member of the Flaviviridae family. The Flaviviridae family is a family of positive-strand RNA viruses which includes the following genera:

Genus *Flavivirus* (type species include Yellow fever virus, West Nile virus and Dengue Fever),
    Genus *Hepacivirus* (type species includes Hepatitis C virus), and
    Genus *Pestivirus* (type species include Bovine viral diarrhea virus, classical swine fever and hog cholera).

In a more preferred embodiment of this aspect of the present invention, said *Flavivirus* is the Hepatitis C virus (hereinafter referred as HCV).

In a third aspect, the present invention relates to a pharmaceutical composition comprising as an active principle at least one 4,6-disubstituted or 2,4,6-trisubstituted pteridine derivative as defined above, e.g. in the form of a pharmaceutically acceptable salt. The latter include any therapeutically active non-toxic addition salt which the 4,6-disubstituted or 2,4,6-trisubstituted pteridine compounds of the present invention are able to form with a salt-forming agent. Such addition salts may conveniently be obtained by treating the pteridine derivatives of the invention with an appropriate salt-forming acid or base. For instance, 4,6-disubstituted and 2,4,6-trisubstituted pteridine derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as, but not limited to, hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzenesulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphthoate, hydroxyethanesulfonate, mandelate, methylsulfate, pantothenate, stearate, as well as salts derived from ethanedioic, propanedioic, butanedioic, (Z)-2-butenedioic, (E)2-butenedioic, 2-hydroxy-butanedioic, 2,3-dihydroxybutanedioic, 2-hydroxy-1,2,3-propanetricarboxylic and cyclo-hexanesulfamic acids, and the like.

4,6-disubstituted and 2,4,6-trisubstituted pteridine derivatives having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylene-diamine, chloroprocaine, choline, diethanolamine, ethylene-diamine, N-methyl-glucamine, procaine and the like.

Reaction conditions for treating the 4,6-disubstituted and 2,4,6-trisubstituted pteridine derivatives of this invention with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water-solubility, lower toxicity, greater stability and/or slower dissolution rate to the substituted pteridine derivative of this invention.

The present invention further provides the use of a 4,6-disubstituted or 2,4,6-trisubstituted pteridine derivative of the present invention, or a pharmaceutically acceptable salt thereof, or a solvate thereof, or a stereoisomer thereof or a pro-drug form thereof, as a biologically-active ingredient, i.e. active principle, especially as a medicine or for the manufacture of a medicament for the prevention or treatment of viral infections, especially infections due to Flaviridae, and pathologic conditions associated therewith such as, but not limited to, hepatitis C.

The invention further relates to a pharmaceutical composition comprising:

(a) one or more 4,6-disubstituted or 2,4,6-trisubstituted pteridine derivatives selected from the group as defined above, and
(b) one or more pharmaceutically acceptable carriers.

In another embodiment, this invention provides combinations, preferably synergistic combinations, of one or more 4,6-disubstituted or 2,4,6-trisubstituted pteridine derivatives of this invention with one or more other antiviral agents. As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein below, this principle may be applied to a number of desirable effects such as, but not limited to, anti-viral activity against HCV.

The present invention further relates to a pharmaceutical composition or combined preparation having synergistic effects against a viral infection, especially a hepatitis C virus infection, and containing:

(a) at least one 4,6-disubstituted and 2,4,6-trisubstituted pteridine derivative selected from the group as defined above, and
(b) one or more other anti-viral agents, and
(c) optionally one or more pharmaceutical excipients or pharmaceutically acceptable carriers, for simultaneous, separate or sequential use in the treatment of a viral infection, in particular HCV infection.

Suitable anti-viral agents for inclusion into the synergistic antiviral compositions or combined preparations of this invention include, for instance, retroviral enzyme inhibitors belonging to categories well known in the art, such as HIV-1 IN inhibitors, nucleoside reverse transcriptase inhibitors (e.g. zidovudine, lamivudine, didanosine, stavudine, zalcitabine and the like), non-nucleoside reverse transcriptase inhibitors (e.g. nevirapine, delavirdine and the like), other reverse transcriptase inhibitors (e.g. foscarnet sodium and the like), and HIV-1 protease inhibitors (e.g. saquinavir, ritonavir, indinavir, nelfinavir and the like). Other suitable antiviral agents include for instance acemannan, acyclovir, adefovir, alovudine, alvircept, amantadine, aranotin, arildone, atevirdine, avridine, cidofovir, cipamfylline, cytarabine, desciclovir, disoxaril, edoxudine, enviradene, enviroxime, famciclovir, famotine, fiacitabine, fialuridine, floxuridine, fosarilate, fosfonet, ganciclovir, idoxuridine, kethoxal, lobucavir, memotine, methisazone, penciclovir, pirodavir, somantadine, sorivudine, tilorone, trifluridine, valaciclovir, vidarabine, viroxime, zinviroxime, moroxydine, podophyllotoxin, ribavirine, rimantadine, stallimycine, statolon, tromantadine and xenazoic acid, and their pharmaceutically acceptable salts.

Especially relevant to this aspect of the invention is the inhibition of the replication of hepatitis C virus, in particular in human beings and other mammals such as primates. Therefore, of particular relevance in the context of HCV prevention or treatment is co-administration with one or more other agents aiming at HCV inhibition well known in the art, such as but not limited to, (pegylated) interferon alpha, ribavirin, an NS3 protease inhibitor (such as telaprivir), or nucleoside- or non-nucleoside-based inhibitors of NS5B polymerase. Synergistic activity of the pharmaceutical compositions or combined preparations of this invention against viral infection may be readily determined by means of one or more tests such as, but not limited to, the isobologram method, as previously described by Elion et al. in *J. Biol. Chem.* (1954) 208:477-488 and by Baba et al. in *Antimicrob. Agents Chemother*. (1984) 25:515-517, using $EC_{50}$ for calculating the fractional inhibitory concentration (hereinafter referred as FIC). When the minimum FIC index corresponding to the FIC of combined compounds (e.g., $FIC_x+FIC_y$) is equal to 1.0, the combination is said to be additive; when it is between 1.0 and 0.5, the combination is defined as sub-synergistic, and when it is lower than 0.5, the combination is by defined as synergistic. When the minimum FIC index is between 1.0 and 2.0, the combination is defined as sub-antagonistic and, when it is higher than 2.0, the combination is defined as antagonistic.

The pharmaceutical composition or combined preparation with synergistic activity against viral infection according to this invention may contain the 4,6-disubstituted or 2,4,6-trisubstituted pteridine derivative over a broad content range depending on the contemplated use and the expected effect of the preparation. Generally, the pteridine derivative content of the combined preparation is within the range of from 0.1 to 99.9% by weight, preferably from 1 to 99% by weight, more preferably from about 5 to 95% by weight.

The pharmaceutical compositions and combined preparations according to the present invention may be administered orally or in any other suitable fashion. Oral administration is preferred and the preparation may have the form of a tablet, aqueous dispersion, dispersable powder or granule, emulsion, hard or soft capsule, syrup, elixir or gel. The dosing forms may be prepared using any method known in the art for manufacturing these pharmaceutical compositions and may comprise as additives sweeteners, flavoring agents, coloring agents, preservatives and the like. Carrier materials and excipients are detailed herein below and may include, inter alia, calcium carbonate, sodium carbonate, lactose, calcium phosphate or sodium phosphate; granulating and disintegrating agents, binding agents and the like. The pharmaceutical composition or combined preparation of this invention may be included in a gelatin capsule mixed with any inert solid diluent or carrier material, or has the form of a soft gelatin capsule, in which the ingredient is mixed with a water or oil medium. Aqueous dispersions may comprise the biologically active composition or combined preparation in combination with a suspending agent, dispersing agent or wetting agent. Oil dispersions may comprise suspending agents such as a vegetable oil. Rectal administration is also applicable, for instance in the form of suppositories or gels. Injection (e.g. intramuscularly or intraperitoneously) is also applicable as a mode of administration, for instance in the form of injectable solutions or dispersions, depending upon the disorder to be treated and the condition of the patient.

The term "pharmaceutically acceptable carrier or excipient" as used herein in relation to pharmaceutical compositions and combined preparations means any material or substance with which the active principle, i.e. the 4,6-disubstituted or 2,4,6-trisubstituted pteridine derivative of the present invention, and optionally the one or more other antiviral agents, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compo-sitions and their formulation are well known to those skilled in the art. There is no particular restriction to their selection within the present invention although, due to the usually low or very low water-solubility of the 4,6-disubstituted or 2,4,6-trisubstituted pteridine derivatives of this invention, special attention will be paid to the selection of suitable carrier combinations that can assist in properly formulating them in view of the expected time release profile. Suitable pharmaceutical carriers include additives such as, but not limited to, wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals, especially humans.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. may also be prepared by micronisation, for instance in view to obtain them in the form of microspheres usually having a diameter of about 1 to 10 µm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps include, but are not limited to, alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alkanolamine salts of dodecylbenzene sulphonic acid or dibutyl-naphthalenesulphonic acid or a naphthalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphoshatidylcholine and their mixtures.

Suitable non-ionic surfactants include, but are not limited to, poly-ethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediamino-polypropylene glycol preferably containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants include, but are not limited to, nonylphenol-polyethoxyethanol, castor oil polyglycolic ethers, polypropylene/polyethylene oxide adducts, tributylphenoxypolyethoxyethanol, polyethyleneglycol and octylphenoxy-polyethoxyethanol. Fatty acid esters of polyethylene sorbitan (such as polyoxyethylene sorbitan trioleate), glycerol, sorbitan, sucrose and pentaerythritol are also suitable non-ionic surfactants for the purpose of the present invention.

Suitable cationic surfactants include, but are not limited to, quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further sub-stituents, unsubstituted or halogenated lower alkyl, benzyl and/or hydroxy-$C_{1-4}$ alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the present invention. Suitable such agents include in particular, but are not limited to, highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as, but not limited to, magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions and combined preparations of the invention. Control release compositions may thus be achieved by selecting appropriate pharmaceutically acceptable polymer carriers such as for example polyesters, polyaminoacids, polyvinyl-pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical liquid pharmaceutically acceptable carriers for this purpose therefore include biocompatible aqueous buffers, ethanol, glycerol, propylene glycol, polyethylene glycol, complexing agents such as cyclodextrins and the like, and mixtures thereof.

Other modes of local drug administration can also be used. For example, the selected biologically active agent may be administered topically, in an ointment, gel or the like, or transdermally, using a conventional transdermal drug delivery system.

Since, in the case of combined preparations including the 4,6-disubstituted or 2,4,6-trisubstituted pteridine derivative of the present invention and one or more other antiviral agents, both ingredients do not necessarily bring out their synergistic therapeutic effect directly at the same time in the patient to be treated, the said combined preparation may be in the form of a medical kit or package containing the two ingredients in separate but adjacent form. In the latter context, each ingredient may therefore be formulated in a way suitable for an administration route different from that of the other ingredient, e.g. one of them may be in the form of an oral or parenteral formulation whereas the other is in the form of an ampoule for intravenous injection or an aerosol.

The present invention further relates to a method for treating a viral infection or a pathologic condition associated therewith, including hepatitis C in a patient, preferably a mammal, more preferably a human being. The method of this invention consists of administering to the patient in need thereof a therapeutically effective amount of a 4,6-disubstituted or 2,4,6-trisubstituted pteridine derivative of the present invention, optionally together with an effective amount of one or more other antiviral agents, or a pharmaceutical composition comprising the same, such as disclosed above in extensive details.

The therapeutically effective amount of the 4,6-disubstituted or 2,4,6-trisubstituted pteridine derivative to be administered according to the present invention is usually in the range of about 0.01 mg to 20 mg, preferably about 0.1 mg to 5 mg, per day per kg body weight for human beings. Depending upon the severity of the pathologic condition to be treated and the patient's condition, the said therapeutically effective amount may be divided into several sub-units per day or may be administered at more than one day intervals. The patient to be treated may be any warm-blooded animal, preferably a mammal, more preferably a human being, suffering from an infection by a virus being a member of the Flaviridae family, e.g. HCV, or a pathologic condition associated therewith.

The present invention will be further described with reference to certain more specific embodiments and examples, but the present invention is not limited thereto. The following examples are given by way of illustration only.

Examples 1 to 73—Synthesis of
2-amino-4-ethoxy-6-substituted Pteridines

The synthetic method may be represented schematically as follows:

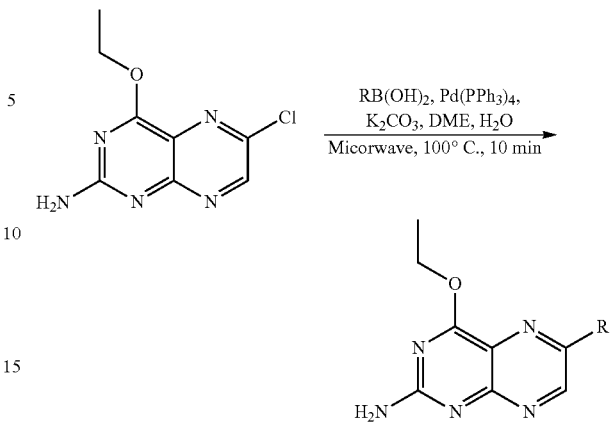

The general procedure used for preparing 2-amino-6-aryl-4-ethoxy-pteridines and 2-amino-6-heteroaryl-4-ethoxy-pteridines starts from the common intermediate 2-amino-6-chloro-4-ethoxypteridine (described in WO 2005/025574) as follows. A mixture of 2-amino-6-chloro-4-ethoxypteridine (23 mg, 0.1 mmol), potassium carbonate (27 mg, 0.2 mmol), tetrakis(triphenylphosphine) palladium (8 mg, 0.007 mmol) and a suitable arylboronic or heteroarylboronic acid, or a pinacol ester thereof, (0.12 mmol) in dimethylether (1.5 mL) and water (1 mL) was heated to 100° C. for 10 minutes under microwave irradiation. Solvents were concentrated in vacuo and the residue was purified by high performance liquid chromatography (hereinafter referred as HPLC) onto a C18 column with a gradient of $H_2O$, 0.1% TFA-acetonitrile, in order to afford the pure desired product. This procedure provided, with yield ranging from 5% to 65%, depending upon the aryl or heteroaryl group R introduced at position 6 of the pteridine ring, the pure compounds shown in the table 1, which were characterized by their mass spectrum MS.

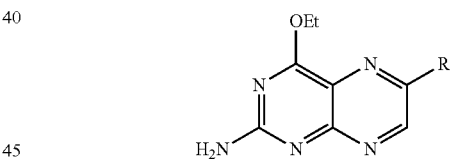

TABLE 1

| Example | R | Compound name | M + H |
|---|---|---|---|
| 1 | 2,6-dichlorophenyl | 6-(2,6-dichlorophenyl)-4-ethoxypteridin-2-ylamine | 336.1 |
| 2 | 3-cyanophenyl | 3-(2-amino-4-ethoxypteridin-6-yl)benzonitrile | 293.3 |
| 3 | 3-fluoro-4-methoxyphenyl | 4-ethoxy-6-(3-fluoro-4-methoxyphenyl)pteridin-2-ylamine | 316.1 |

TABLE 1-continued

| Example | R | Compound name | M + H |
|---|---|---|---|
| 4 | 4-(trifluoromethoxy)phenyl | 4-ethoxy-6-(4-(trifluoromethoxy)phenyl)pteridin-2-ylamine | 352.5 |
| 5 | 3,5-bis(trifluoromethyl)phenyl | 6-(3,5-bis(trifluoromethyl)phenyl)-4-ethoxypteridin-2-ylamine | 404.5 |
| 6 | 4-(trifluoromethyl)phenyl | 4-ethoxy-6-(4-(trifluoromethyl)phenyl)pteridin-2-ylamine | 336.5 |
| 7 | 4-chloro-3-fluorophenyl | 6-(4-chloro-3-fluorophenyl)-4-ethoxypteridin-2-ylamine | 320.3 |
| 8 | 3,5-dichlorophenyl | 6-(3,5-dichlorophenyl)-4-ethoxypteridin-2-ylamine | 336.3 |
| 9 | 3,4-difluorophenyl | 6-(3,4-difluorophenyl)-4-ethoxypteridin-2-ylamine | 304.3 |
| 10 | 2-fluorophenyl | 4-ethoxy-6-(2-fluorophenyl)pteridin-2-ylamine | 286.3 |
| 11 | 2,6-difluorophenyl | 6-(2,6-difluorophenyl)-4-ethoxypteridin-2-ylamine | 304.1 |
| 12 | 3,5-difluorophenyl | 6-(3,5-difluorophenyl)-4-ethoxypteridin-2-ylamine | 304.1 |
| 13 | 2,3-difluorophenyl | 6-(2,3-difluorophenyl)-4-ethoxypteridin-2-ylamine | 304.3 |
| 14 | 3-fluorophenyl | 4-ethoxy-6-(3-fluorophenyl)pteridin-2-ylamine | 286.2 |

TABLE 1-continued

| Example | R | Compound name | M + H |
|---|---|---|---|
| 15 | 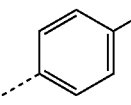 | dimethyl (4-(2-amino-4-ethoxypteridin-6-yl)phenyl)methylphosphonate | 390.0 |
| 16 | 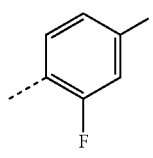 | 6-(2,4-difluorophenyl)-4-ethoxypteridin-2-ylamine | 304.3 |
| 17 | 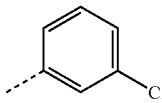 | 6-(3-chlorophenyl)-4-ethoxypteridin-2-ylamine | 302.3 |
| 18 | 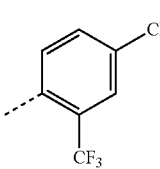 | 6-(2,4-bis(trifluoromethyl)phenyl)-4-ethoxypteridin-2-ylamine | 404.5 |
| 19 | 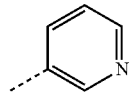 | 4-ethoxy-6-(pyridin-3-yl)pteridin-2-ylamine | 269.3 |
| 20 | 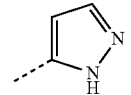 | 4-ethoxy-6-(1H-pyrazol-5-yl)pteridin-2-ylamine | 258.3 |
| 21 | 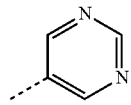 | 4-ethoxy-6-(pyrimidin-5-yl)pteridin-2-ylamine | 270.2 |
| 22 | 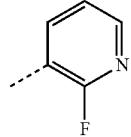 | 4-ethoxy-6-(2-fluoropyridin-3-yl)pteridin-2-ylamine | 287.1 |
| 23 | 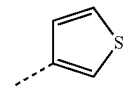 | 4-ethoxy-6-(thiophen-3-yl)pteridin-2-ylamine | 274.3 |
| 24 | 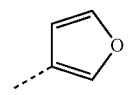 | 4-ethoxy-6-(furan-3-yl)pteridin-2-ylamine | 258.1 |
| 25 | 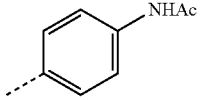 | N-(4-(2-amino-4-ethoxypteridin-6-yl)phenyl)acetamide | 325.2 |
| 26 | 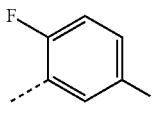 | 6-(2,5-difluorophenyl)-4-ethoxypteridin-2-ylamine | 304.3 |
| 27 | 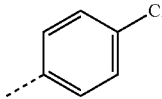 | 6-(4-chlorophenyl)-4-ethoxypteridin-2-ylamine | 302.3 |

TABLE 1-continued

| Example | R | Compound name | M + H |
|---|---|---|---|
| 28 | 2-CF₃-phenyl | 4-ethoxy-6-(2-(trifluoromethyl)phenyl)pteridin-2-ylamine | 336.3 |
| 29 | 1H-indol-5-yl | 4-ethoxy-6-(1H-indol-5-yl)pteridin-2-ylamine | 307.3 |
| 30 | 4-SO₂Me-phenyl | 4-ethoxy-6-(4-(methylsulfonyl)phenyl)pteridin-2-ylamine | 346.3 |
| 31 | pyridin-4-yl | 4-ethoxy-6-(pyridin-4-yl)pteridin-2-ylamine | 269.3 |
| 32 | 1H-pyrazol-4-yl | 4-ethoxy-6-(1H-pyrazol-4-yl)pteridin-2-ylamine | 258.3 |
| 33 | furan-2-yl | 4-ethoxy-6-(furan-2-yl)pteridin-2-ylamine | 258.3 |
| 34 | 2-chlorophenyl | 6-(2-chlorophenyl)-4-ethoxypteridin-2-ylamine | 302.1 |
| 35 | 2,3-dichlorophenyl | 6-(2,3-dichlorophenyl)-4-ethoxypteridin-2-ylamine | 336.1 |
| 36 | 3-chloro-4-fluorophenyl | 6-(3-chloro-4-fluorophenyl)-4-ethoxypteridin-2-ylamine | 320.1 |
| 37 | 2-chloro-4-fluorophenyl | 6-(2-chloro-4-fluorophenyl)-4-ethoxypteridin-2-ylamine | 320.1 |
| 38 | 3-CF₃-phenyl | 4-ethoxy-6-(3-(trifluoromethyl)phenyl)pteridin-2-ylamine | 336.2 |
| 39 | 3-OCF₃-phenyl | 4-ethoxy-6-(3-(trifluoromethoxy)phenyl)pteridin-2-ylamine | 352.1 |

TABLE 1-continued

| Example | R | Compound name | M + H |
|---|---|---|---|
| 40 | 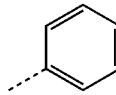 | 4-(2-amino-4-ethoxypteridin-6-yl)-N-methylbenzamide | 325.2 |
| 41 | 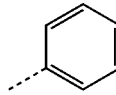 | 4-(2-amino-4-ethoxypteridin-6-yl)-N-cyclopropylbenzamide | 351.2 |
| 42 | 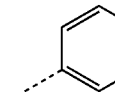 | 6-(4-(dimethylamino)phenyl)-4-ethoxypteridin-2-ylamine | 311.2 |
| 43 | 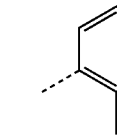 | 4-ethoxy-6-(4-fluoro-2-methylphenyl)pteridin-2-ylamine | 300.2 |
| 44 | 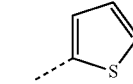 | 5-(2-amino-4-ethoxypteridin-6-yl)thiophene-2-carbonitrile | 299.1 |
| 45 | 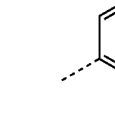 | 4-ethoxy-6-(2-(trifluoromethoxy)phenyl)pteridin-2-ylamine | 352.1 |
| 46 | 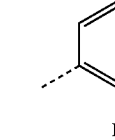 | 4-ethoxy-6-(2,3,4-trifluorophenyl)pteridin-2-ylamine | 322.0 |
| 47 | 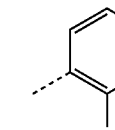 | 6-(2-chloro-4-(trifluoromethyl)phenyl)-4-ethoxypteridin-2-ylamine | 369.9 |
| 48 | 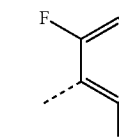 | 4-ethoxy-6-(2,4,6-trifluorophenyl)pteridin-2-ylamine | 322.0 |
| 49 |  | 6-(5-chlorothiophen-2-yl)-4-ethoxypteridin-2-ylamine | 308.1 |
| 50 | 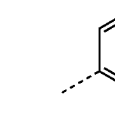 | 2-(2-amino-4-ethoxypteridin-6-yl)phenol | 284.3 |

TABLE 1-continued

| Example | R | Compound name | M + H |
|---|---|---|---|
| 51 | 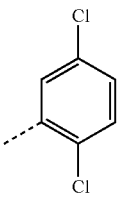 | 6-(2,5-dichlorophenyl)-4-ethoxypteridin-2-ylamine | 336.1 |
| 52 | 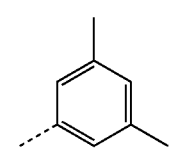 | 6-(3,5-dimethylphenyl)-4-ethoxypteridin-2-ylamine | 296.5 |
| 53 | 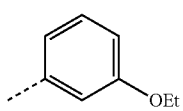 | 4-ethoxy-6-(3-ethoxyphenyl)pteridin-2-ylamine | 312.3 |
| 54 | 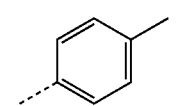 | 4-ethoxy-6-p-tolylpteridin-2-ylamine | 282.3 |
| 55 | 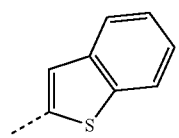 | 6-(benzo[b]thiophen-2-yl)-4-ethoxypteridin-2-ylamine | 324.5 |
| 56 | 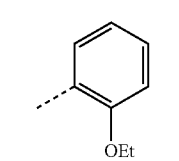 | 4-ethoxy-6-(2-ethoxyphenyl)pteridin-2-ylamine | 312.3 |
| 57 | 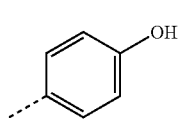 | 4-(2-amino-4-ethoxypteridin-6-yl)phenol | 284.3 |
| 58 | 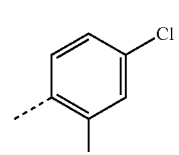 | 6-(2,4-dichlorophenyl)-4-ethoxypteridin-2-ylamine | 336.1 |
| 59 | 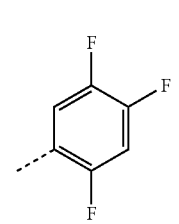 | 4-ethoxy-6-(2,4,5-trifluorophenyl)pteridin-2-ylamine | 322.3 |
| 60 | 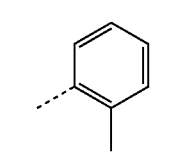 | 4-ethoxy-6-(2-methylphenyl)pteridin-2-ylamine | 282.3 |

TABLE 1-continued

| Example | R | Compound name | M + H |
|---|---|---|---|
| 61 | 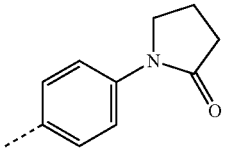 | 1-(4-(2-amino-4-ethoxypteridin-6-yl)phenyl)pyrrolidin-2-one | 351.0 |
| 62 | 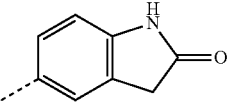 | 5-(2-amino-4-ethoxypteridin-6-yl)indolin-2-one | 323.4 |
| 63 | 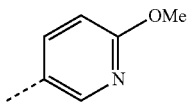 | 4-ethoxy-6-(6-methoxypyridin-3-yl)pteridin-2-ylamine | 299.3 |
| 64 | 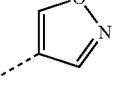 | 4-ethoxy-6-(isoxazol-4-yl)pteridin-2-ylamine | 259.2 |
| 65 | 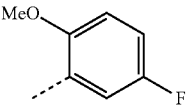 | 4-ethoxy-6-(5-fluoro-2-methoxyphenyl)pteridin-2-ylamine | 316.1 |
| 66 | 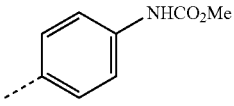 | methyl 4-(2-amino-4-ethoxypteridin-6-yl)phenylcarbamate | 341.3 |
| 67 | 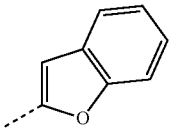 | 6-(benzofuran-2-yl)-4-ethoxypteridin-2-ylamine | 308.2 |
| 68 | 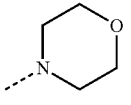 | 4-ethoxy-6-morpholinopteridin-2-ylamine | 277.2 |
| 69 | 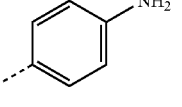 | 6-(4-aminophenyl)-4-ethoxypteridin-2-ylamine | 283.1 |
| 70 | 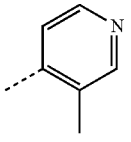 | 4-ethoxy-6-(3-methylpyridin-4-yl)pteridin-2-ylamine | 283.0 |
| 71 | 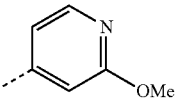 | 4-ethoxy-6-(2-methoxypyridin-4-yl)pteridin-2-ylamine | 299.0 |
| 72 | 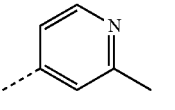 | 4-ethoxy-6-(2-methylpyridin-4-yl)pteridin-2-ylamine | 283.3 |

TABLE 1-continued

| Example | R | Compound name | M + H |
|---|---|---|---|
| 73 | 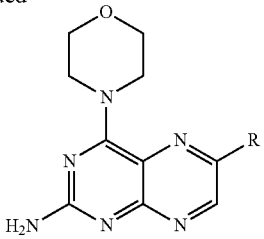 | 4-ethoxy-6-(pyridin-2-yl)pteridin-2-ylamine | 269.3 |

(end of table 1)

Examples 74 to 140—Synthesis of 2-amino-4-morpholin-4-yl-6-substituted-pteridines The scheme below shows a general procedure for the synthesis of 2-amino-4-morpholin-4-yl-6-substituted-pteridines.

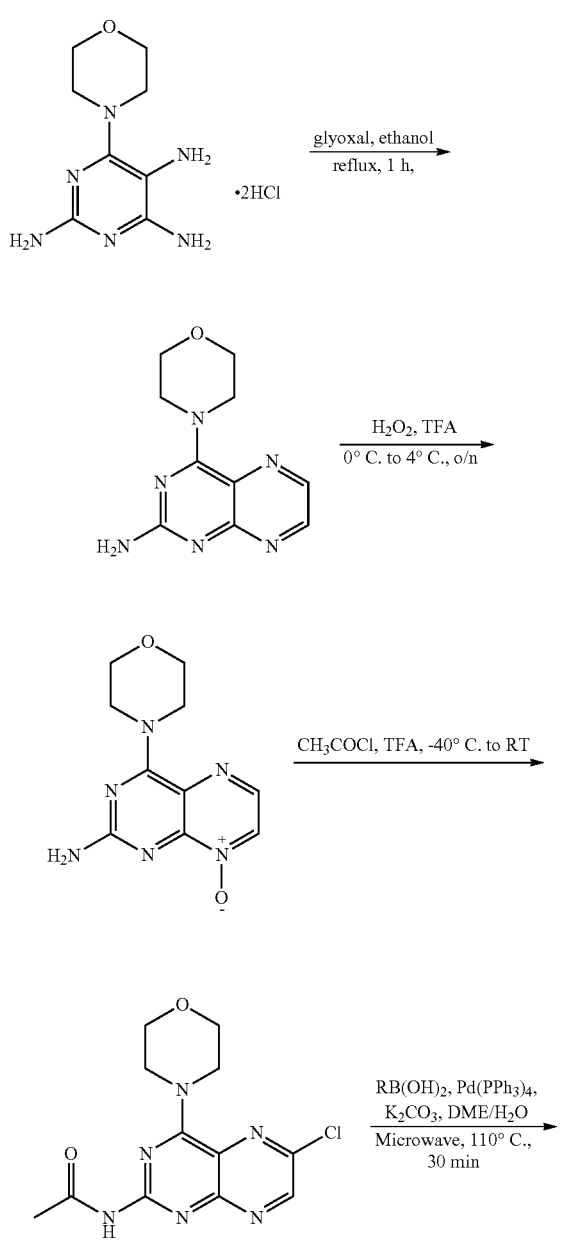

Synthesis of 4-morpholin-4-yl-pteridin-2-ylamine (Example 74)

To a solution of 2,5,6-triamino-4-morpholino-pyrimidine dihydrochloride (7.08 g, 25 mmol) in ethanol (60 mL) was added glyoxal (405 solution in water, 2.9 mL, 25 mmol). The reaction mixture was refluxed for one hour. After cooling, the solvent was removed under reduced pressure. The residue was purified by flash chromatography (using 7% MeOH/DCM as the eluent), providing the pure title compound in 80% yield (4.6 g), which was characterized by mass spectrometry as follows: MS (m/z) 233.3 [M+H]$^+$.

Synthesis of 4-morpholin-4-yl-8-oxy-pteridin-2-ylamine (Example 75)

To a cooled (0° C.) solution of 4-morpholin-4-yl-pteridin-2-ylamine (4.6 g, 20 mmol) in trifluoroacetic acid (80 mL) was added dropwise 5.1 mL of a 35% aqueous H$_2$O$_2$ solution. The reaction mixture was kept at 4° C. overnight. The solution was concentrated to dryness, providing crude product (4.9 g, 98% yield) as a yellow powder. The crude material was used without further purification, but was characterized by mass spectrometry as follows: MS (m/z) 249.3 [M+H]$^+$.

Synthesis of N-(6-chloro-4-morpholin-4-yl-pteridin-2-yl)-acetamide (Example 76)

A suspension of 4-morpholin-4-yl-8-oxy-pteridin-2-ylamine (2.3 g) in acetyl chloride (25 mL) was stirred at −40° C. Trifluoroacetic acid (12 mL) was then added dropwise. The resulting solution was slowly warmed up to room temperature and stirred for one day. Reaction was carefully quenched with ice, followed by neutralization with ammonium hydroxide solution. The aqueous phase was extracted with DCM repeatedly. The combined organic layers were concentrated in vacuo and the residue was purified by flash chromatography providing the pure title compound as a yellow solid (1.2 g, 43% yield) was characterized by mass spectrometry as follows: MS (m/z) 309.2 [M+H]$^+$.

The general procedure used for preparing 2-amino-6-aryl-4-morpholino-pteridines and 2-amino-6-heteroaryl-4-morpholino-pteridines was as follows. A mixture of 2-amino-6-chloro-4-morpholino-pteridine (31 mg, 0.1 mmol), potassium carbonate (42 mg, 0.4 mmol), tetrakis(triphenylphosphine) palladium (8 mg, 0.007 mmol) and a suitable arylboronic or heteroarylboronic acid, or a pinacol ester thereof (0.12 mmol), in dimethylether (2 mL) and water (1 mL) was heated to 110° C. for 30 minutes under microwave irradiation. Solvents were concentrated in vacuo and the residue was purified by HPLC onto a C18 column with a gradient of H$_2$O, 0.1% TFA-acetonitrile. This procedure provided, with yields ranging from 10% to 70%, depending upon the aryl or heteroaryl group R introduced at position 6 of the pteridine ring, the pure compounds which were characterized by their mass spectrum MS as indicated in Table 2 below.

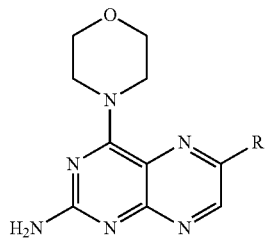

TABLE 2

| Example | R | Compound name | M + H |
|---|---|---|---|
| 77 | 2-fluorophenyl | 6-(2-fluorophenyl)-4-morpholinopteridin-2-ylamine | 327.2 |
| 78 | 2-chlorophenyl | 6-(2-chlorophenyl)-4-morpholinopteridin-2-ylamine | 343.2 |
| 79 | 2-(trifluoromethyl)phenyl | 4-morpholino-6-(2-(trifluoromethyl)phenyl)pteridin-2-ylamine | 377.1 |
| 80 | 2-methoxyphenyl | 6-(2-methoxyphenyl)-4-morpholinopteridin-2-ylamine | 339.2 |
| 81 | 3-fluorophenyl | 6-(3-fluorophenyl)-4-morpholinopteridin-2-ylamine | 327.2 |
| 82 | 3-chlorophenyl | 6-(3-chlorophenyl)-4-morpholinopteridin-2-ylamine | 343.2 |
| 83 | 3-(trifluoromethyl)phenyl | 4-morpholino-6-(3-(trifluoromethyl)phenyl)-pteridin-2-ylamine | 377.1 |
| 84 | 3-(trifluoromethoxy)phenyl | 4-morpholino-6-(3-(trifluoromethoxy)phenyl)-pteridin-2-ylamine | 393.1 |

TABLE 2-continued

| Example | R | Compound name | M + H |
|---|---|---|---|
| 85 | 3-cyanophenyl | 3-(2-amino-4-morpholinopteridin-6-yl)benzonitrile | 334.3 |
| 86 | 4-(trifluoromethoxy)phenyl | 4-morpholino-6-(4-(trifluoromethoxy-phenyl)pteridin-2-ylamine | 393.1 |
| 87 | 4-cyanophenyl | 4-(2-amino-4-morpholinopteridin-6-yl)benzonitrile | 334.2 |
| 89 | 4-(morpholinomethyl)phenyl | 4-morpholino-6-(4-(morpholino-methyl)phenyl)pteridin-2-ylamine | 408.1 |
| 90 | 2,3-difluorophenyl | 6-(2,3-difluorophenyl)-4-morpholinopteridin-2-ylamine | 345.2 |
| 91 | 2,3-dichlorophenyl | 6-(2,3-dichlorophenyl)-4-morpholinopteridin-2-amine | 377 |
| 92 | 2-chloro-4-fluorophenyl | 6-(2-chloro-4-fluorophenyl)-4-morpholinopteridin-2-ylamine | 361.1 |
| 93 | 2,4-bis(trifluoromethyl)phenyl | 6-(2,4-bis(trifluoromethyl)phenyl)-4-morpholinopteridin-2-ylamine | 444.9 |
| 94 | 2,4-difluorophenyl | 6-(2,4-difluorophenyl)-4-morpholinopteridin-2-ylamine | 345.2 |
| 95 | 2,6-dichlorophenyl | 6-(2,6-dichlorophenyl)-4-morpholinopteridin-2-ylamine | 377 |
| 96 | 3,5-bis(trifluoromethyl)phenyl | 6-(3,5-bis(trifluoromethyl)phenyl)-4-morpholinopteridin-2-ylamine | 445.5 |

TABLE 2-continued

| Example | R | Compound name | M + H |
|---|---|---|---|
| 97 | 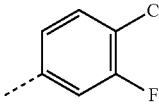 | 6-(4-chloro-3-fluorophenyl)-4-morpholinopteridin-2-ylamine | 361.3 |
| 98 | 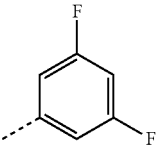 | 6-(3,5-difluorophenyl)-4-morpholinopteridin-2-ylamine | 345.3 |
| 99 | 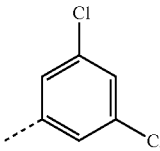 | 6-(3,5-dichlorophenyl)-4-morpholinopteridin-2-ylamine | 377.3 |
| 100 | 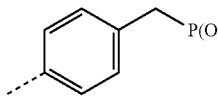 | dimethyl (4-(2-amino-4-morpholinopteridin-6-yl)phenyl)methylphosphonate | 431 |
| 101 |  | 6-(2,6-difluorophenyl)-4-morpholinopteridin-2-ylamine | 345.2 |
| 102 | 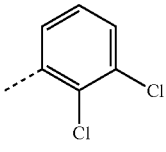 | 6-(3,4-dichlorophenyl)-4-morpholinopteridin-2-ylamine | 377 |
| 103 | 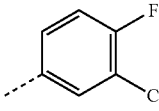 | 6-(3-chloro-4-fluorophenyl)-4-morpholinopteridin-2-ylamine | 361.1 |
| 104 | 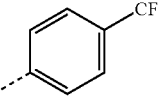 | 4-morpholino-6-(4-(trifluoromethyl)phenyl)pteridin-2-ylamine | 377.5 |
| 105 | 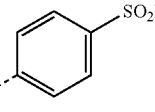 | 6-(4-(methylsulfonyl)phenyl)-4-morpholinopteridin-2-ylamine | 387.3 |
| 106 | 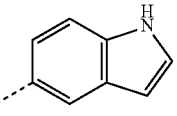 | 6-(1H-indol-5-yl)-4-morpholinopteridin-2-ylamine | 348.5 |
| 107 | 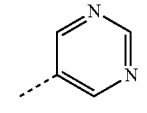 | 4-morpholino-6-(pyrimidin-5-yl)pteridin-2-ylamine | 311.5 |
| 108 | 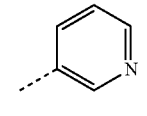 | 4-morpholino-6-(pyridin-3-yl)pteridin-2-ylamine | 310.5 |

TABLE 2-continued

| Example | R | Compound name | M + H |
|---|---|---|---|
| 109 | 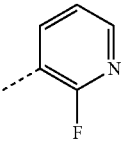 | 6-(2-fluoropyridin-3-yl)-4-morpholino-pteridin-2-ylamine | 328.3 |
| 110 | 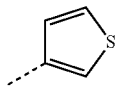 | 4-morpholino-6-(thiophen-3-yl)pteridin-2-ylamine | 315.3 |
| 111 | 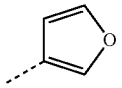 | 6-(furan-3-yl)4-morpholinopteridin-2-ylamine | 299.5 |
| 112 | 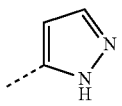 | 4-morpholino-6-(1H-pyrazol-5-yl)pteridin-2-ylamine | 299.5 |
| 113 | 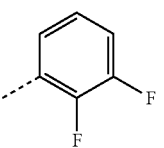 | 6-(2,3-difluorophenyl)-4-morpholino-pteridin-2-ylamine | 345.3 |
| 114 | 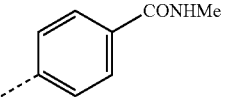 | 4-(2-amino-4-morpholinopteridin-6-yl)-N-methylbenzamide | 366.2 |
| 115 | 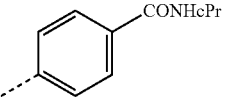 | 4-(2-amino-4-morpholinopteridin-6-yl)-N-cyclopropylbenzamide | 392.1 |
| 116 | 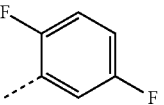 | 6-(2,5-difluorophenyl)-4-morpholinopteridin-2-ylamine | 345.2 |
| 117 | 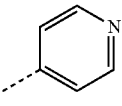 | 4-morpholino-6-(pyridin-4-yl)pteridin-2-ylamine | 310.2 |
| 118 | 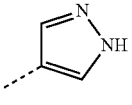 | 4-morpholino-6-(1H-pyrazol-4-yl)pteridin-2-ylamine | 299.2 |
| 119 | 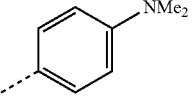 | 6-(4-(dimethylamino)phenyl)-4-morpholinopteridin-2-ylamine | 352.5 |
| 120 | 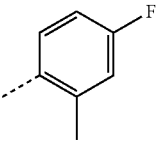 | 6-(4-fluoro-2-methylphenyl)-4-morpholinopteridin-2-ylamine | 341.3 |

TABLE 2-continued

| Example | R | Compound name | M + H |
|---|---|---|---|
| 121 | 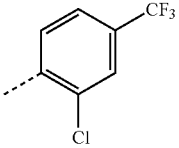 | 6-(2-chloro-4-(trifluoromethyl)phenyl)-4-morpholinopteridin-2-ylamine | 411.5 |
| 122 | 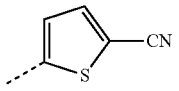 | 5-(2-amino-4-morpholinopteridin-6-yl)thiophene-2-carbonitrile | 340.2 |
| 123 | 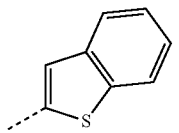 | 6-(benzo[b]thiophen-2-yl)-4-morpholinopteridin-2-ylamine | 365.3 |
| 124 | 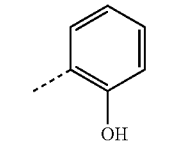 | 2-(2-amino-4-morpholinopteridin-6-yl)phenol | 325.5 |
| 125 | 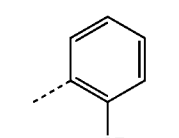 | 6-(2-ethoxyphenyl)-4-morpholinopteridin-2-ylamine | 353.5 |
| 126 | 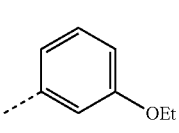 | 6-(3-ethoxyphenyl)-4-morpholinopteridin-2-ylamine | 353.5 |
| 127 | 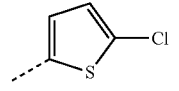 | 6-(5-chlorothiophen-2-yl)-morpholinopteridin-2-ylamine | 349 |
| 128 | 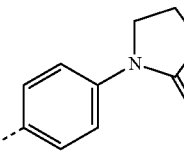 | 1-(4-(2-amino-4-morpholinopteridin-6-yl)phenyl)pyrrolidin-2-one | 392.1 |
| 129 | 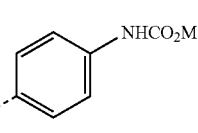 | methyl 4-(2-amino-4-morpholinopteridin-6-yl)phenylcarbamate | 382.2 |
| 130 | 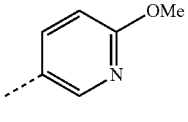 | 6-(6-methoxypyridin-3-yl)-4-morpholinopteridin-2-ylamine | 340.3 |
| 131 | 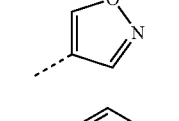 | 6-(isoxazol-4-yl)-4-morpholinopteridin-2-ylamine | 300.2 |
| 132 | 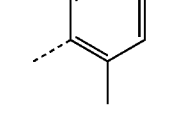 | 6-(2-methylphenyl)-4-morpholinopteridin-2-ylamine | 323.5 |

TABLE 2-continued

| Example | R | Compound name | M + H |
|---------|---|---------------|-------|
| 133 | 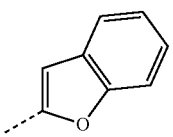 | 6-(benzofuran-2-yl)-4-morpholinopteridin-2-ylamine | 349.3 |
| 134 | 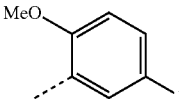 | 6-(5-fluoro-2-methoxyphenyl)-4-morpholinopteridin-2-ylamine | 357.2 |
| 135 | 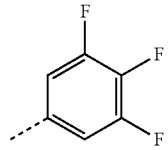 | 4-morpholino-6-(3,4,5-trifluorophenyl)pteridin-2-ylamine | 263.3 |
| 136 | 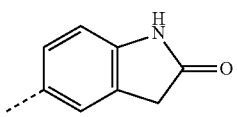 | 5-(2-amino-4-morpholinopteridin-6-yl)indolin-2-one | 364.7 |
| 137 | 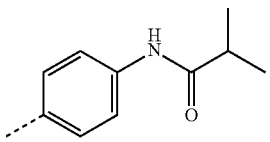 | N-(4-(2-amino-4-morpholinopteridin-6-yl)phenyl)isobutyramide | 394.3 |
| 138 | 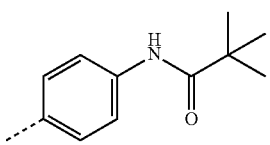 | N-(4-(2-amino-4-morpholinopteridin-6-yl)phenyl)pivalamide | 409 |
| 139 | 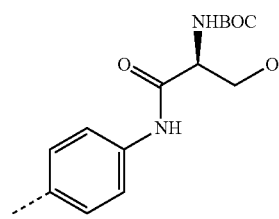 | (S)-tert-butyl 1-(4-(2-amino-4-morpholinopteridin-6-yl)phenylamino)-3-hydroxy-1-oxopropan-2-ylcarbamate | 511.5 |
| 140 | 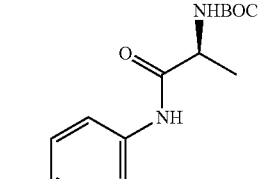 | (S)-tert-butyl 1-(4-(2-amino-4-morpholinopteridin-6-yl)phenylamino)-1-oxopropan-2-ylcarbamate | 496 |

(end of table 2)

Example 141—Synthesis of N-[6-(4-Amino-phenyl)-4-morpholin-4-yl-pteridin-2-yl]-acetamide Synthesis proceeds according to the following scheme:

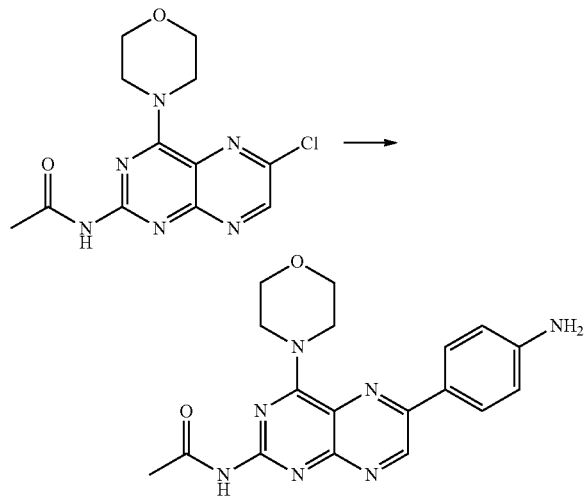

A mixture of 2-amino-6-chloro-4-morpholino-pteridine (600 mg, 1.9 mmol), potassium carbonate (394 mg, 66 mmol), tetrakis(triphenylphosphine) palladium (66 mg, 0.057 mmol) and 4-(4,4,5,5-tetramethyl-[1,3,2]dioxaborolan-2-yl)-phenylamine (511 mg, 2.3 mmol) in dimethylether (6 mL) and water (3 mL) was heated to 110° C. for 4 minutes under microwave irradiation. Solvents were concentrated in vacuo and the resulting solid was washed with water, methanol, and dichloromethane to provide 502 mg (yield: 72%) of the desired product as an orange solid, which was characterized by its mass spectrum as follows: MS (m/z) 366.8 [M+H]⁺.

Example 142—Synthesis of Cyclopropane carboxylic acid[4-(2-amino-4-morpholin-4-yl-pteridin-6-yl)-phenyl]-amide Synthesis proceeds according to the following scheme:

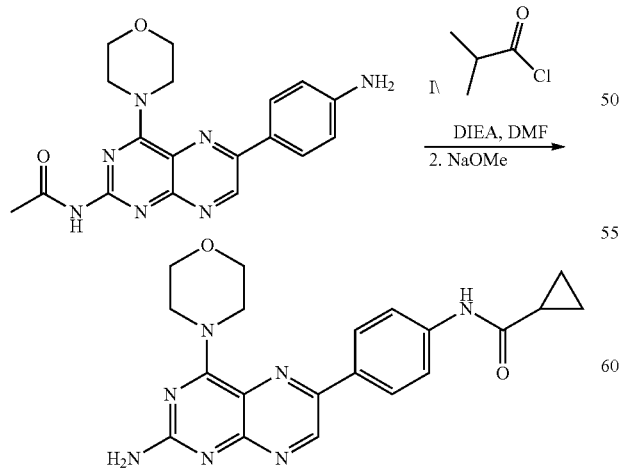

To a mixture of N-[6-(4-Amino-phenyl)-4-morpholin-4-yl-pteridin-2-yl]-acetamide (55 mg, 0.15 mmol) and diisopropylethylamine (78 µL, 0.15 mmol) in dimethylformamide (3 mL) was added cyclopropanecarbonyl chloride (14 µL, 0.15 mmol). The resulting mixture was stirred at room temperature for 4 hours. Chloroform was then added to the reaction mixture and extracted with saturated aqueous sodium bicarbonate solution and brine. The organic layer was dried over sodium sulfate and concentrated to dryness to provide 12 mg of solid as crude product. This material was dissolved in methanol (2 mL) and added NaOMe (0.1 mL, 0.5 N in methanol). The mixture was then heated to 100° C. for 10 minutes under microwave irradiation. Solvents were concentrated in vacuo and the residue was purified by flash chromatography (using 10% MeOH/DCM as the eluent), providing 4 mg of the desired product as a yellow solid, which was characterized by its mass spectrum as follows: MS (m/z) 393.0 [M+H]⁺.

Example 143—Synthesis of 6-(2,3-difluoro-phenyl)-pteridine-2,4-diamine

Synthesis proceeds according to the following scheme:

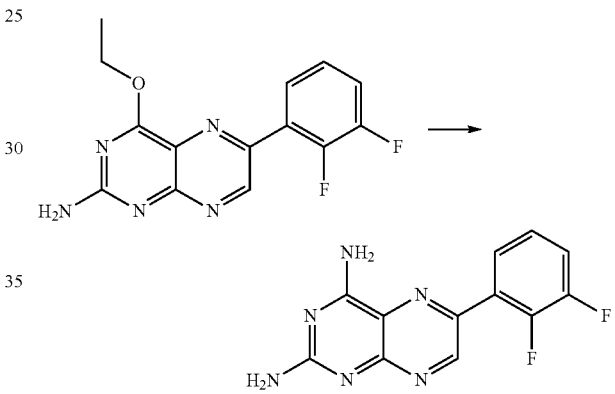

To a solution of 6-(2,3-difluoro-phenyl)-4-ethoxy-pteridin-2-ylamine (10 mg, 0.03 mmol) in MeOH (1 mL) was added 10 mL of a 30% aqueous ammonia solution. The mixture was microwave at 130° C. for 20 minutes. The precipitate formed was collected by filtration and washed with water and small amount of MeOH to provide 5 mg of the title compound as a yellow solid (62% yield), which characterized by mass spectrometry as follows: MS (m/z) 275.7 [M+H]⁺.

Example 144—Synthesis of (S)-2-amino-N-(4-(2-amino-4-morpholinopteridin-6-yl)phenyl)-3-hydroxypropanamide

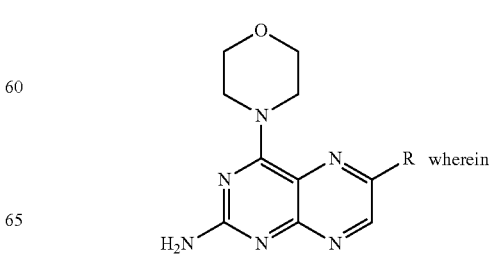

wherein

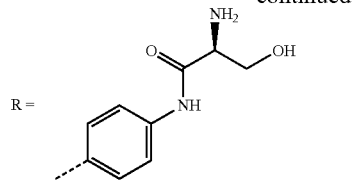

The compound of example 139 (12 mg, 0.023 mmol) was stirred in 20% TFA/DCM (2 mL) solution for 20 minutes. The solvent was removed in vacuo and the residue was purified by HPLC onto a C18 column with a gradient of H$_2$O, 0.1% TFA-acetonitrile, to provide the desired product which was characterized by mass spectrometry as follows: MS (m/z) 411.8 [M+H]$^+$.

Example 145—Synthesis of (S)-2-amino-N-(4-(2-amino-4-morpholinopteridin-6-yl)phenyl)-propanamide

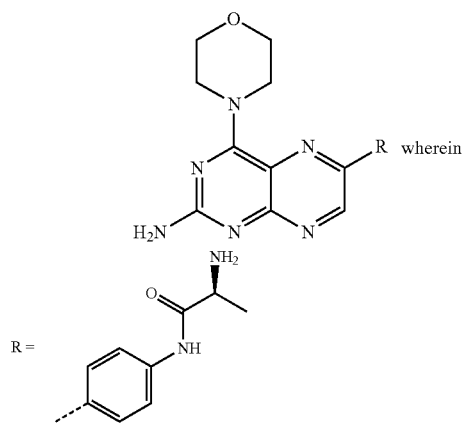

This product was prepared using the method of example 144 but starting from the compound of example 140. The resulting compound was characterized by mass spectrometry as follows: MS (m/z) 395.8 [M+H]$^+$.

Examples 146 to 163—Synthesis of 2-amino-4-alkoxy-6-(4-fluorophenyl)-pteridines

The scheme below shows a general procedure for the synthesis of 2-amino-4-alkoxy-6-(4-fluorophenyl)-pteridines.

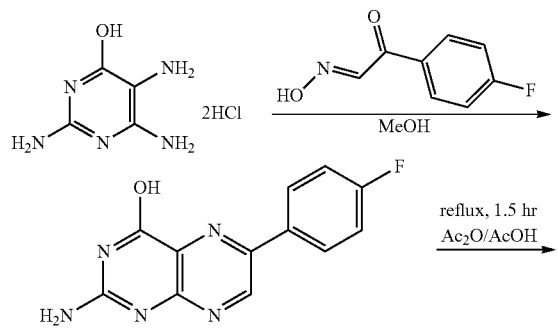

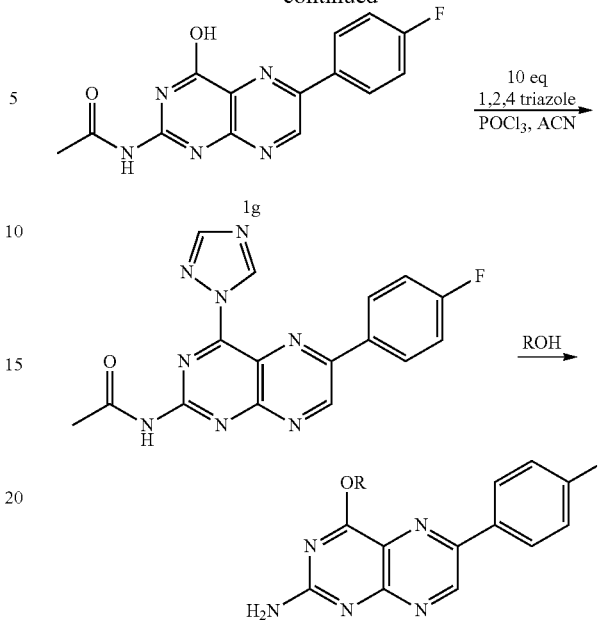

Synthesis of 2-amino-4-hydroxy-6-(4-fluorophenyl)pteridine (Example 146)

To a boiling solution of 2,5,6-triamino-4-hydroxypyrimidine dihydrochloride (2.75 g, 12.9 mmol) in methanol (80 mL) was added a solution of 4-fluorophenylglyoxal monooxime (2.58 g, 15.5 mmol) in methanol (20 mL). The reaction mixture was heated under reflux for 5 hours. The precipitate formed was filtered off, washed with water, then ethanol and diethyl ether, and dried under vacuum, providing the title compound as a yellow powder in 45% yield (1.5 g), which was characterized by mass spectrometry as follows: MS (m/z) 258.1 [M+H]$^+$.

Synthesis of 2-acetylamino-4-hydroxy-6-(4-fluorophenyl)pteridine (Example 147)

A suspension of 2-amino-6-(4-fluorophenyl)pteridine (1 g, 3.9 mmol) in acetic anhydride (60 mL) and acetic acid (20 mL) was refluxed for 90 minutes until a clear solution was formed. By cooling down the reaction mixture in the refrigerator, the precipitate formed was filtered off, washed with ethyl acetate and diethyl ether, and dried under vacuum, providing the title compound as a yellow powder in 87% yield (1.01 g), which was characterized by mass spectrometry as follows: MS (m/z) 300.1 [M+H]$^+$.

Synthesis of 2-acetylamino-4-(1,2,4-triazolyl)-6-(4-fluorophenyl)pteridine (Example 148)

To a suspension solution of 2-acetylamino-6-(4-fluorophenyl)pteridine (517 mg, 1.73 mmol), 1,2,4-triazole (1.19 g, 17.3 mmol), diisopropylethylamine (1.5 mL, 8.65 mmol) in acetonitrile (20 mL) was added dropwise phosphorus oxychloride (0.32 mL, 3.46 mmol). The suspension was stirred at room temperature for 3 days. The precipitated was filtered off, washed with large amount of acetonitrile and diethyl ether. The resulting solid was dried under vacuum, providing the title compound as a yellow powder in 80% yield (480 mg), which was characterized by mass spectrometry as follows: MS (m/z) 351.2 [M+H]+.

The general procedure used for preparing 2-amino-4-alkoxy-6-(4-fluorophenyl)-pteridines was as follows: Potassium t-butoxide (0.1 mL, 1.0 M solution in THF) was added to a solution of 2-acetylamino-4-(1,2,4-triazolyl)-6-(4-fluorophenyl)pteridine (35 mg, 0.1 mmol) in a suitable alcohol (0.5 mL). The resulting mixture was heated at 100° C. for 10 minutes under microwave irradiation. After cooling, the solution was concentrated in vacuo and the residue was purified by HPLC onto a C18 column with a gradient of H2O, 0.1% TFA-acetonitrile. This procedure provided, with yields ranging from 5% to 50%, depending upon the alkoxy group introduced at position 4 of the pteridine ring, the pure compounds, which were characterized by their mass spectrum as indicated in the following table 3.

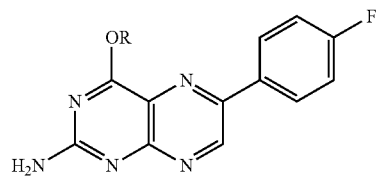

TABLE 3

| Example | R | Compound name | M + H |
|---|---|---|---|
| 149 | methyl | 6-(4-Fluorophenyl)-4-methoxy-pteridin-2-ylamine | 272.2 |
| 150 | isopropyl | 6-(4-Fluorophenyl)-4-isopropoxy-pteridin-2-ylamine | 300.1 |
| 151 | CH2CH2OMe | 6-(4-Fluorophenyl)-4-(2-methoxy-ethoxy)-pteridin-2-ylamine | 316.6 |
| 152 | n-butyl | 4-Butoxy-6-(4-fluorophenyl)-pteridin-2-ylamine | 314.2 |
| 153 | CH2CF3 | 6-(4-Fluorophenyl)-4-(2,2,2-trifluoro-ethoxy)-pteridin-2-ylamine | 340.1 |
| 154 | ⟨structure: CH2C(CH3)2CH2OH⟩ | 4-[2-Amino-6-(4-fluorophenyl)-pteridin-4-yloxy]-2-methyl-butan-2-ol | 344.2 |
| 155 | ⟨structure: CH2CH2-morpholine⟩ | 6-(4-Fluorophenyl)-4-(2-morpholin-4-yl-ethoxy)-pteridin-2-ylamine | 370.9 |
| 156 | ⟨structure: CH2CH2CH2-morpholine⟩ | 6-(4-Fluorophenyl)-4-(3-morpholin-4-yl-propoxy)-pteridin-2-ylamine | 385 |
| 157 | ⟨structure: CH2-cyclopropyl⟩ | 4-Cyclopropylmethoxy-6-(4-fluorophenyl)-pteridin-2-ylamine | 312.3 |
| 158 | ⟨structure: CH2-cyclobutyl⟩ | 4-Cyclobutylmethoxy-6-(4-fluorophenyl)-pteridin-2-ylamine | 326.2 |
| 159 | n-propyl | 6-(4-Fluorophenyl)-4-propoxy-pteridin-2-ylamine | 300.1 |
| 160 | sec-butyl | 4-sec-butoxy-6-(4-fluorophenyl)-pteridin-2-ylamine | 314.4 |
| 161 | ⟨structure: tetrahydrofuran-3-yl⟩ | 6-(4-Fluorophenyl)-4-(tetrahydro-furan-3-yloxy)-pteridin-2-ylamine | 328.2 |
| 162 | isobutyl | 6-(4-Fluorophenyl)-4-isobutoxy-pteridin-2-ylamine | 314.1 |
| 163 | benzyl | 4-Benzyloxy-6-(4-fluorophenyl)-pteridin-2-ylamine | 348.2 |

(end of table 3)

Example 164—Synthesis of 4-ethylthio-6-(4-fluorophenyl)-pteridin-2-ylamine

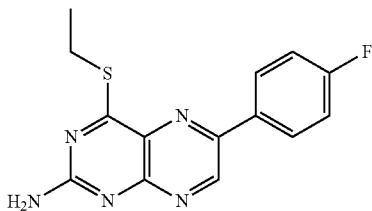 [SMILES: CCSc1nc(N)nc2ncc(-c3ccc(F)cc3)nc12]

This product, which was prepared according to a method similar to that of example 149, except for using sodium ethane-thiolate as reagent and ethanol, was characterized by mass spectrometry as follows: MS (m/z) 302.6 [M+H]$^+$.

Examples 165 to 176—Synthesis of 2-amino-4-alkylamino-6-(4-fluorophenyl)-pteridines The synthesis proceeds as follows:

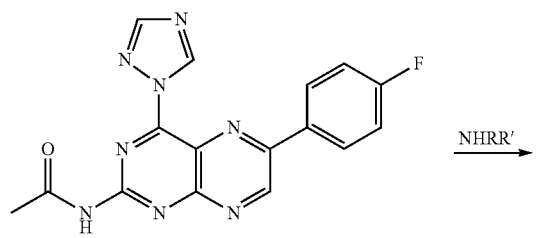

→ NHRR′ →

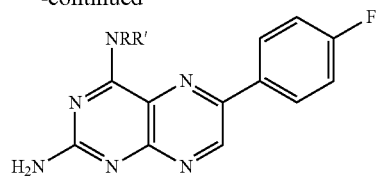

The general procedure used for preparing 2-amino-4-alkylamino-6-(4-fluorophenyl)-pteridines was as follows. Sodium methoxide (0.8 mL, 0.5 N solution in methanol) was added to a mixture of 2-acetylamino-4-(1,2,4-triazolyl)-6-(4-fluorophenyl)pteridine (35 mg, 0.1 mmol) and corresponding amines with the general formula NHRR′ (0.2 mL). The resulting mixture was heated at 100° C. for 10 minutes under microwave irradiation. After cooling, the solution was concentrated in vacuo and the residue was purified by HPLC onto a C18 column with a gradient of H$_2$O, 0.1% TFA-acetonitrile. This procedure provided, with yields ranging from 25% to 60%, depending upon the amino group introduced at position 4 of the pteridine ring, the pure compounds which were characterized by their mass spectrum MS as indicated in table 4 below.

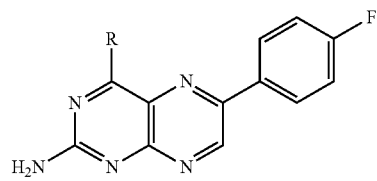

TABLE 4

| Example | R | Compound name | M + H |
|---|---|---|---|
| 165 | NH$_2$ | 4-amino-6-(4-fluorophenyl)-pteridine-2,4-diamine | 257.2 |
| 166 | piperidin-1-yl | 6-(4-Fluorophenyl)-4-piperidin-1-yl-pteridin-2-ylamine | 325.2 |
| 167 | NH-cyclopropyl | N-4-Cyclopropyl-6-(4-fluorophenyl)-pteridine-2,4-diamine | 297.1 |
| 168 | 2,6-dimethylmorpholin-4-yl | 4-(2,6-Dimethylmorpholin-4-yl)-6-(4-fluorophenyl)-pteridin-2-ylamine | 355.1 |
| 169 | NH-cyclohexyl | N-4-Cyclohexyl-6-(4-fluorophenyl)-pteridine-2,4-diamine | 339.2 |
| 170 | NH-benzyl | N-4-Benzyl-6-(4-fluorophenyl)-pteridine-2,4-diamine | 347.2 |

TABLE 4-continued

| Example | R | Compound name | M + H |
|---|---|---|---|
| 171 | 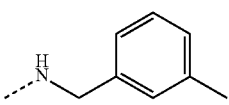 | N-4-(3-Methyl-benzyl)-6-(4-fluorophenyl)-pteridine-2,4-diamine | 347.2 |
| 172 | 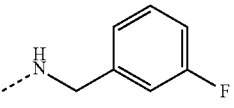 | N-4-(3-Fluorobenzyl)-6-(4-fluorophenyl)-pteridine-2,4-diamine | 351.2 |
| 173 | 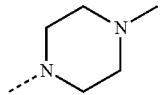 | 6-(4-Fluorophenyl)-4-(4-methylpiperazin-1-yl)-pteridin-2-ylamine | 340.2 |
| 174 | 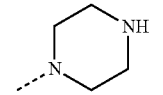 | 6-(4-Fluorophenyl)-4-piperazin-1-yl-pteridin-2-ylamine | 326.2 |
| 175 | 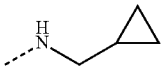 | N-4-Cyclopropylmethyl-6-(4-fluorophenyl)-pteridine-2,4-diamine | 311.2 |
| 176 |  | 6-(4-Fluorophenyl)-4-pyrrolidin-1-yl-pteridin-2-ylamine | 311.2 |

(end of table 4)

Examples 177 and 178

Synthesis of 6-(4-Fluorophenyl)-4-[1,2,4]triazol-1-yl-pteridine

Synthesis proceeded in two steps as shown in the following scheme:

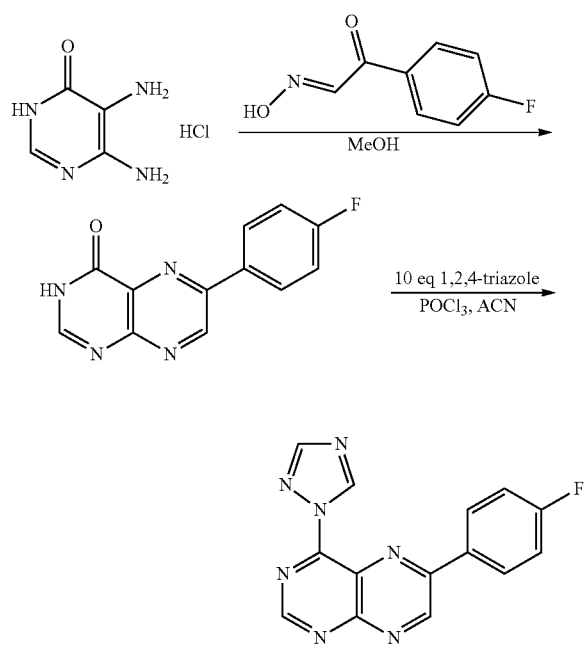

Synthesis of 6-(4-fluorophenyl)-3H-pteridin-4-one (Example 177)

To a boiling solution of 4,5-Diamino-6-hydroxy-pyrimidine hydrochloride (1.5 g, 9.23 mmol) in methanol (60 mL) was added a solution of 4-fluoropheynlglyoxal monooxime (2.0 g, 12 mmol) in methanol (20 mL). The reaction mixture was heated under reflux for 1 hour. After cooling, the precipitate formed was filtered off, washed with diethyl ether, and dried under vacuum, providing the title compound as a yellow powder in 68% yield (1.51 g) which was characterized by its mass spectrum as follows: MS (m/z) 243.4 [M+H]+.

Synthesis of 6-(4-fluorophenyl)-4-[1,2,4]triazol-1-yl-pteridine (Example 178)

To a solution of the compound of example 177 (250 mg, 1.03 mmol), 1,2,4-triazole (285 mg, 4.13 mmol) and diisopropylethylamine (0.72 mL, 4.13 mmol) in acetonitrile (8 mL) phosphorus oxychloride (0.24 mL, 2.58 mmol) was added dropwise. The suspension was stirred at room temperature for 3 days. The precipitated was filtered off, washed with large amount of acetonitrile and diethyl ether. The resulting solid was dried under vacuum, providing the title compound as a yellow powder in 99% yield (300 mg), which was characterized by mass spectrometry as follows: MS (m/z) 294.0 [M+H]+.

Examples 179 to 181—Synthesis of 4-alkoxy-6-(4-fluorophenyl)-pteridines

Synthesis proceeded as follows:

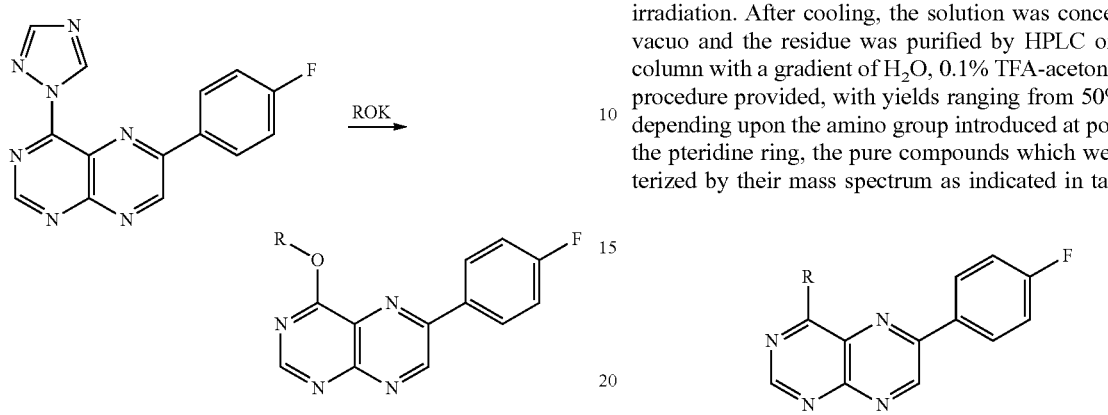

The general procedure used for preparing 4-alkoxy-6-(4-fluorophenyl)-pteridines was as follows. Potassium t-butoxide (0.1 mL, 1.0 M solution in THF) was added to a solution of 6-(4-fluorophenyl)-4-[1,2,4]triazol-1-yl-pteridine (30 mg, 0.1 mmol) in a suitable alcohol (0.5 mL). The resulting mixture was heated at 70° C. for 5 minutes under microwave irradiation. After cooling, the solution was concentrated in vacuo and the residue was purified by HPLC onto a C18 column with a gradient of $H_2O$, 0.1% TFA-acetonitrile. This procedure provided, with yields ranging from 25% to 70%, depending upon the alkoxy group introduced at position 4 of the pteridine ring, the pure compounds which were characterized by their mass spectrum MS as indicated in the following table 5.

TABLE 5

| Example | R | Compound name | M + H |
|---|---|---|---|
| 179 | ethyl | 4-ethoxy-6-(4fluorophenyl)pteridine | 271.2 |
| 180 | isopropyl | 4-isopropoxy-6-(4-fluorophenyl)-pteridine | 285.2 |
| 181 | $CH_2CH_2OMe$ | 4--(2-methoxy-ethoxy)-6-(4-fluoro-phenyl)-pteridine | 301.1 |

Examples 182 to 184—Synthesis of 4-amino-6-(4-fluorophenyl)-pteridines

The general procedure used for preparing 4-amino-6-(4-fluorophenyl)-pteridines was as follows. A mixture of (4-fluorophenyl)-4-[1,2,4]triazol-1-yl-pteridine (30 mg, 0.1 mmol) and a suitable amine (0.1 mL) in dioxane (0.5 mL) was heated at 100° C. for 7 minutes under microwave irradiation. After cooling, the solution was concentrated in vacuo and the residue was purified by HPLC onto a C18 column with a gradient of $H_2O$, 0.1% TFA-acetonitrile. This procedure provided, with yields ranging from 50% to 60%, depending upon the amino group introduced at position 4 of the pteridine ring, the pure compounds which were characterized by their mass spectrum as indicated in table 6.

TABLE 6

| Example | R | Compound name | M + H |
|---|---|---|---|
| 182 | H-N-cyclohexyl-CH3 | [6-(4-Fluoro-phenyl)-pteridin-4-yl]-(4-methyl-cyclohexyl)-amine, isomer A | 338.8 |
| 183 | H-N-cyclohexyl-CH3 | [6-(4-Fluoro-phenyl)-pteridin-4-yl]-(4-methyl-cyclohexyl)-amine, isomer B | 338.8 |
| 184 | morpholine | 6-(4-Fluoro-phenyl)-4-morpholin-4-yl-pteridine | 312.2 |

Example 185—Synthesis of 4-ethylthio-6-(4-fluorophenyl)-pteridine

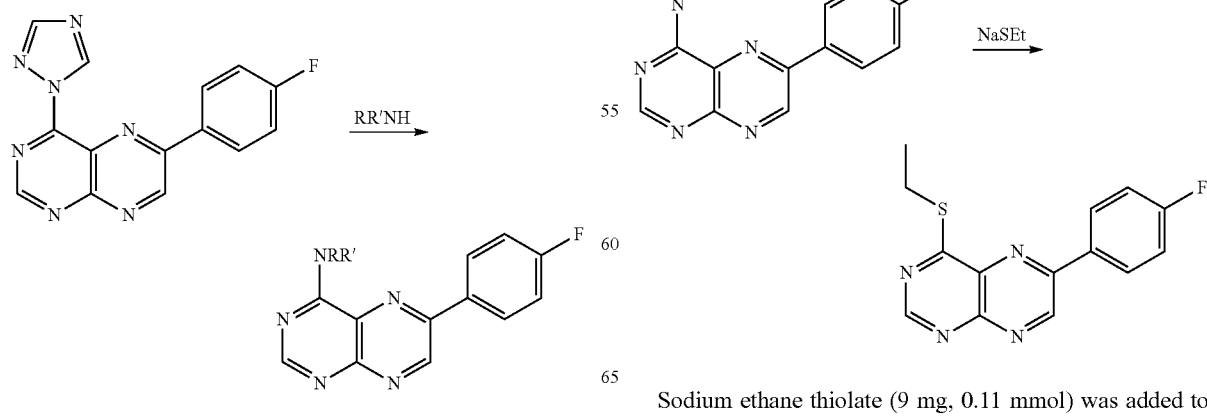

Sodium ethane thiolate (9 mg, 0.11 mmol) was added to a solution of (4-Fluoro-phenyl)-4-[1,2,4]triazol-1-yl-pteridine (30 mg, 0.1 mmol) in ethanol (0.5 mL). The resulting mixture was heated at 70° C. for 5 minutes under microwave irradiation. After cooling, the solution was concentrated in vacuo and the residue was purified by HPLC onto a C18 column with a gradient of $H_2O$, 0.1% TFA-acetonitrile, to provide 3.8 mg (yield 13%) of the desired product which was characterized by mass spectrometry as follows: MS (m/z) 287.2 $[M+H]^+$.

Example 186—Anti-HCV Assay/Replicon Assay

The anti HCV activity of specifically substituted pteridine derivatives was tested in a human hepatoma Huh-7 cell line harbouring a HCV replicon. The assay comprised the following steps:
Step 1: compound preparation and serial dilution involved the following alternatives, depending upon the water solubility of pteridine derivative being tested:
1. with respect to water soluble pteridine derivatives, 500 μL of solution in cell media (DMEM, 10% FBS, P/S, L-Glutamine) was prepared with a concentration that is twice the concentration of the starting final serial dilution concentration. 150 μL of the solution was added to the pre-specified wells in column 1 of a 96-well cell culture plate (PerkinElmer, white plate, cat. #6005181, for EC50 assay; black plate, cat. #6005182 for CC50 assay). The rest of the plate, i.e. columns 2-12, was filled with 100 μL of cell media. The plate was then placed on a Precision 2000 Workstation in order to start serial dilution. Pteridine compounds were diluted three times each step from column 1 to column 10. Column 11 was used as a blank control (no pteridine compound added).
2. With respect to poorly water soluble pteridine derivatives, DMSO was used as a solvent, and serial dilution was performed in 50% DMSO in water, in a 384-well plate. A solution containing the relevant compound at 100-fold the concentration of the starting final serial dilution concentration was prepared in 50% DMSO in water and added to the pre-specified wells in column 1 of a polypropylene 384-well plate. This plate was then placed on a Precision 2000 Workstation in order to start serial dilution. After serial dilution, 2 μL of the solution was transferred from the 384-well plate to a 96-well cell culture plate containing 100 μL of cell media on a Biomek FX Workstation. The DMSO concentration in the final assay condition was 0.5% after cells have been added to the plate and the total volume in each well was brought to 200 μL.
Step 2: to each well of the serial dilution plate prepared in step 1, 100 μL of cell media containing 6000 suspended Huh-7 HCV replicon cells was added with a Multidrop workstation. Plates were incubated for 3 days at 37° C. with 5% $CO_2$.
Step 3: detection:
1) with respect to the $EC_{50}$ assay, the media in a 96-well cell culture plate was aspirated with a Biotek EL405 plate-washer. A volume of 200 μL of a solution containing a 1:1 mixture of a cell-lysis buffer (commercially available from Promega, Luciferase Cell Culture Lysis 5X Reagent, cat. #E1531) and a luciferase substrate solution (commercially available from Promega, Luciferase Assay, cat. #E4550) was added to each well of the plate with Multidrop. The plate was incubated for 30 minutes at room temperature before the luminescence signal was measured with a TopCount plate-reader.
2) with respect to the $CC_{50}$ assay, 100 μL of a pre-mixed CellTiter-Glo (commercially available from Promega, cat. #G7572) solution was added directly to the cell culture in each well of the plate and the luminescence signal was measured with a TopCount plate-reader after 10 minutes of incubation at room temperature.

Table 7 shows $EC_{50}$ and $CC_{50}$ values determined in the above assay for 2-amino-pteridine derivatives synthesized according to the methods described in the examples above. Results are expressed by the following data:
- the 50% effective concentration ($EC_{50}$), i.e. the concentration that protects 50% of the cell monolayer from virus-induced cythopathic effect.
- the 50% cytostatic concentration ($CC_{50}$), i.e. the concentration that results in 50% inhibition of cell growth.

TABLE 7

| Example | $EC_{50}$ (A < 0.3 μM; 0.3 μM < B < 1 μM; 1 μM < C < 10 μM) | $CC_{50}$ (A < 10 μM; B 10-20 μM; C > 20 μM) |
|---|---|---|
| 3 | C | C |
| 27 | B | A |
| 30 | C | C |
| 31 | B | A |
| 54 | C | C |
| 57 | C | C |
| 69 | C | C |
| 78 | B | A |
| 79 | B | A |
| 80 | B | C |
| 82 | B | C |
| 84 | A | A |
| 85 | C | C |
| 86 | B | B |
| 89 | C | C |
| 90 | B | C |
| 91 | B | C |
| 92 | B | B |
| 93 | C | B |
| 95 | C | B |
| 108 | B | B |
| 109 | C | B |
| 110 | C | C |
| 111 | C | C |
| 112 | C | C |
| 113 | C | C |
| 114 | C | C |
| 120 | C | B |
| 121 | C | B |
| 123 | B | A |
| 126 | C | B |
| 127 | B | A |
| 129 | A | A |
| 130 | C | C |
| 133 | B | C |
| 136 | C | B |
| 137 | A | B |
| 138 | C | B |
| 140 | C | A |
| 142 | B | A |
| 143 | C | B |
| 144 | C | C |
| 145 | B | C |
| 149 | B | C |
| 150 | A | C |
| 152 | C | C |
| 154 | C | C |
| 157 | C | C |
| 159 | C | C |
| 164 | B | C |

(end of table 7)

Examples 200 to 395—Synthesis of 2-amino-4-morpholino-6-(2-fluorophenyl)pteridine Analogues The experimental procedure of example 77 is repeated, except that other arylboronic acids or heteroarylboronic acids, or esters thereof, are used instead of 2-fluorophenylboronic acid. In this way the following compounds are obtained in similar yields:

4-morpholino-6-(4-(4'-allyloxycarbonylpiperazino)phenyl)pteridin-2-ylamine,
4-morpholino-6-(3-aminocarbonylphenyl)pteridin-2-ylamine,
4-morpholino-6-(4-aminocarbonylphenyl)pteridin-2-ylamine,
4-morpholino-6-(2-amino-5-chlorophenyl)pteridin-2-ylamine,
4-morpholino-6-(4-amino-3-methoxyphenyl)pteridin-2-ylamine,
4-morpholino-6-(2-amino-4-methylphenyl)pteridin-2-ylamine,
4-morpholino-6-(2-amino-5-methylphenyl)pteridin-2-ylamine,
4-morpholino-6-(4-amino-2-methyl phenyl)pteridin-2-ylamine,
4-morpholino-6-(5-amino-2-methyl phenyl)pteridin-2-ylamine,
4-morpholino-6-(4-amino-3-nitrophenyl)pteridin-2-ylamine,
4-morpholino-6-(2-benzyloxyphenyl)pteridin-2-ylamine,
4-morpholino-6-(3-benzyloxy-4-methoxyphenyl)pteridin-2-ylamine,
4-morpholino-6-(4-biphenyl)pteridin-2-ylamine,
4-morpholino-6-(4-n-butyl phenyl)pteridin-2-ylamine,
4-morpholino-6-(4-isobutylphenyl)pteridin-2-ylamine,
4-morpholino-6-(4-carboxy-3-fluorophenyl)pteridin-2-ylamine,
4-morpholino-6-(3-(3-carboxypropionylamino)phenyl)pteridin-2-ylamine,
4-morpholino-6-(4-(3-carboxypropionylamino)phenyl)pteridin-2-ylamine,
4-morpholino-6-(3-chloro-4-hydroxy-5-methoxyphenyl)pteridin-2-ylamine,
4-morpholino-6-(2-chloro-5-hydroxymethylphenyl)pteridin-2-ylamine,
4-morpholino-6-(4-cyanomethoxyphenyl)pteridin-2-ylamine,
4-morpholino-6-(3-cyanomethoxyphenyl)pteridin-2-ylamine,
4-morpholino-6-(2-cyanomethoxyphenyl)pteridin-2-ylamine,
4-morpholino-6-(4-cyanophenyl)pteridin-2-ylamine,
4-morpholino-6-(3-cyanophenyl)pteridin-2-ylamine,
4-morpholino-6-(2-cyanophenyl)pteridin-2-ylamine,
4-morpholino-6-(3-(N-cyclopropylaminocarbonyl)phenyl)pteridin-2-ylamine,
4-morpholino-6-(3-(N,N-diethylaminocarbonyl)phenyl)pteridin-2-ylamine,
4-morpholino-6-(3-(N,N-dimethylamino)phenyl)pteridin-2-ylamine,
4-morpholino-6-(2-(N,N-dimethylamino)phenyl)pteridin-2-ylamine,
4-morpholino-6-(3-(N,N-dimethylaminocarbonyl)phenyl)pteridin-2-ylamine,
4-morpholino-6-(3-[(N',N'-dimethylamino)ethylaminocarbonyl]phenyl)-pteridin-2-ylamine,
4-morpholino-6-(4-[(N',N'-dimethylamino)ethylaminocarbonyl]phenyl)-pteridin-2-ylamine,
4-morpholino-6-(3-[1,3]dioxolan-2-ylmethoxyphenyl)pteridin-2-ylamine,
4-morpholino-6-(3-(ethoxycarbonyl)methoxyphenyl)pteridin-2-ylamine,
4-morpholino-6-(4-(ethoxycarbonyl)methoxyphenyl)pteridin-2-ylamine,
4-morpholino-6-(4-ethoxycarbonylphenyl)pteridin-2-ylamine,
4-morpholino-6-(3-ethoxycarbonylphenyl)pteridin-2-ylamine,
4-morpholino-6-(2-ethoxycarbonylphenyl)pteridin-2-ylamine,
4-morpholino-6-(4-(3-ethoxycarbonylpiperidino)carboxamidophenyl)-pteridin-2-ylamine,
4-morpholino-6-(4-formylaminophenyl)pteridin-2-ylamine,
4-morpholino-6-(3-formylaminophenyl)pteridin-2-ylamine,
4-morpholino-6-(2-formylaminophenyl)pteridin-2-ylamine,
4-morpholino-6-(2-formyl-5-methoxyphenyl)pteridin-2-ylamine,
4-morpholino-6-(3-formyl-4-methoxyphenyl)pteridin-2-ylamine,
4-morpholino-6-(5-formyl-2-methoxyphenyl)pteridin-2-ylamine,
4-morpholino-6-(2-formyl-5-methylphenyl)pteridin-2-ylamine,
4-morpholino-6-(4--formylphenyl)pteridin-2-ylamine,
4-morpholino-6-(3-formylphenyl)pteridin-2-ylamine,
4-morpholino-6-(2-formylphenyl)pteridin-2-ylamine,
4-morpholino-6-(4-hydroxy-3,5-dimethylphenyl)pteridin-2-ylamine,
4-morpholino-6-(3-(2-hydroxyethyl)-aminocarbonylphenyl)pteridin-2-ylamine,
4-morpholino-6-(4-(2-hydroxyethyl)aminocarbonyl)phenyl)pteridin-2-ylamine,
4-morpholino-6-(3-hydroxy-4-methoxycarbonylphenyl)pteridin-2-ylamine,
4-morpholino-6-(4-hydroxy-3-methoxyphenyl)pteridin-2-ylamine,
4-morpholino-6-(4-(hydroxymethyl)phenyl)pteridin-2-ylamine,
4-morpholino-6-(3-(hydroxymethyl)phenyl)pteridin-2-ylamine,
4-morpholino-6-(4-hydroxy-3-nitrophenyl)pteridin-2-ylamine,
4-morpholino-6-(4-isopropoxyphenyl)pteridin-2-ylamine,
4-morpholino-6-(4-(4-isopropylpiperazinyl)phenyl)pteridin-2-ylamine,
4-morpholino-6-(4-isopropylphenyl)pteridin-2-ylamine,
4-morpholino-6-(4-methanesulfonamidophenyl)pteridin-2-ylamine,
4-morpholino-6-(3-methanesulfonamidophenyl)pteridin-2-ylamine,
4-morpholino-6-(2-methanesulfonamido phenyl)pteridin-2-ylamine,
4-morpholino-6-(4-methoxycarbonylphenyl)pteridin-2-ylamine,
4-morpholino-6-(3-methoxycarbonylphenyl)pteridin-2-ylamine,
4-morpholino-6-(2-methoxycarbonylphenyl)pteridin-2-ylamine,
4-morpholino-6-(3-methoxy-4-methoxycarbonylphenyl)pteridin-2-ylamine,
4-morpholino-6-(2-methoxy-5-methylphenyl)pteridin-2-ylamine,
4-morpholino-6-(4-methoxy-3-nitrophenyl)pteridin-2-ylamine,
4-morpholino-6-(4-methoxyphenyl)pteridin-2-ylamine,
4-morpholino-6-(3-methoxyphenyl)pteridin-2-ylamine,
4-morpholino-6-(4-N-methylcarboxamidophenyl)pteridin-2-ylamine, 4-morpholino-6-(4-(N-methylamino)phenyl)pteridin-2-ylamine,
4-morpholino-6-(3-(4-methylpiperazine-1-carbonyl)phenyl)pteridin-2-ylamine,
4-morpholino-6-(4-(4-methylpiperazine-1-carbonyl)phenyl)pteridin-2-ylamine,
4-morpholino-6-(4-(methylthio)phenyl)pteridin-2-ylamine,
4-morpholino-6-(3-(methylthio)phenyl)pteridin-2-ylamine,
4-morpholino-6-(2-(methylthio)phenyl)pteridin-2-ylamine,
4-morpholino-6-(4-(morpholinocarbonyl)phenyl)pteridin-2-ylamine,
4-morpholino-6-(4-morpholinophenyl)pteridin-2-ylamine,
4-morpholino-6-(2-(morpholinomethyl)phenyl)pteridin-2-ylamine,
4-morpholino-6-(4-nitrophenyl)pteridin-2-ylamine,
4-morpholino-6-(3-nitrophenyl)pteridin-2-ylamine,
4-morpholino-6-(2-nitrophenyl)pteridin-2-ylamine,
4-morpholino-6-(4-phenoxyphenyl)pteridin-2-ylamine,
4-morpholino-6-(4-(N-phenylaminomethyl)phenyl)pteridin-2-ylamine,
4-morpholino-6-(4-(phenylcarbonyl)phenyl)pteridin-2-ylamine,
4-morpholino-6-(4-(piperazine-1-carbonyl)phenyl)pteridin-2-ylamine,
4-morpholino-6-(4-piperazinylphenyl)pteridin-2-ylamine,
4-morpholino-6-(4-succinamidophenyl)pteridin-2-ylamine,
4-morpholino-6-(3-succinamidophenyl)pteridin-2-ylamine,
4-morpholino-6-(sulfamoylphenyl)pteridin-2-ylamine,
4-morpholino-6-(2-(toluene-4-sulfonamido)phenyl)pteridin-2-ylamine,
4-morpholino-6-(4-(toluene-4-sulfonamido)phenyl)pteridin-2-ylamine,
4-morpholino-6-(4-(tert-butoxycarbonylamino)-3-methoxyphenyl)pteridin-2-ylamine,
4-morpholino-6-(2-(tert-butoxycarbonyl)phenyl)pteridin-2-ylamine,
4-morpholino-6-(3-(tert-butoxycarbonyl)phenyl)pteridin-2-ylamine,
4-morpholino-6-(4-(tert-butoxycarbonyl)phenyl)pteridin-2-ylamine,
4-morpholino-6-(2,3,4-trifluorophenyl)pteridin-2-ylamine,
4-morpholino-6-(4-tert-butylphenyl)pteridin-2-ylamine,
4-morpholino-6-(4-(tetrahydro-2H-pyran-2-yloxy)phenyl)pteridin-2-ylamine,
4-morpholino-6-(4-(2-thienyl)phenyl)pteridin-2-ylamine,
4-morpholino-6-(2,4,6-trimethylphenyl)pteridin-2-ylamine,
4-morpholino-6-(3,4,5-trimethoxyphenyl)pteridin-2-ylamine,
4-morpholino-6-(4-vinylphenyl)pteridin-2-ylamine,
4-morpholino-6-(4-(2-hydroxyethoxy)phenyl)pteridin-2-ylamine,
4-morpholino-6-(6-benzyloxynaphth-2-yl)pteridin-2-ylamine,
4-morpholino-6-(naphth-1-yl)pteridin-2-ylamine,
4-morpholino-6-(naphth-2-yl)pteridin-2-ylamine,
4-morpholino-6-(4'-benzoyl[1,1'-biphenyl]-4-yl)pteridin-2-ylamine,
4-morpholino-6-(1-biphenylyl)pteridin-2-ylamine,
4-morpholino-6-(oxoindan-5-yl)pteridin-2-ylamine,
4-morpholino-6-(benzodioxolyl)pteridin-2-ylamine,
4-morpholino-6-(2-acetamidopyridin-5-yl)pteridin-2-ylamine,
4-morpholino-6-(2-aminopyridin-5-yl)pteridin-2-ylamine,
4-morpholino-6-(2-aminopyrimidin-5-yl)pteridin-2-ylamine,
4-morpholino-6-(1,4-benzodioxan-6-yl)pteridin-2-ylamine,
4-morpholino-6-(1-benzothien-3-yl)pteridin-2-ylamine,
4-morpholino-6-(2-benzyloxypyridin-5-yl)pteridin-2-ylamine,
4-morpholino-6-(1-benzyl-1H-pyrazol-4-yl)pteridin-2-ylamine,
4-morpholino-6-(2-bromo-3-chloropyridin-4-yl)pteridin-2-ylamine,
4-morpholino-6-(5-bromo-2,3-dihydrobenzo[b]furan-7-yl)pteridin-2-ylamine,
4-morpholino-6-(2-bromo-3-methylpyridin-5-yl)pteridin-2-ylamine,
4-morpholino-6-(2-bromopyridin-5-yl)pteridin-2-ylamine,
4-morpholino-6-(3-bromopyridin-5-yl)pteridin-2-ylamine,
4-morpholino-6-(5-bromothien-2-yl)pteridin-2-ylamine,
4-morpholino-6-(2-chloro-6-isopropylpyridin-3-yl)pteridin-2-ylamine,
4-morpholino-6-(2-chloro-3-methylpyridin-5-yl)pteridin-2-ylamine,
4-morpholino-6-(2-[4-(4-chlorophenylsulfonyl)piperazin-1-yl]pyridin-5-yl)pteridin-2-ylamine,
4-morpholino-6-(2-chloropyrid-4-yl)pteridin-2-ylamine,
4-morpholino-6-(2-chloropyrid-5-yl)pteridin-2-ylamine,
4-morpholino-6-(dibenzo[b,d]furan-4-yl)pteridin-2-ylamine,
4-morpholino-6-(2-chloro-3-fluoropyridin-4-yl)pteridin-2-ylamine,
4-morpholino-6-(dibenzo[b,d]thien-4-yl)pteridin-2-ylamine,
4-morpholino-6-(3,4-dihydro-2H-1,5-benzodioxepin-7-yl)pteridin-2-ylamine,
4-morpholino-6-(3,6-dihydro-2H-pyridine-1-tert-butoxycarbonyl)pteridin-2-ylamine,
4-morpholino-6-(2,5-dibromopyridin-3-yl)pteridin-2-ylamine,
4-morpholino-6-(2,6-dichloropyridin-3-yl)pteridin-2-ylamine,
4-morpholino-6-(2,3-dihydro-1-benzofuran-5-yl)pteridin-2-ylamine,
4-morpholino-6-(2,6-dimethoxypyridin-5-yl)pteridin-2-ylamine,
4-morpholino-6-(2,6-dimethoxypyridin-3-yl)pteridin-2-ylamine,
4-morpholino-6-(2,4-dimethoxypyrimidin-5-yl)pteridin-2-ylamine,
4-morpholino-6-(3,5-dimethylisoxazol-4-yl)pteridin-2-ylamine,
4-morpholino-6-(2-(3-N,N-dimethylaminopropoxy)pyridin-5-yl)pteridin-2-ylamine,
4-morpholino-6-(3,5-dimethylpyrazol-4-yl)pteridin-2-ylamine,
4-morpholino-6-(1-[1,3]dioxolan-2-ylmethyl-1H-pyrazol-4-yl)pteridin-2-ylamine,
4-morpholino-6-(2,4-dioxo-1,2,3,4-tetrahydro-5-pyrimidinyl)pteridin-2-ylamine,
4-morpholino-6-(2,4-di(tert-butoxy)pyrimidin-5-yl)pteridin-2-ylamine,
4-morpholino-6-(2-ethoxypyridin-3-yl)pteridin-2-ylamine,
4-morpholino-6-(2-fluoro-3-methylpyridin-5-yl)pteridin-2-ylamine,
4-morpholino-6-(2-fluoropyridin-5-yl)pteridin-2-ylamine,
4-morpholino-6-(5-formyl-2-furyl)pteridin-2-ylamine,
4-morpholino-6-(5-formylthien-2-yl)pteridin-2-ylamine,
4-morpholino-6-(furan-2-yl)pteridin-2-ylamine,
4-morpholino-6-(2-hydroxypyridin-5-yl)pteridin-2-ylamine,
4-morpholino-6-(1-isobutyl-1H-pyrazol-4-yl)pteridin-2-ylamine,
4-morpholino-6-(isoquinolin-4-yl)pteridin-2-ylamine, 4-morpholino-6-(2-methoxypyridin-3-yl)pteridin-2-ylamine,
4-morpholino-6-(2-methoxypyrimidin-5-yl)pteridin-2-ylamine,
4-morpholino-6-(5-methyl-1-benzothien-2-yl)pteridin-2-ylamine,
4-morpholino-6-(1-(3-methylbutyl)-1H-pyrazol-4-yl)pteridin-2-ylamine,
4-morpholino-6-(5-methylfuran-2-yl)pteridin-2-ylamine,
4-morpholino-6-(1-methylindol-5-yl)pteridin-2-ylamine,
4-morpholino-6-(5-methyl-3-phenyl-4-isoxazolyl)pteridin-2-ylamine,
4-morpholino-6-(5-(methylthio)thien-2-yl)pteridin-2-ylamine,
4-morpholino-6-(2-(4-methylpiperazinyl)pyridin-4-yl)pteridin-2-ylamine,
4-morpholino-6-(2-(4-methylpiperazinyl)pyridin-5-yl)pteridin-2-ylamine,
4-morpholino-6-(1-methyl-1H-pyrazol-4-yl)pteridin-2-ylamine,
4-morpholino-6-(3-methylpyridin-2-yl)pteridin-2-ylamine,
4-morpholino-6-(5-methylpyridin-2-yl)pteridin-2-ylamine,
4-morpholino-6-(5-methylpyridin-3-yl)pteridin-2-ylamine,
4-morpholino-6-(2-methoxypyridin-5-yl)pteridin-2-ylamine,
4-morpholino-6-(4-methylthien-2-yl)pteridin-2-ylamine,
4-morpholino-6-(5-methylthien-2-yl)pteridin-2-ylamine,
4-morpholino-6-(2-(2-morpholinoethylamino)-pyridin-5-yl)pteridin-2-ylamine,
4-morpholino-6-(2-(2-morpholinoethyl)-1H-pyrazol-4-yl)pteridin-2-ylamine,
4-morpholino-6-(2-(morpholin-1-yl)-pyridin-5-yl)pteridin-2-ylamine,
4-morpholino-6-(1-(phenylsulfonyl)-1H-indol-3-yl)pteridin-2-ylamine,
4-morpholino-6-(5-phenyl-2-thienyl)pteridin-2-ylamine,
4-morpholino-6-(2-(piperazin-1-yl)-pyridin-5-yl)pteridin-2-ylamine,
4-morpholino-6-(2-(piperazin-1-yl)-pyridin-4-yl)pteridin-2-ylamine,
4-morpholino-6-(1-propyl-1H-pyrazol-4-yl)pteridin-2-ylamine,
4-morpholino-6-(pyrazol-4-yl)pteridin-2-ylamine,
4-morpholino-6-(pyridin-4-yl)pteridin-2-ylamine,
4-morpholino-6-(4-phenoxathiinyl)pteridin-2-ylamine,
4-morpholino-6-(quinolin-8-yl)pteridin-2-ylamine,
4-morpholino-6-(quinolin-3-yl)pteridin-2-ylamine,
4-morpholino-6-(2-(4-tert-butoxycarbonylpiperazinyl)-pyrid-4-yl)pteridin-2-ylamine,
4-morpholino-6-(1-tert-butoxycarbonyl-1H-pyrazol-4-yl)pteridin-2-ylamine,
4-morpholino-6-(1-tert-butoxycarbonyl-2-pyrrolyl)pteridin-2-ylamine,
4-morpholino-6-(1-(tert-butoxycarbonyl)-5-bromo-1H-indol-2-yl)pteridin-2-ylamine,
4-morpholino-6-(1-(tert-butoxycarbonyl)-1H-indol-5-yl)pteridin-2-ylamine,
4-morpholino-6-(1-(tert-butoxycarbonyl)-5-methoxy-1H-indol-2-yl)pteridin-2-ylamine,
4-morpholino-6-(1-thianthrenylthien-3-yl)pteridin-2-ylamine, and
4-morpholino-6-(1,3,5-trimethyl-1H-pyrazol-4-yl)pteridin-2-ylamine.

Examples 400 to 595—Synthesis of 4-ethoxy-6-(2-fluorophenyl)pteridin-2-ylamine Analogues The experimental procedure of example 10 is repeated, except that other arylboronic acids or heteroarylboronic acids, or esters thereof, are used instead of 2-fluorophenylboronic acid. In this way the following compounds are obtained in similar yields:
4-ethoxy-6-(4-(4'-allyloxycarbonylpiperazino)phenyl)pteridin-2-ylamine,
4-ethoxy-6-(3-aminocarbonylphenyl)pteridin-2-ylamine,
4-ethoxy-6-(4-aminocarbonylphenyl)pteridin-2-ylamine,
4-ethoxy-6-(2-amino-5-chlorophenyl)pteridin-2-ylamine,
4-ethoxy-6-(4-amino-3-methoxyphenyl)pteridin-2-ylamine,
4-ethoxy-6-(2-amino-4-methylphenyl)pteridin-2-ylamine,
4-ethoxy-6-(2-amino-5-methylphenyl)pteridin-2-ylamine,
4-ethoxy-6-(4-amino-2-methyl phenyl)pteridin-2-ylamine,
4-ethoxy-6-(5-amino-2-methyl phenyl)pteridin-2-ylamine,
4-ethoxy-6-(4-amino-3-nitrophenyl)pteridin-2-ylamine,
4-ethoxy-6-(2-benzyloxyphenyl)pteridin-2-ylamine,
4-ethoxy-6-(3-benzyloxy-4-methoxyphenyl)pteridin-2-ylamine,
4-ethoxy-6-(4-biphenyl)pteridin-2-ylamine,
4-ethoxy-6-(4-n-butyl phenyl)pteridin-2-ylamine,
4-ethoxy-6-(4-isobutylphenyl)pteridin-2-ylamine,
4-ethoxy-6-(4-carboxy-3-fluorophenyl)pteridin-2-ylamine,
4-ethoxy-6-(3-(3-carboxypropionylamino)phenyl)pteridin-2-ylamine,
4-ethoxy-6-(4-(3-carboxypropionylamino)phenyl)pteridin-2-ylamine,
4-ethoxy-6-(3-chloro-4-hydroxy-5-methoxyphenyl)pteridin-2-ylamine,
4-ethoxy-6-(2-chloro-5-hydroxymethylphenyl)pteridin-2-ylamine,
4-ethoxy-6-(4-cyanomethoxyphenyl)pteridin-2-ylamine,
4-ethoxy-6-(3-cyanomethoxyphenyl)pteridin-2-ylamine,
4-ethoxy-6-(2-cyanomethoxyphenyl)pteridin-2-ylamine,
4-ethoxy-6-(4-cyanophenyl)pteridin-2-ylamine,
4-ethoxy-6-(3-cyanophenyl)pteridin-2-ylamine,
4-ethoxy-6-(2-cyanophenyl)pteridin-2-ylamine,
4-ethoxy-6-(3-(N-cyclopropylaminocarbonyl)phenyl)pteridin-2-ylamine,
4-ethoxy-6-(3-(N,N-diethylaminocarbonyl)phenyl)pteridin-2-ylamine,
4-ethoxy-6-(3-(N,N-dimethylamino)phenyl)pteridin-2-ylamine,
4-ethoxy-6-(2-(N,N-dimethylamino)phenyl)pteridin-2-ylamine,
4-ethoxy-6-(3-(N,N-dimethylaminocarbonyl)phenyl)pteridin-2-ylamine,
4-ethoxy-6-(3-[(N',N'-dimethylamino)ethylaminocarbonyl]phenyl)-pteridin-2-ylamine,
4-ethoxy-6-(4-[(N',N'-dimethylamino)ethylaminocarbonyl]phenyl)-pteridin-2-ylamine,
4-ethoxy-6-(3-[1,3]dioxolan-2-ylmethoxyphenyl)pteridin-2-ylamine,
4-ethoxy-6-(3-(ethoxycarbonyl)methoxyphenyl)pteridin-2-ylamine,
4-ethoxy-6-(4-(ethoxycarbonyl)methoxyphenyl)pteridin-2-ylamine,
4-ethoxy-6-(4-ethoxycarbonylphenyl)pteridin-2-ylamine,
4-ethoxy-6-(3-ethoxycarbonylphenyl)pteridin-2-ylamine,
4-ethoxy-6-(2-ethoxycarbonylphenyl)pteridin-2-ylamine,
4-ethoxy-6-(4-(3-ethoxycarbonylpiperidino)carboxamidophenyl)-pteridin-2-ylamine,
4-ethoxy-6-(4-formylaminophenyl)pteridin-2-ylamine,
4-ethoxy-6-(3-formylaminophenyl)pteridin-2-ylamine,
4-ethoxy-6-(2-formylaminophenyl)pteridin-2-ylamine,
4-ethoxy-6-(2-formyl-5-methoxyphenyl)pteridin-2-ylamine,
4-ethoxy-6-(3-formyl-4-methoxyphenyl)pteridin-2-ylamine, 4-ethoxy-6-(5-formyl-2-methoxyphenyl)pteridin-2-ylamine,
4-ethoxy-6-(2-formyl-5-methylphenyl)pteridin-2-ylamine,
4-ethoxy-6-(4-formylphenyl)pteridin-2-ylamine,
4-ethoxy-6-(3-formylphenyl)pteridin-2-ylamine,
4-ethoxy-6-(2-formylphenyl)pteridin-2-ylamine,
4-ethoxy-6-(4-hydroxy-3,5-dimethylphenyl)pteridin-2-ylamine,
4-ethoxy-6-(3-(2-hydroxyethyl)-aminocarbonylphenyl)pteridin-2-ylamine,
4-ethoxy-6-(4-(2-hydroxyethyl)aminocarbonyl)phenyl)pteridin-2-ylamine,
4-ethoxy-6-(3-hydroxy-4-methoxycarbonylphenyl)pteridin-2-ylamine,
4-ethoxy-6-(4-hydroxy-3-methoxyphenyl)pteridin-2-ylamine,
4-ethoxy-6-(4-(hydroxymethyl)phenyl)pteridin-2-ylamine,
4-ethoxy-6-(3-(hydroxymethyl)phenyl)pteridin-2-ylamine,
4-ethoxy-6-(4-hydroxy-3-nitrophenyl)pteridin-2-ylamine,
4-ethoxy-6-(4-isopropoxyphenyl)pteridin-2-ylamine,
4-ethoxy-6-(4-(4-isopropylpiperazinyl)phenyl)pteridin-2-ylamine,
4-ethoxy-6-(4-isopropylphenyl)pteridin-2-ylamine,
4-ethoxy-6-(4-methanesulfonamidophenyl)pteridin-2-ylamine,
4-ethoxy-6-(3-methanesulfonamidophenyl)pteridin-2-ylamine,
4-ethoxy-6-(2-methanesulfonamido phenyl)pteridin-2-ylamine,
4-ethoxy-6-(4-methoxycarbonylphenyl)pteridin-2-ylamine,
4-ethoxy-6-(3-methoxycarbonylphenyl)pteridin-2-ylamine,
4-ethoxy-6-(2-methoxycarbonylphenyl)pteridin-2-ylamine,
4-ethoxy-6-(3-methoxy-4-methoxycarbonylphenyl)pteridin-2-ylamine,
4-ethoxy-6-(2-methoxy-5-methylphenyl)pteridin-2-ylamine,
4-ethoxy-6-(4-methoxy-3-nitrophenyl)pteridin-2-ylamine,
4-ethoxy-6-(4-methoxyphenyl)pteridin-2-ylamine,
4-ethoxy-6-(3-methoxyphenyl)pteridin-2-ylamine,
4-ethoxy-6-(4-N-methylcarboxamidophenyl)pteridin-2-ylamine,
4-ethoxy-6-(4-(N-methylamino)phenyl)pteridin-2-ylamine,
4-ethoxy-6-(3-(4-methylpiperazine-1-carbonyl)phenyl)pteridin-2-ylamine,
4-ethoxy-6-(4-(4-methylpiperazine-1-carbonyl)phenyl)pteridin-2-ylamine,
4-ethoxy-6-(4-(methylthio)phenyl)pteridin-2-ylamine,
4-ethoxy-6-(3-(methylthio)phenyl)pteridin-2-ylamine,
4-ethoxy-6-(2-(methylthio)phenyl)pteridin-2-ylamine,
4-ethoxy-6-(4-(morpholinocarbonyl)phenyl)pteridin-2-ylamine,
4-ethoxy-6-(4-morpholinophenyl)pteridin-2-ylamine,
4-ethoxy-6-(2-(morpholinomethyl)phenyl)pteridin-2-ylamine,
4-ethoxy-6-(4-nitrophenyl)pteridin-2-ylamine,
4-ethoxy-6-(3-nitrophenyl)pteridin-2-ylamine,
4-ethoxy-6-(2-nitrophenyl)pteridin-2-ylamine,
4-ethoxy-6-(4-phenoxyphenyl)pteridin-2-ylamine,
4-ethoxy-6-(4-(N-phenylaminomethyl)phenyl)pteridin-2-ylamine,
4-ethoxy-6-(4-(phenylcarbonyl)phenyl)pteridin-2-ylamine,
4-ethoxy-6-(4-(piperazine-1-carbonyl)phenyl)pteridin-2-ylamine,
4-ethoxy-6-(4-piperazinylphenyl)pteridin-2-ylamine,
4-ethoxy-6-(4-succinamidophenyl)pteridin-2-ylamine,
4-ethoxy-6-(3-succinamidophenyl)pteridin-2-ylamine,
4-ethoxy-6-(sulfamoylphenyl)pteridin-2-ylamine,
4-ethoxy-6-(2-(toluene-4-sulfonamido)phenyl)pteridin-2-ylamine,
4-ethoxy-6-(4-(toluene-4-sulfonamido)phenyl)pteridin-2-ylamine,
4-ethoxy-6-(4-(tert-butoxycarbonylamino)-3-methoxyphenyl)pteridin-2-ylamine,
4-ethoxy-6-(2-(tert-butoxycarbonyl)phenyl)pteridin-2-ylamine,
4-ethoxy-6-(3-(tert-butoxycarbonyl)phenyl)pteridin-2-ylamine,
4-ethoxy-6-(4-(tert-butoxycarbonyl)phenyl)pteridin-2-ylamine,
4-ethoxy-6-(2,3,4-trifluorophenyl)pteridin-2-ylamine,
4-ethoxy-6-(4-tert-butylphenyl)pteridin-2-ylamine,
4-ethoxy-6-(4-(tetrahydro-2H-pyran-2-yloxy)phenyl)pteridin-2-ylamine,
4-ethoxy-6-(4-(2-thienyl)phenyl)pteridin-2-ylamine,
4-ethoxy-6-(2,4,6-trimethylphenyl)pteridin-2-ylamine,
4-ethoxy-6-(3,4,5-trimethoxyphenyl)pteridin-2-ylamine,
4-ethoxy-6-(4-vinylphenyl)pteridin-2-ylamine,
4-ethoxy-6-(4-(2-hydroxyethoxy)phenyl)pteridin-2-ylamine,
4-ethoxy-6-(6-benzyloxynaphth-2-yl)pteridin-2-ylamine,
4-ethoxy-6-(naphth-1-yl)pteridin-2-ylamine,
4-ethoxy-6-(naphth-2-yl)pteridin-2-ylamine,
4-ethoxy-6-(4'-benzoyl[1,1'-biphenyl]-4-yl)pteridin-2-ylamine,
4-ethoxy-6-(1-biphenylyl)pteridin-2-ylamine,
4-ethoxy-6-(oxoindan-5-yl)pteridin-2-ylamine,
4-ethoxy-6-(benzodioxolyl)pteridin-2-ylamine,
4-ethoxy-6-(2-acetamidopyridin-5-yl)pteridin-2-ylamine,
4-ethoxy-6-(2-aminopyridin-5-yl)pteridin-2-ylamine,
4-ethoxy-6-(2-aminopyrimidin-5-yl)pteridin-2-ylamine,
4-ethoxy-6-(1,4-benzodioxan-6-yl)pteridin-2-ylamine,
4-ethoxy-6-(1-benzothien-3-yl)pteridin-2-ylamine,
4-ethoxy-6-(2-benzyloxypyridin-5-yl)pteridin-2-ylamine,
4-ethoxy-6-(1-benzyl-1H-pyrazol-4-yl)pteridin-2-ylamine,
4-ethoxy-6-(2-bromo-3-chloropyridin-4-yl)pteridin-2-ylamine,
4-ethoxy-6-(5-bromo-2,3-dihydrobenzo[b]furan-7-yl)pteridin-2-ylamine,
4-ethoxy-6-(2-bromo-3-methylpyridin-5-yl)pteridin-2-ylamine,
4-ethoxy-6-(2-bromopyridin-5-yl)pteridin-2-ylamine,
4-ethoxy-6-(3-bromopyridin-5-yl)pteridin-2-ylamine,
4-ethoxy-6-(5-bromothien-2-yl)pteridin-2-ylamine,
4-ethoxy-6-(2-chloro-6-isopropylpyridin-3-yl)pteridin-2-ylamine,
4-ethoxy-6-(2-chloro-3-methylpyridin-5-yl)pteridin-2-ylamine,
4-ethoxy-6-(2-[4-(4-chlorophenylsulfonyl)piperazin-1-yl]pyridin-5-yl)pteridin-2-ylamine,
4-ethoxy-6-(2-chloropyrid-4-yl)pteridin-2-ylamine,
4-ethoxy-6-(2-chloropyrid-5-yl)pteridin-2-ylamine,
4-ethoxy-6-(dibenzo[b,d]furan-4-yl)pteridin-2-ylamine,
4-ethoxy-6-(2-chloro-3-fluoropyridin-4-yl)pteridin-2-ylamine,
4-ethoxy-6-(dibenzo[b,d]thien-4-yl)pteridin-2-ylamine,
4-ethoxy-6-(3,4-dihydro-2H-1,5-benzodioxepin-7-yl)pteridin-2-ylamine,
4-ethoxy-6-(3,6-dihydro-2H-pyridine-1-tert-butoxycarbonyl)pteridin-2-ylamine,
4-ethoxy-6-(2,5-dibromopyridin-3-yl)pteridin-2-ylamine,
4-ethoxy-6-(2,6-dichloropyridin-3-yl)pteridin-2-ylamine,
4-ethoxy-6-(2,3-dihydro-1-benzofuran-5-yl)pteridin-2-ylamine,
4-ethoxy-6-(2,6-dimethoxypyridin-5-yl)pteridin-2-ylamine, 4-ethoxy-6-(2,6-dimethoxypyridin-3-yl)pteridin-2-ylamine,
4-ethoxy-6-(2,4-dimethoxypyrimidin-5-yl)pteridin-2-ylamine,
4-ethoxy-6-(3,5-dimethylisoxazol-4-yl)pteridin-2-ylamine,
4-ethoxy-6-(2-(3-N,N-dimethylaminopropoxy)pyridin-5-yl)pteridin-2-ylamine,
4-ethoxy-6-(3,5-dimethylpyrazol-4-yl)pteridin-2-ylamine,
4-ethoxy-6-(1-[1,3]dioxolan-2-ylmethyl-1H-pyrazol-4-yl)pteridin-2-ylamine,
4-ethoxy-6-(2,4-dioxo-1,2,3,4-tetrahydro-5-pyrimidinyl)pteridin-2-ylamine,
4-ethoxy-6-(2,4-di(tert-butoxy)pyrimidin-5-yl)pteridin-2-ylamine,
4-ethoxy-6-(2-ethoxypyridin-3-yl)pteridin-2-ylamine,
4-ethoxy-6-(2-fluoro-3-methylpyridin-5-yl)pteridin-2-ylamine,
4-ethoxy-6-(2-fluoropyridin-5-yl)pteridin-2-ylamine,
4-ethoxy-6-(5-formyl-2-furyl)pteridin-2-ylamine,
4-ethoxy-6-(5-formylthien-2-yl)pteridin-2-ylamine,
4-ethoxy-6-(furan-2-yl)pteridin-2-ylamine,
4-ethoxy-6-(2-hydroxypyridin-5-yl)pteridin-2-ylamine,
4-ethoxy-6-(1-isobutyl-1H-pyrazol-4-yl)pteridin-2-ylamine,
4-ethoxy-6-(isoquinolin-4-yl)pteridin-2-ylamine,
4-ethoxy-6-(2-methoxypyridin-3-yl)pteridin-2-ylamine,
4-ethoxy-6-(2-methoxypyrimidin-5-yl)pteridin-2-ylamine,
4-ethoxy-6-(5-methyl-1-benzothien-2-yl)pteridin-2-ylamine,
4-ethoxy-6-(1-(3-methylbutyl)-1H-pyrazol-4-yl)pteridin-2-ylamine,
4-ethoxy-6-(5-methylfuran-2-yl)pteridin-2-ylamine,
4-ethoxy-6-(1-methylindol-5-yl)pteridin-2-ylamine,
4-ethoxy-6-(5-methyl-3-phenyl-4-isoxazolyl)pteridin-2-ylamine,
4-ethoxy-6-(5-(methylthio)thien-2-yl)pteridin-2-ylamine,
4-ethoxy-6-(2-(4-methylpiperazinyl)pyridin-4-yl)pteridin-2-ylamine,
4-ethoxy-6-(2-(4-methylpiperazinyl)pyridin-5-yl)pteridin-2-ylamine,
4-ethoxy-6-(1-methyl-1H-pyrazol-4-yl)pteridin-2-ylamine,
4-ethoxy-6-(3-methylpyridin-2-yl)pteridin-2-ylamine,
4-ethoxy-6-(5-methylpyridin-2-yl)pteridin-2-ylamine,
4-ethoxy-6-(5-methylpyridin-3-yl)pteridin-2-ylamine,
4-ethoxy-6-(2-methoxypyridin-5-yl)pteridin-2-ylamine,
4-ethoxy-6-(4-methylthien-2-yl)pteridin-2-ylamine,
4-ethoxy-6-(5-methylthien-2-yl)pteridin-2-ylamine,
4-ethoxy-6-(2-(2-morpholinoethylamino)-pyridin-5-yl)pteridin-2-ylamine,
4-ethoxy-6-(2-(2-morpholinoethyl)-1H-pyrazol-4-yl)pteridin-2-ylamine,
4-ethoxy-6-(2-(morpholin-1-yl)-pyridin-5-yl)pteridin-2-ylamine,
4-ethoxy-6-(1-(phenylsulfonyl)-1H-indol-3-yl)pteridin-2-ylamine,
4-ethoxy-6-(5-phenyl-2-thienyl)pteridin-2-ylamine,
4-ethoxy-6-(2-(piperazin-1-yl)-pyridin-5-yl)pteridin-2-ylamine,
4-ethoxy-6-(2-(piperazin-1-yl)-pyridin-4-yl)pteridin-2-ylamine,
4-ethoxy-6-(1-propyl-1H-pyrazol-4-yl)pteridin-2-ylamine,
4-ethoxy-6-(pyrazol-4-yl)pteridin-2-ylamine,
4-ethoxy-6-(pyridin-4-yl)pteridin-2-ylamine,
4-ethoxy-6-(4-phenoxathiinyl)pteridin-2-ylamine,
4-ethoxy-6-(quinolin-8-yl)pteridin-2-ylamine,
4-ethoxy-6-(quinolin-3-yl)pteridin-2-ylamine,
4-ethoxy-6-(2-(4-tert-butoxycarbonylpiperazinyl)-pyrid-4-yl)pteridin-2-ylamine,
4-ethoxy-6-(1-tert-butoxycarbonyl-1H-pyrazol-4-yl)pteridin-2-ylamine,
4-ethoxy-6-(1-tert-butoxycarbonyl-2-pyrrolyl)pteridin-2-ylamine,
4-ethoxy-6-(1-(tert-butoxycarbonyl)-5-bromo-1H-indol-2-yl)pteridin-2-ylamine,
4-ethoxy-6-(1-(tert-butoxycarbonyl)-1H-indol-5-yl)pteridin-2-ylamine,
4-ethoxy-6-(1-(tert-butoxycarbonyl)-5-methoxy-1H-indol-2-yl)pteridin-2-ylamine,
4-ethoxy-6-(1-thianthrenylthien-3-yl)pteridin-2-ylamine, and
4-ethoxy-6-(1,3,5-trimethyl-1H-pyrazol-4-yl)pteridin-2-ylamine.

The invention claimed is:
1. A pteridine derivative selected from the group consisting of:
4-ethoxy-6-(4-(trifluoromethoxy)phenyl)pteridin-2-amine,
dimethyl (4-(2-amino-4-ethoxypteridin-yl)phenyl)methylphosphonate,
4-ethoxy-6-(pyridin-3-yl)pteridin-2-amine,
4-ethoxy-6-(1H-pyrazol-5-yl)pteridin-2-amine,
4-ethoxy-6-(pyrimidin-5-yl)pteridin-2-amine,
4-ethoxy-6-(2-fluoropyridin-3-yl)pteridin-2-amine,
4-ethoxy-6-(1H-indol-5-yl)pteridin-2-amine,
4-ethoxy-6-(4-(methylsulfonyl)phenyl)pteridin-2-amine,
4-ethoxy-6-(pyridin-4-yl)pteridin-2-amine,
4-ethoxy-6-(1H-pyrazol-4-yl)pteridin-2-amine,
4-ethoxy-6-(3-(trifluoromethoxy)phenyl)pteridin-2-amine,
4-(2-amino-4-ethoxypteridin-6-yl)-N-cyclopropylbenzamide,
5-(2-amino-4-ethoxypteridin-6-yl)thiophene-2-carbonitrile,
4-ethoxy-6-(2-(trifluoromethoxy)phenyl)pteridin-2-amine,
6-(5-chlorothiophen-2-yl)-4-ethoxypteridin-2-amine,
1-(4-(2-amino-4-ethoxypteridin-6-yl)phenyl)pyrrolidin-2-one,
5-(2-amino-4-ethoxypteridin-6-yl)indolin-2-one,
4-ethoxy-6-(6-methoxypyridin-3-yl)pteridin-2-amine,
4-ethoxy-6-(isoxazol-4-yl)pteridin-2-amine,
methyl 4-(2-amino-4-ethoxypteridin-6-yl)phenylcarbamate,
6-(benzofuran-2-yl)-4-ethoxypteridin-2-amine,
4-ethoxy-6-morpholinopteridin-2-amine,
4-ethoxy-6-(3-methylpyridin-4-yl)pteridin-2-amine,
4-ethoxy-6-(2-methoxypyridin-4-yl)pteridin-2-amine,
4-ethoxy-6-(2-methylpyridin-4-yl)pteridin-2-amine,
4-ethoxy-6-(pyridin-2-yl)pteridin-2-amine,
4-morpholino-6-(3-(trifluoromethoxy)phenyl)pteridin-2-amine,
4-morpholino-6-(4-(trifluoromethoxy)phenyl)pteridin-2-amine,
4-morpholino-6-(4-(morpholinomethyl)phenyl)pteridin-2-amine,
dimethyl (4-(2-amino-4-morpholinopteridin-6-yl)phenyl)methylphosphonate,
6-(4-(methylsulfonyl)phenyl)-4-morpholinopteridin-2-amine,
6-(1H-indol-5-yl)-4-morpholinopteridin-2-amine,
4-morpholino-6-(pyrimidin-5-yl)pteridin-2-amine,
4-morpholino-6-(pyridin-3-yl)pteridin-2-amine,
6-(2-fluoropyridin-3-yl)-4-morpholinopteridin-2-amine,
6-(furan-3-yl)-4-morpholinopteridin-2-amine,
4-morpholino-6-(1H-pyrazol-5-yl)pteridin-2-amine,

4-(2-amino-4-morpholinopteridin-6-yl)-N-cyclopropyl-benzamide,
4-morpholino-6-(pyridin-4-yl)pteridin-2-amine,
4-morpholino-6-(1H-pyrazol-4-yl)pteridin-2-amine,
5-(2-amino-4-morpholinopteridin-6-yl)thiophene-2-carbonitrile,
6-(benzo[b]thiophen-2-yl)-4-morpholinopteridin-2-amine,
6-(5-chlorothiophen-2-yl)-morpholinopteridin-2-amine,
1-(4-(2-amino-4-morpholinopteridin-6-yl)phenyl)pyrrolidin-2-one,
methyl 4-(2-amino-4-morpholinopteridin-6-yl)phenylcarbamate,
6-(6-methoxypyridin-3-yl)-4-morpholinopteridin-2-amine,
6-(isoxazol-4-yl)-4-morpholinopteridin-2-amine,
6-(benzofuran-2-yl)-4-morpholinopteridin-2-amine,
5-(2-amino-4-morpholinopteridin-6-yl)indolin-2-one,
N-(4-(2-amino-4-morpholinopteridin-6-yl)phenyl)isobutyramide,
N-(4-(2-amino-4-morpholinopteridin-6-yl)phenyl)pivalamide,
(S)-tert-butyl 1-(4-(2-amino-4-morpholinopteridin-6-yl)phenylamino)-3-hydroxy-1-oxopropan-2-ylcarbamate,
(S)-tert-butyl 1-(4-(2-amino-4-morpholinopteridin-6-yl)phenylamino)-1-oxopropan-2-ylcarbamate,
cyclopropane carboxylic acid [4-(2-amino-4-morpholin-4-yl-pteridin-6-yl)-phenyl]-amide,
6-(2,3-difluorophenyl)-pteridine-2,4-diamine,
(S)-2-amino-N-(4-(2-amino-4-morpholinopteridin-6-yl)phenyl)-3-hydroxypropanamide,
(S)-2-amino-N-(4-(2-amino-4-morpholinopteridin-6-yl)phenyl)propanamide,
4-[2-Amino-6-(4-fluoro-phenyl)-pteridin-4-yloxy]-2-methyl-butan-2-ol,
6-(4-Fluoro-phenyl)-4-(2-morpholin-4-yl-ethoxy)-pteridin-2-ylamine,
6-(4-Fluoro-phenyl)-4-(3-morpholin-4-yl-propoxy)-pteridin-2-ylamine,
4-Cyclopropylmethoxy-6-(4-fluoro-phenyl)-pteridin-2-ylamine,
4-Cyclobutylmethoxy-6-(4-fluoro-phenyl)-pteridin-2-ylamine,
6-(4-Fluoro-phenyl)-4-(tetrahydro-furan-3-yloxy)-pteridin-2-ylamine,
4-Ethylsulfanyl-6-(4-fluoro-phenyl)-pteridin-2-ylamine,
6-(4-fluoro-phenyl)-pteridine-2,4-diamine,
N-4-Cyclopropyl-6-(4-fluoro-phenyl)-pteridine-2,4-diamine,
4-(2,6-Dimethyl-morpholin-4-yl)-6-(4-fluoro-phenyl)-pteridin-2-ylamine,
N-4-Cyclohexyl-6-(4-fluoro-phenyl)-pteridine-2,4-diamine,
N-4-(3-Methyl-benzyl)-6-(4-fluoro-phenyl)-pteridine-2,4-diamine,
N-4-(3-Fluoro-benzyl)-6-(4-fluoro-phenyl)-pteridine-2,4-diamine,
6-(4-Fluoro-phenyl)-4-(4-methyl-piperazin-1-yl)-pteridin-2-ylamine,
6-(4-Fluoro-phenyl)-4-piperazin-1-yl-pteridin-2-ylamine,
N-4-Cyclopropylmethyl-6-(4-fluoro-phenyl)-pteridine-2,4-diamine,
6-(4-Fluoro-phenyl)-4-pyrrolidin-1-yl-pteridin-2-ylamine,
4-Ethoxy-6-(4-fluoro-phenyl)-pteridine,
4-isopropoxy-6-(4-fluoro-phenyl)-pteridine,
4-(2-methoxy-ethoxy)-6-(4-fluoro-phenyl)-pteridine,
[6-(4-Fluoro-phenyl)-pteridin-4-yl]-(4-methyl-cyclohexyl)-amine,
[6-(4-Fluoro-phenyl)-pteridin-4-yl]-(4-methyl-cyclohexyl)-amine, and
4-Ethylsulfanyl-6-(4-fluoro-phenyl)-pteridine
and/or a pharmaceutically acceptable addition salt thereof and/or a stereoisomer thereof and/or a mono- or a di-N-oxide thereof.

2. A pharmaceutical composition comprising as an active principle at least one pteridine derivative according to claim 1, or a pharmaceutically acceptable addition salt thereof, and one or more pharmaceutically acceptable excipients.

3. A pharmaceutical composition according to claim 2, further comprising one or more other antiviral drugs.

4. A method of treatment of an infection due to a virus, by administering to a patient in need thereof a therapeutically effective amount of a pteridine derivative according to claim 1, or a pharmaceutically acceptable addition salt thereof, wherein said virus belongs to the Flaviviridae family.

5. A method according to claim 4, wherein said virus belongs to a genus selected from the group consisting of Genus *Flavivirus*, Genus *Hepacivirus* and Genus *Pestivirus*.

6. A method according to claim 4, wherein said virus is hepatitis C virus.

7. A method according to claim 4, wherein said administration is oral administration.

8. A method according to claim 4, wherein said therapeutically effective amount is from 0.01 mg to 20 mg per day per kg bodyweight of said patient.

9. A method according to claim 4, wherein said at least one pteridine derivative is administered together with one or more other antiviral drugs.

10. A method according to claim 9, wherein said other antiviral drug is selected from the group consisting of interferon alpha, ribavirin, NS3 protease inhibitors, and nucleoside- or non-nucleoside-based inhibitors of NS5B polymerase.

11. A pteridine derivative selected from the group consisting of:
4-(2-amino-4-ethoxypteridin-6-yl)-N-methylbenzamide,
6-(benzo[b]thiophen-2-yl)-4-ethoxypteridin-2-amine,
6-(4-Fluoro-phenyl)-4-(2,2,2-trifluoro-ethoxy)-pteridin-2-ylamine,
4-Benzyloxy-6-(4-fluoro-phenyl)-pteridin-2-ylamine,
and/or a pharmaceutically acceptable addition salt thereof and/or a stereoisomer thereof and/or a mono- or a di-N-oxide thereof.

12. A pharmaceutical composition comprising as an active principle at least one pteridine derivative according to claim 11, or a pharmaceutically acceptable addition salt thereof, and one or more pharmaceutically acceptable excipients.

13. A pharmaceutical composition according to claim 12, further comprising one or more other antiviral drugs.

* * * * *